(12) United States Patent
Guerrero et al.

(10) Patent No.: US 6,370,423 B1
(45) Date of Patent: Apr. 9, 2002

(54) METHOD FOR ANALYSIS OF BIOLOGICAL VOLTAGE SIGNALS

(76) Inventors: Juan R. Guerrero; Juan C. Guerrero, both of 3615 Dover Rd., Durham, NC (US) 27707

( * ) Notice: Subject to any disclaimer, the term of this patent is extended or adjusted under 35 U.S.C. 154(b) by 0 days.

(21) Appl. No.: 09/405,233

(22) Filed: Sep. 24, 1999

Related U.S. Application Data

(60) Provisional application No. 60/103,154, filed on Oct. 5, 1998.

(51) Int. Cl.[7] ................................................. A61B 5/04
(52) U.S. Cl. ....................... 600/513; 600/509; 600/515; 600/516; 600/517; 600/518; 600/519; 600/521; 600/523; 600/524; 600/544; 600/546
(58) Field of Search ................................. 600/509, 513, 600/515, 516, 517, 518, 519, 523, 524, 528, 544, 546, 521

(56) References Cited

U.S. PATENT DOCUMENTS

| | | |
|---|---|---|
| 3,229,687 A | 1/1966 | Holter et al. |
| 4,006,737 A | 2/1977 | Cherry |
| 4,098,267 A | 7/1978 | Stein et al. |
| 4,183,354 A | 1/1980 | Sibley et al. |
| 4,211,238 A | 7/1980 | Shu et al. |
| 4,316,249 A | 2/1982 | Gallant et al. |
| 4,333,475 A | 6/1982 | Moreno et al. |
| 4,336,810 A | 6/1982 | Anderson et al. |
| 4,467,324 A * | 8/1984 | Bachman ..................... 340/722 |
| 4,633,881 A | 1/1987 | Moore et al. |
| 4,667,682 A | 5/1987 | Ihlenfeld, III |
| 4,883,065 A | 11/1989 | Kelen |
| 4,989,610 A | 2/1991 | Patton et al. |
| 5,205,295 A | 4/1993 | Del Mar et al. |
| 5,398,183 A | 3/1995 | Elliott |
| 5,433,209 A | 7/1995 | Gallant et al. |
| 5,683,423 A * | 11/1997 | Post ............................... 607/5 |
| 5,941,830 A * | 8/1999 | Williams ..................... 600/509 |
| 5,995,868 A * | 11/1999 | Dorfmeister et al. ........ 600/544 |
| 6,053,872 A * | 4/2000 | Mohler ........................ 600/485 |

* cited by examiner

*Primary Examiner*—Angela D. Sykes
*Assistant Examiner*—Frances P. Oropeza
(74) *Attorney, Agent, or Firm*—Nixon & Vanderhye P.C.

(57) ABSTRACT

Method of analyzing biological signals representative of voltage changes, including obtaining an analog biological signal representative of voltage changes, using digital processing software to digitize the biological signal, displaying the processed biological signal in analog form on a display in a time compressed format, wherein an amount of compression for the time compressed formal is selected such that graphical patterns are made perceivable on the display that signify an abnormality in the biological signal, and visually analyzing the biological signal on the display to characterize the abnormality.

19 Claims, 40 Drawing Sheets

METHOD FOR ANALYSIS OF BIOLOGICAL VOLTAGE SIGNALS

CROSS-REFERENCE TO RELATED APPLICATIONS

This application hereby claims priority on U.S. Provisional Application No. 60/103,154 filed Oct. 5, 1998, the disclosure of which is hereby incorporated by reference herein in its entirety.

FIELD OF THE INVENTION

The instant invention relates to improved methods and systems for analysis of dynamic electrocardiograms and other similar waves of biological origin with the purpose of facilitating improved diagnosis of pathological states in human and veterinary medicine. More particularly, the instant invention advantageously uses advances in sound wave technology to improve the recovery, preservation, enhancement and cost effective analysis of biological signals to aid research as well as medical and veterinary diagnosis.

BACKGROUND OF THE INVENTION

Coronary heart disease is the main cause of death in many countries. About 50% of those affected do not reach the hospital due to poor recognition of the disease before a cataclysmic, often terminal event has occurred. The present invention facilitates improved recognition of myocardial ischemia in and out of the hospital by lay people with minimum training. Once the nature of the event is recognized, prompt treatment can then be obtained with a net effect in the decrease of morbidity and mortality and thereby providing substantial gains in life span and in quality of life.

Heretofore, visual analysis of the ambulatory electrocardiogram, in its original analog format, has been and remains unsurpassed and it is superior to any and all current computerized forms of analysis. Visual analysis is a very time consuming (hence costly) process, which required an operator with intimate knowledge of electrocardiography and cardiology. For this reason the use of visual analysis has been limited to academic research and it has not been possible to extend its benefit to patient care in the community. The instant invention overcomes this problem and enables identification of the abnormal patterns by any person with normal intelligence with a minimum (few hours) amount of training in the recognition of the discrete visual patterns which are repetitive between and within patients.

The instant invention, referred to herein as the Computerized Visual Analysis Technique or "CVAT", generally relates to the use of state-of-the-art electronics, computer hardware and software and forward looking signal analysis principles of technology for the evaluation of biological signals obtained from isolated cells, tissues, human and animal species to aid research and diagnosis of medical and veterinary disease states. CVAT can be used to process biologic signals such as, but not limited to: 1) the electrocardiogram in all it's forms, and in particular, the continuous electrocardiographic signal such as that obtained with the Holter technique or during on-line, real time monitoring of a patient; 2) the electroencephalogram; 3) the myogram; 4) the phonocardiogram; and 5) Respiratory sound waves including their correlation with the electrocardiogram and encephalogram to diagnose sleep disorders in the hospital and in out of hospital settings.

CVAT remedies major limitations of the current Holter analysis paradigm which is useful only to detect gross arrhythmia on the 24-hr electrocardiogram (ECG). Current computerized analysis of the ambulatory ECG is done without due regards for protection of the integrity, fidelity, resolution or dynamic range of the analog signal recorded. The current methods are unable to reliably detect ambulatory ischemia or risk for potentially lethal arrhythmia. Such risks are not detectable in a cost-effective manner with prior art techniques. These shortcomings of the prior art have a significant impact on cardiovascular morbidity and mortality. CVAT remedies the failure of the current methodology by making full use of the valuable information encoded in the ambulatory electrocardiogram. By failing to disclose evidence of risks for catastrophic events, current Holter analysis lulls clinicians into the falsehood of absence of evidence misrepresented as evidence of absence of potentially lethal risks. Consecutive obsolete methodologic steps in current Holter analysis severely diminish the quantity and degrade the quality of the signal encoded in original Holter recording media.

Mass screening for patients silently at risk for potentially lethal cardiovascular events could save hundreds of thousands lives in the United States alone. Well done ambulatory ECG monitoring is the only method able to detect transient myocardial ischemia and spontaneously occurring electrical alternans. More than half of the myocardial infarcts and sudden cardiac deaths happen without any prior history of cardiac disease. The instant inventor has determined that these occult and lethal risks can be detected and lives saved if Holter analysis is done with all the resources made available by the fast advances constantly made in signal analysis and computer technology.

As many as 80 to 100% of the myocardial ischemic episodes in a patient can be asymptomatic or have uncharacteristic manifestations known as "anginal equivalents" by cardiologists but frequently undetected by non-cardiologists. Silent and or uncharacteristic ischemic events are common especially in females, diabetics, hypertensives, smokers, hypercholesterolemics, etc. Endothelial cell dysfunction and occult coronary heart disease are frequently hidden pathophysiologic causes of catastrophic or lethal cardiac events.

Silent ischemia, especially that which is not induced by physical stress, can be detected only by ambulatory ECG. However, today, the only reliable form of Holter analysis is visual scanning of the magnetic tape itself, not the "over reading" of the expunged and distorted digital file which misrepresents the original signal. Visual analysis by an expert electrocardiographer is a very time consuming method used only by highly motivated experts in research programs. Due to time and cost involved, visual analysis of the analog signal cannot be applied to clinical practice or mass screening of at risk population with known methods. To detect ischemia, special attention must be paid to microvolt range changes in the ECG, which are not preserved or duly analyzed by current Holter algorithms. There is a need in the art to develop an improved method of Holter analysis that can be made cost effective by not requiring highly sophisticated operator skills. In accordance with the invention, preservation of the signal integrity, dynamic range, fidelity and resolution in the time and voltage domains are of paramount importance for accurate diagnosis of electrocardiographic abnormalities. These considerations are literally of vital importance especially regarding the microvolt region of the ECG where the ventricular repolarization is encoded.

The current computerized methods of Holter analysis use communications engineering techniques and thoroughly obsolete computer hardware and software. Communications engineering paradigms and techniques are best limited to the evaluation of non-biological signals where reproducibility and repetition of waves and other phenomena are the norm. Biologic signals, such as the electrocardiogram, arise from complex biological entities where individuality, constant variation and irreproducibility are expected. A major drawback of engineering autocorrelation is that it is sensitive to waveform changes in the time domain (X-axes) and poorly sensitive to changes in the voltage domain (Y-axes). In current Holter analysis, autocorrelation is wrongly applied to a small sample of degraded biological signal with poor dynamic gain which magnifies the limitations of autocorrelation to recognize voltage changes. Non-biological techniques used to analyze biological data yield, at best, mediocre results, which become poor when analysis is done using a distorted, minuscule fraction of the original signal recorded.

The present invention remedies the deficiency of the current art by completely turning away from over reliance in engineering paradigms not applicable to biology and technology and methodology which has long become obsolete. Rather than using autocorrelational techniques, CVAT analyzes morphology, Avisual patterns and internal harmony in the time intervals. Since it's discovery at the beginning of the century, electrocardiography remains a highly visual, pattern and morphology based discipline. Despite sophisticated efforts (such as neural network or fractal strategies) to advance computer science, humans still do better visual pattern recognition than computers. In CVAT, morphologic patterns are quickly and easily recognized by non sophisticated technicians. Expansion of abnormal, visually compressed, ECG patterns lead to precise identification of important, classical electrocardiographic signs that can not be identified by current Holter analysis. CVAT evaluates time intervals as reflection of harmony or disharmony within the recording; comparisons with the "norm" are done with caution. Current Holter computer analysis relies on quantification of duration and voltages in a digital file degraded in quantity and quality to compare these findings to idealized "normal" values obtained with different and better equipment There are two basic types of ambulatory ECG recording systems. The "retrospective" system (commonly known as Holter recording) analyzes the collected data after completion of the signal recording phase. The "real-time" system analyzes data as it is being recorded. Retrospective systems record the ECG on magnetic tape (usually the cassette type) or flash cards to subsequently analyze the data. In either system, the recording is done through a plurality of input leads attached through electrodes to various points on the patient's chest. To analyze the ECG, real-time systems generally include a microprocessor in conjunction with the electronic storage device. Both the real-time and the retrospective recording systems are designed to interface with a scanner through a magnetic tape reader or an electronic interface to download the collected information for analysis, editing, storage, and reporting.

To record sound, cassette decks use a magnetic tape speed of 55 mm per second across the recording head. For Holter recording the tape speed is reduced 50 to 100 times to speeds of 1.1 to 0.55 mm per second. Such drastic speed reduction is necessary to do 24 hours recordings without changing cassettes. Speed fluctuation in the 10% range is a signal acquisition problem; the best research efforts have dropped it to 3%, which is still too high for accurate quantitative ECG analysis. The time-base fluctuation is magnified when the low-speed recording is played back at very high speeds. The magnetic tape is orders of magnitude richer in signal quantity and quality than the very small digital file used for current forms of analysis. The norm today is to digitize the analog signal by playing back the cassette tapes at speeds as fast as 480 times real time; this is the beginning of major degradation of the analog ECG.

Cassette tape decks used for Holter processing are inexpensive, less than precise instruments. High-speed playback degrades fidelity by limiting frequency response. Inaccuracy and signal deterioration is also introduced by biasing and/or misalignment of the tape on the play back head during high-speed play back. Tape stretching due to repeated stopping and starting of the tape is another source of signal degradation. CVAT solves these problems, in part, by using the high quality decks to play back the tape once, in an uninterrupted manner, at a speed preferably lower than 37 times real time. The digital signal may, for example, then be copied from a hard drive and archived in a compact disc.

Independent channel enhancement of the dynamic range is an important step introduced by CVAT and not done in the current Holter art. The signal encoded in each channel of the magnetic tape is fed into a sound mixer for independent expansion of the dynamic range prior to digital encoding using the best possible or high quality sound card. In accordance with the invention, sampling of the analog signal is preferably done at rates of 44,100 to 96,000 Hz with 16-bits quantization, per sample, per channel. Higher sampling and quantization rates may also be used. The current Holter art samples, at best, at 8,000 Hz with 8-bits cards without preservation of the signal integrity or enhancement of dynamic range prior to analog to digital conversion.

Current Holter analysis is entirely dependent upon the extraction of an unselected fraction of the analog signal encoded in a 24-hour Holter tape. Current algorithms use elision and omission of vast amounts of the originally recorded ECG signal to achieve extreme, unnecessary and deleterious data compression. For instance, at the June 1999 Drug Information Association meeting, Mortara et al. announced, as a novel achievement, the launch of 24 hr 12 leads Holter that will be stored in 16 megabytes of a flash card (over 100,000 heart beats in 1.33 MB per lead per 24 hr). Obsolete clipping and distortion of the signal housed in novel media.

On the surface, the quest for radical compression strategies ("decimating") would seem to be adequate in that it saves memory and greatly enhances the portability of Holter data. However, extreme digital compression gravely decreases the integrity, fidelity, resolution and most importantly the dynamic range of the stored electrocardiogram or any other signal. Furthermore, in the current art, Fast Fourier Transformation is used to artfully create "imaginary points" to replace discarded original data and "smooth" the now partially fictitious signal. Such creative approach is done after drastic lossy compression has irretrievably discarded more than 90% of the original signal with great loss of integrity, dynamic range, resolution and fidelity. The end product is the current art's inability to detect ischemia, pacemaker malfunction, arrythmogenic risk or any condition other than gross ventricular arrhythmia.

Gross data clipping and "imaginary" data points only partially explain the major limitations of today's Holter analysis. The continuing use of vastly outmoded computer and signal processing technology impede the use of Dr. Norman Holter's invention to it's full diagnostic potential to save human lives. Data compression strategies used in current Holter analysis date back to the accidental creation of the Y2K problem. Obsolete and unnecessary compression strategies reduce 24-hours worth of analog Holter data down to a little more than a single megabyte digital file. When the algorithms for Holter analysis were created, extreme limitations in available memory existed. Thus, extreme data compression was needed. It is not accidental that the 1 megabyte and fraction file was perfectly portable in a single 3.5" magnetic floppy disk and suitable for telephonic transmission with now grossly obsolete modems. The fact that Apple Computers, Inc. has altogether ceased to issue computers with 3.5" magnetic floppy disk drives is an indication of how outmoded such a standard for data-volume has become. Thirty years ago, in the infancy of the computer industry, when silicon chips were as expensive as they were limited in their RAM or ROM capacity, data compression was a necessary evil. The Y2K problem was created by a generation of computer programmers who, squeezing every last bit of possibly available data space from the mainframes and PCs of the past, deemed it frivolous to reserve then-precious RAM or ROM memory for the two digits '19' in any and all indications of the year. Now that computer memory is as cheap as it is truly vast in capacity, data compression is an undesirable tool mainly used by producers of entertainment and other non-essential computer applications, i.e. whenever loss of data is deemed acceptable for reasons of practicality and/or fast transmission over consumer-level internet connections.

Like all biologic signals, ECG, as audio data are remarkably hard to compress effectively. All compression routines are known to deteriorate dynamic range, signal quantity and quality. For 8-bit data, a Huffman encoding of the deltas between points has been used in current Holter analysis but deterioration of the signal is quite evident. For 16-bit data, companies like Sony and Philips are spending millions of dollars to develop proprietary schemes that as yet are not fully successful. If somehow, truly non-lossy audio compression would become able to compress 350 megabytes (the size of a CVAT 24 hr ECG file) of data and, even more importantly, preserve high fidelity, resolution and dynamic range intact within a single megabyte of memory, such a compression strategy would be almost a miraculous gift to the computer industry and technology in general. Although great strides of innovation are now being made in techniques of data compression, a 350:1 data compression ratio keeping the integrity of the signal is as yet impossible, nor is it necessary. The fundamental pitfalls of current Holter algorithms are the same than those which were silently at work in the creation of the Y2K bug: automated data compression algorithms which discard data deemed inessential to the projected application. To be of any value, pre-compression selection of data to be invisible, inaudible, illegible, or otherwise useless, is a must. The problem is that such pre-compression decision regarding ambulatory ECG signal is not and can not be made without rendering compressed Holter files useless except for detection of gross arrhythmia.

The much-hyped MPEG Layer 3 (or 'MP3') strategy of digital audio compression, for instance, uses a psychoacoustic algorithm to determine which sonic frequencies in a given audio recording remain ultimately audible to the ear of a listener. The data corresponding to all 'irrelevant' frequencies are then omitted from the resulting compressed sound files. Although the algorithm used in MP3 compression is quite advanced, the process still degrades the quality of the original signal in an invariably noticeable (almost 'trademark') fashion. Such degradation, however, lies within an 'acceptable' window of loss for the consumer-oriented purposes of the technology, i.e. exchanging recordings of popular songs over the Internet. Boasting a powerful 12:1 compression ratio, MP3 is a fairly new compression strategy. Even newer, 'better' strategies are being invented on almost a quarterly basis, but all of them, even the latest 'fractal' compression strategies, still ultimately boil down to the same compression paradigm: automation of the a priori decision to selectively preserve or omit certain types of data. Detection of microvolt and lower voltage changes in the ECG is relatively new in the electrophysiology lab and now brought to ambulatory ECG with the instant CVAT method. It is not yet known which voltage changes are unimportant and to be disposed with impunity.

One overriding fact remains clear: the application of any inherently omissive data compression strategies to a 24 hr ECG recording prior to any and all analysis of the totality of the signal is wrong. The only possible use of such indiscriminately selected file is detection of conditions expected to be apparent within the grossly compressed version of the ECG signal. For the current Holter analysis, that condition was and remains gross arrhythmic events. For a phenomenon as eponymously elusive as 'silent ischemia', for instance, such a stark predetermination of what will and will not be detectable in an electrocardiogram is, literally, the most fatal omission of all. Detection of silent ischemia and risk of fatal arrhythmia is done in the microvolt region of the signal, the area that suffers the most from dynamic range and signal quality deterioration due to obsolete signal processing schemes. Current Holter analysis continuing reliance upon obsolete signal and data handling strategies limits access only to that portion of ECG data which was thought worth representing within a single megabyte of computer memory more than 10 years ago. Holter analysis remains a vastly under addressed technological obsolescence which is an obstacle for detection of risk for lethal events and in doing so puts lives directly at risk.

The numbers speak for themselves: Digital compression of 24 hours of recorded signal down to as low as a single megabyte unnecessarily omits about 99.6% of the ECG which can be easily retrieved from the average 24-hour magnetic Holter tape. It is like attempting to "read" a book while missing 99.6% of the words or "watch" a film with 99.6% of the celluloid frames omitted. Diagnosis of potentially life threatening conditions can and should not be made based on such scanty and non-discriminatingly selected fraction of the ECG stored in the original recording media. Human life protection deserves better than that.

The instant CVAT process for Holter analysis utilizes a completely different method of "data compression" altogether, one which does not omit any portion or aspect of the originally recorded ECG Holter data. Instead of destructive fast play back of the tape and digital compression of the Holter data, CVAT improves the dynamic range electronically prior to slowly encoding the whole, unmodified analog signal using the highest possible sample rate and quantization. CVAT decodes the digital file into an optimum analog display which itself can be visually compressed, magnified at will and processed without suffering any loss, but rather being enhanced by various different processes which are made available by CVAT and its related software. In addition, the only limits containing further development and refinement of the CVAT process are those temporarily imposed by the ephemeral and upwardly spiraling limits of computer and signal analysis technology. The CVAT process remains an infinitely upgradeable, high-quality system which takes Holter analysis orders of magnitude beyond current techniques.

Referring now to FIG. 1, there is shown a exemplary Holter electrocardiogram. The P wave is the ECG representation of the atrial depolarization which cause its contraction. PQ is the segment between the P and the Q; it represents the delay of the electrical wave of depolarization at the atrioventricular node to allow the contraction of the atria and fill the ventricles before the latter depolarize and expel blood into the body. Ta (a microvolt shift in the PQ not present in this figure) is due to abnormal atrial repolarization caused by ischemia. The QRS is the ECG representation of ventricular depolarization which cause ventricular contraction. The ST segment represents the initial repolarization of the ventricles. The ascending limb of the T wave represents epicardial (outer surface of the ventricle) repolarization which changes into endocardial (inner surface of the ventricle) and mesocardial repolarization at the apex of the upright T wave. Ventricular repolarization is complete when the T wave returns to the isoelectric line. Several different morphologies of the T wave are associated with non-homogeneous repolarization, a sign of myocardial cell hypoxygenation and risk for lethal arrhythmia. TP is the isoelectric segment between the offset of the T and the onset of the P waves. TP must be considered as the isoelectric line when Ta is present. The second beat is a premature depolarization characterized by abnormal QRS and T morphology as well as greater voltage and duration than the normal beats.

Experts in non-ambulatory electrocardiography do visual analysis of the 12 lead ECG using 10X optical magnification for which special tracings are taken at two or four times the normal paper speed (i.e. 50 to 100 mm per second paper speed) with at least twice the electrical gain (i.e. 1 millivolt inscribing a 20 mm deflection). The tracings are done using good quality, well maintained and well-calibrated stationary electrocardiographs. The best examples of this art are in research done in Scandinavia. There is a pressing need to apply similar or better care to the processing and analysis of the ambulatory electrocardiogram.

Norman J. Holter Ph. D. created Holter technology using radio-transmitted electrocardiograms in the 1940's. The method was used for diagnosis of arrhythmia. The first algorithms for computer assisted analysis were designed to detect and classify premature or aberrant beats for the diagnosis of arrhythmia. Attempts to automate detection of myocardial ischemia started in the early 1970's. Systems to do Holter ECG processing and evaluation are well known as disclosed in U.S. Pat. Nos. 3,229,687; 4,006,737; 4,098,267; 4,183,354; 4,211,238; 4,316,249; 4,333,475; 4,336,810; 4,633,881; 4,667,682; 4,883,065; 4,989,610; 5,205,295; 5,398,183 and 5,433,209.

Automated evaluation of ST segment shifts was attempted with only minor modifications of the basic signal processing and algorithms used for arrhythmia detection. The ischemia algorithm compares the voltage at one 8-bits point in the ST segment (located 60 to 100 milliseconds beyond the J point—the junction of the QRS and the ST segment) to the voltage at another 8-bits point on the PQ taken as the isoelectric line. Correction for presence of Ta (atrial ischemia) is unheard off in the current art, since it is unable to visualize this subtle but important change. Hence, in the current art, the ST segment (a line and, as such, defined by at least two points) is represented by a single point. The analytic paradigm and totally obsolete limitations in computer technology imposed this major source of false negative reports.

Identification of the isoelectric line in the ECG is of paramount importance for detection of atrial and ventricular ischemia as well as for evaluation of the QT segment and T wave changes indicative of abnormal repolarization and arrhythmogenic risk.

Current Holter algorithms can not detect ECG signs of abnormal repolarization in a reliable and reproducible manner. Ischemic events, represented by ECG signs of abnormal repolarization and depolarization, are usually unexpected and transient. Abnormal repolarization is visualized as microvolt shifts in the PQ segments (Ta) if atrial or ST segment and T wave if ventricular. In the current Holter art, Ta is undetected and mistakenly chosen as the isoelectric point. This false isoelectric point and spill over of the Ta negative voltage into the ST segment are common pitfalls that introduce error in ischemia detection by current algorithms. Down shift of the ST by Ta depends on the degree of atrial ischemia, the heart rate, atrioventricular conduction velocity, etc. CVAT can easily recognize such problems and use the TP segment, instead of the PQ, as the isoelectric reference line. The TP segment is inscribed from the end of the T to the beginning of the P waves in two consecutive beats. CVAT can also identify the influence of Ta into the ST segment and discriminate false positive up sloping ST depression (starting from a depressed J point) from up sloping ST depression likely to be due to ventricular ischemia.

The prior art taught by conventional Holter monitoring systems cannot retrieve, store, display or analyze high fidelity signals in the microvolt or microsecond range. Fast magnetic tape play back done without optimizing the dynamic range, scanty sampling, poor quantization and extreme data compression deteriorate and diminish the signal. However, computer memory (1.2 Megabytes) and processing time are saved and telephonic transmission of a scanty, low fidelity, low resolution, low dynamic range signals file is facilitated. Fast Fourier Transformation and other algorithmic manipulations are used to automate processes, reduce operator time and level of skill, speed analysis and decrease cost. All the above contribute to the poor diagnostic performance of current Holter technology for conditions other than gross arrhythmia.

The present invention (CVAT) preferably uses: the best possible electronic technology for integral signal recovery with preservation and enhancement of the dynamic range, fidelity, time and voltage resolution of biologic waves encoded in any recording media; the best possible computer and signal analysis technology to digitize the analog biologic signals for storage, further enhancement, and archival preservation of the signal; and the best possible electronic, computer and signal analysis technology for the recovery, display and evaluation of the signals for basic research, medical and veterinary diagnosis.

Ambulatory electrocardiography done according to the Holter technique was used for the initial testing of the CVAT method and system. CVAT can be used in research, clinical practice and mass screening as an aid to diagnose cardiovascular conditions which include, but are not limited to: 1) Myocardial ischemia in all it's forms; and 2) Repolarization (including but not limited to QT prolongation and electrical alternans) and depolarization heterogeneity as signs of increased cardiovascular risk.

The instant CVAT invention enables extension of Holter monitoring analysis to the detection and interpretation of ECG signals at and beyond the microvolt and micro second range. These minute changes encode important diagnostic and prognostic information not discernible from current Holter techniques or other forms of electrocardiographic analysis. Conventional Holter monitoring and ECG systems cannot detect, preserve or recover signals at or beyond the microvolt or microsecond range. Exception is made of techniques limited to the electrophysiology laboratory not applicable to mass screening or daily clinical practice outside of specialized centers.

The CVAT invention provides a method for biologic signal analysis by trained but not medically skilled technicians. Cost effective processing is aided by a variety of well identified morphologic patterns obtained by visual compression, in the X (time) axes of the played back signal. The visually compressed patterns are highly suggestive or patognomonic of important electrocardiographic changes which are confirmed by examination of the expanded ECG tracing.

The purpose of algorithms in current use is to provide an ECG evaluating system, as automated as possible, which scans the tape as fast as possible with minimal or no operator interaction. Undue reliance is placed on a physician over reading of very small depictions of low fidelity greatly deteriorated ECG tracings recovered from the digital file. Unless the over reader reviews the whole analog signal encoded in the original recording media (in addition to editing the computer findings), ischemic and other events missed by the computer can not be detected. This is the most common and potentially fatal shortcoming of the current Holter art. Visual examination of the analog recording is exceptional; it is done only in very few research centers and not by Holter analysis services that support clinical practice or research in general.

Current computerized Holter analysis algorithms use heartbeat superimposition and template-matching schemes to recognize departures from normal. Which beats, in a pool of about 100,000 in 24 hours, are the norm for a patient? This is a basic problem which has to be dealt with even when neural networks, used in research only, select beats to "train" the computer to recognize "normal" beats. After digital conversion, each heartbeat becomes a series of digital values representing XY points of the waveform at various intervals. In current Holter analysis the number of digital points per heartbeat is, at best, 33 or lower if the heart rate goes above 60 beats per minute. The computer does beat matching to evaluate the difference between values at various points of the waveform and to compare such values with corresponding points of templates. A match is defined as any sum of the absolute value of each of the differences within a preset range. The closest match is called the matching template. If no template matches, the operator must classify. The degraded signal preserved by the current art allows only the grossest matching which cannot go beyond identification of largely aberrant beats. In addition, current algorithms include software to analyze the series of waveforms according to a nondeterministic logic state analysis. This analysis permits the systems to indicate when waveforms correspond to ventricular ectopy (VE), bigeminy, VE pair, and ventricular tachycardia, only.

A standard waveform has a P wave, a QRS complex and a T wave. As it is well known in the prior art, the QRS complex is generally identified by its major peak, usually the R wave. The T wave is then identified as the first peak after the R wave. A T wave template is used to process the wave quickly and inadvertent recognition of a T wave as an R wave is minimized but still exists. The T wave template is a classification that the operator may apply when asked to classify the 'beat'. Thereafter, any peak that matches the T wave template is totally ignored, as though no peak had been found at the position. If the operator incorrectly classifies a T peak that is or looks like a real beat, that type of beat will be ignored. Therefore, the method is used as a last resort, when setting the other parameters does not help, which can occur with patients who have peaked T waves. Peaked T waves are a common early manifestation of ischemia. Whenever the ST segment shifts up or down due to myocardial ischemia, the T morphology is usually abnormal and not amenable to template classification. While templates work well for arrhythmia, over reliance in abnormal beat classification using predetermined templates is a reason for the poor performance of computer automated Holter analysis in the diagnosis of conditions other than arrhythmia.

The template matching method is probably good enough for ventricular and other gross forms of arrhythmia, which manifest themselves by millivolt range changes in the QRS. However superimposition of fast played back, scantily sampled, mercilessly compressed, filtered, smoothed and/or Fast Fourier Transformed beats cannot be trusted, since it processes a signal different from that originally encoded in the magnetic tape. Template detection may be convenient, but applied to a digital file which lacks integrity, dynamic range, fidelity and resolution, it cannot be sensitive or specific nor can it detect abnormalities in microvolt regions such as the PQ, ST segments or the P and T waves.

The sophisticated cardiology community is aware of the current Holter analysis shortcomings; hence, this method is not routinely used as an aid in the diagnosis of highly lethal cardiovascular risks.

The following passage is taken verbatim (bolding added) from U.S. Pat. No. 5,398,183 issued on Dec. 10, 1990. This algorithm is widely used in patient care and research and further demonstrates the disadvantages of current Holter processing techniques.

"As another feature of the invention, a full disclosure file representing the entire series of waveforms on the tape is generated. The file comprises compressed data of limited resolution and limited sampling rates. The original data is reduced in resolution by skipping, averaging, or otherwise "decimating" samples, only using samples at a rate near 33 samples per second with reference to the patient data. (This is an equivalent rate of 33 samplesisec of the data generated when the patient was originally monitored by the analog Holter monitor. Of course, the data reading rate off the tape is much faster.) In this system 100, this is accomplished by averaging 4 samples, or by picking one out of every fourth sample. The data is scaled in amplitude (and limited) so that the total excursion is 32 levels. The 32 levels are sufficient resolution to plot on a laser plotter at 200 dots/inch, producing a 0.15" tall waveform. The sample frequency (referenced to patient) is sufficient to see all R-peaks of normal beats by position, and to display the waveforms of ventricular beats sufficiently clearly to be identified. The data is then further compressed by using a series of coding steps. First the data is converted to differential coding. (This is a version of DPCM, 'Differential Pulse Code Modulation' in the telecommunications industry). Each sample has the previous sample subtracted from it (as the example in FIG. 7 shows). This is a simple, and computationally efficient means to produce codes which consist mostly of the smaller integers near 0. In fact, the output will often have runs of 0s, or +1s, 0, and −1s. Less frequently the differences will be larger numbers (6 to 31), mostly near the R peaks. The differential output is limited to the range −31 to +31. The data is then encoded further using a variation of 'Huffman' coding, or other codes which use few bits for symbols which occur frequently, and more bits for symbols which occur infrequently. (The symbols to be coded are the 63 integers in the range −31 to 31). This may be combined with run length coding, which is the coding of a repeated sequence of the same symbol with a code representing the sequence in fewer bits than repetitions of the code representing the symbol singly. The result of this coding is to bring the number of bits to represent a data point down to around 2 to 3 bits. This typically allows 24 hours of data to occupy less than 1 megabyte, where a byte is 8 bits. (3/8 byte/sample * 33 sample/sec * 60 sec/min * 60 min/hr * 24 hr/tape=1.07 Megabyte/tape). This allows the full disclosure to typically be stored on a single IBM PC compatible 1.2 Megabyte diskette, or transferred by telephone in 10–20 minutes using the new 9600 Baud Modems."

"Taking every third sample provides a limited sampling rate and scaled differential coding provides limited resolution. Further compression, such as run length and Huffman coding, may then be used so that the full disclosure file can be even further significantly reduced in size. The differential values 0, +1, −1, +2, −2 may be seen to occur more frequently than the larger values of 6 to 31 and −6 to −31. If the smaller integer values are represented by codes using two or three bits, then the size of the file can be further reduced. FIG. 8 is an example of a part of a limited resolution, full disclosure file recreated from differentially encoded, compressed data. The circled areas indicate ventricular ectopy and supra-ventricular ectopy which is clearly recognized even though this portion of the file was created from compressed data."

The best resolution to be expected with the algorithm described in this patent are 33 points in the X axes and 32 points in the Y axes to inscribe one heart beat if the heart rate is 60 beats per minute. If the heart rate goes to 120 per minute there will be, at best, 16 points to describe the whole cycle length.

After the "decimating compression" it is only benign to say that the algorithm driven file will have poor resolution and fidelity. A 24-hour Holter recording is housed in 1.2 Megabytes, and yet a 3-minute song, reproduced with any decent degree of fidelity, takes about 30 to 40 times the memory currently allocated to a 24 hours Holter recording. This is a grave problem that needs immediate redress. In contrast, CVAT encodes the same 24 hours Holter recording in about 350 megabytes. The CVAT file improves the dynamic range and preserves the integrity, fidelity and resolution of the signal recorded. It is not surprising that the quality of the ECG recovered from current Holter analysis algorithms is too poor to identify anything but arrhythmia with some degree of certainty. The substantial difference made by CVAT's preservation and enhancement of the signal has been demonstrated in a retrospective study done comparing CVAT with the best current algorithm analysis. The results of this study are provided below.

The passage below, taken from the U.S. Pat. No. 4,989,610 issued on Feb. 5, 1991, illustrates problems in another crucial point of current Holter analysis (bolding added).

"The first step in this portion of the program reads the six items contained in the beat time log (BTL) for a particular beat 1220 (see FIG. 55). The data in the BTL is 16 bits wide. It includes the bin number (to be assigned by the binning operation (BIN#)), a 32-bit number indicating the time of occurrence of the beat in terms of $\frac{1}{120}$ second samples of time (BTH and BTL), a TEMP location for temporary storage of data, a FLAG word, an 8-bit ST measurement, and an 8-bit ST-slope measurement."

"The data representing one channel of the present beat consists of thirty-two samples. The tenth sample corresponds to the location of the R-wave, as determined by the beat detection software. Nine samples preceding the location of the R-wave and twenty-two samples immediately following the location of the R-wave constitute the remainder of the samples."

"Then, the DSP chip 300 performs the Fast Fourier Transform (FFT) on the thirty-two samples of the channel 1data, producing sixteen pairs of real and imaginary data."

"The pattern describing the members of this first bin are the twelve points in the complex plane 1236, with each point being associated with either channel 1 or channel 2 and with one of the six frequencies. The six pairs of numbers that describe the pattern for the second and following beats are compared, according to their channel and frequency, with the groups of points that defines the bins already in existence. If the twelve points characterizing the morphology of a beat whose bin is being determined are sufficiently close, on a point-by-point basis, to the twelve points of an already existing bin, that beat may be associated with that bin. If the twelve points describing the morphology of a present beat do not come sufficiently close to all twelve points describing all already-existing bin, a new bin is defined. The twelve points defining the new bin are the twelve points characterizing the morphology of the most recent beat. The twelve points describing a beat need not match precisely with the twelve beats defining a bin for the beat to possibly be placed in the bin. The twelve points describing the morphology of the beat are sufficiently close to the twelve points defining the bin if each of the twelve points falls within windows centered on the points defining the bin."

The passage teaches that 32 samples represent a heartbeat in each channel and that these samples are subjected to Fast Fourier Transform to generate "sixteen pairs of real and imaginary data". These sixteen pairs of "real and imaginary" data cannot be expected to fully describe the complex morphology of each heartbeat. With this algorithm, all the microvolt nuances will certainly be irretrievably lost. These brief passages provide strong reasons to render this algorithm useless for anything but arrhythmia detection.

The current automated systems for Holter analysis retrieve only a small portion of the analog signal. Excessively fast play back speed of the tape, low sampling and quantization rates, "lossy" and drastic data compression, Fast Fourier Transform to interpolate imaginary data, filtering, smoothing, etc. are done to accommodate the need for very small data files suitable for telephonic transmission and automated analysis. The price paid is extremely poor ECG data unsuitable for recognition of ischemic and other dire electrocardiographic signs with any degree of certainty.

Myocardial ischemia is the result of oxygen debit in the heart muscle and conduction system due to increased demand or decreased supply of oxygen which cannot be fulfilled because of: 1) organic, fixed, coronary artery stenosis such as that seen in patients with atherosclerotic plaques in the luminal wall of their coronary arteries; 2) functional, episodic, often unpredictable constriction of normal or atherosclerotic coronary arteries; or 3) clot formation over an atherosclerotic plaque.

Although spasm was historically suspected to be a cause of coronary occlusion, from the 1940's to the 1960's the common wisdom was that atherosclerotic arteries were unable to constrict. In the 70's experts in the field demonstrated that atherosclerotic plaques are mostly eccentric with a small free arterial wall (opposite to the atheromatous plaque) likely to cause total occlusion when minor spasm of such small free wall occurs. When coronary artery spasm happens, gaps between the endothelial cells happen, collagen protrusion induces platelet aggregation and in-situ clot formation. Thrombosis can also lead to partial or total occlusion following the arterial spastic episode.

Fixed, organic, atherosclerotic arteries can be readily identified. The conventional 12-lead electrocardiogram can disclose patognomonic signs of permanent (not episodic) ischemia of the heart. The 12-lead electrocardiogram is not expected or designed to detect transient and unpredictable episodes of myocardial ischemia or arrhythmia since it depicts only 3 of the 100,000 or more heart beats we have in 24 hours. For detection of sporadic arrhythmic or ischemic events, usually triggered by diverse stressful stimuli of daily living, properly done Holter recording is the only available method, electrocardiographic or otherwise.

Permanent (not episodic) myocardial ischemia due to fixed coronary artery occlusion can be detected by several methods other than Holter. Electrocardiography and or echocardiography done during standardized exercise challenge can detect ischemia and/or arrhythmia induced by physical stress. Other, more invasive methods, such as drug induced stress testing (the pharmacologic induction of increased cardiac oxygen demand by administration of drugs which elevate the heart rate), nuclear radiology or cardiac catheterization, are designed to detect fixed coronary artery occlusion.

All methods available today, other than the Holter technique, are unable to detect myocardial ischemia due to transient spastic and/or thrombotic causes of decreased coronary blood flow. Coronary artery spasm frequently happens without preceding elevation of the heart rate and/or blood pressure and is commonly triggered by neurohormonal, emotional and/or environmental (e.g. exposure to cold, second hand smoking etc) factors, not inducible in controlled cardiovascular laboratory circumstances. Hence, this grave condition escapes detection unless Holter recordings are done under the fleeting and often difficult to identify forms of daily life stress that induces the attacks in a given patient. The current Holter recording equipment has enough fidelity to detect these episodes. The limiting factor is the current computerized Holter analysis that is unsuitable for detection of anything but gross arrhythmia. The current art suffers from false negative findings which have dire consequences for patients considered healthy when they are not. Today, the only reliable method to analyze Holter recordings for ischemia is the direct visual inspection of the analog tape by a competent electrocardiographist. Such visual Holter analysis is time consuming and hence, done only in few research efforts and not cost effective or applicable to daily clinical practice or mass screening.

Computerized Holter analysis was designed for the detection of arrhythmia, and has remained essentially unchanged. Arrhythmia induces gross changes in the time and voltage domains of the recording. Algorithms to detect arrhythmia rely on large, millivolt range. Ischemia-induced abnormalities are in the microvolt range and are unlikely to stand the decimating affects of current algorithms devoted to minimize file size. Norman J. Holter, Ph. D. originally designed his valuable method and technology (U.S. Pat. No. 3,229,687. January 1966. Holter et al.) for the study of heart rate and rhythm. The minor changes introduced by computer algorithms are not sufficient for reliable detection of ischemia or risk for potentially lethal arrhythmia.

In cardiovascular diagnosis, it is important to monitor the level of the ST segment of the heart beat signal since the amplitude and direction of the shift correlate well with the oxygen balance in the patient's heart. A heart receiving insufficient oxygen experiences predictable anomalies in the ST segment called "ST Depression" or "ST Elevation". The names relate to the directional shift (negative or positive microvolts in reference to the isoelectric line) and shape of the ST segment of the ECG waveform during periods of insufficient heart oxygenation. The magnitude and morphologic changes of the T wave are additional indicators of ischemia which the current algorithms are unable to detect. The CVAT method makes full use of morphologic changes in all portions of the ECG to aid in the diagnosis of ischemia and arrhythmia risk.

The normal ST segment is located at the isoelectric level which usually aligns with the PQ or TP segments. PQ segment shift is frequently due to artifacts or ischemia of the atria (Ta). The normal condition is generally referred to as the "isoelectric alignment" of the ST segment. ST segment shifts, measured in microvolts, above or below the isoelectric line are a reflection of abnormal myocardial repolarization due to inadequate LA oxygenation of the heart. Ischemia not felt by the patient is generally referred to as "silent ischemia", while ischemia which is painful is called "angina". All or most ischemic events may be silent. Frequently 80 to 90% of the ischemic episodes can be asymptomatic or have uncharacteristic manifestations known as angina equivalents. However, silent or symptomatic, ischemia can equally induce arrhythmia, myocardial infarction or sudden death. It is suspected that silent ischemia is the underlying problem in the 50% of patients who have myocardial infarctions or die suddenly without having had any premonitory symptoms or signs.

It is very important to identify the isoelectric line and the level of the ST segment in the patient's normal heartbeats in order to be able to properly identify departures from normality. U.S. Pat. No. 5,433,209 issued on Jul. 18, 1995 includes the following passage (not direct quotes and bolding not in the original document):

> For each ECG signal channel, the QRS peak location is approximated from the point at which a beat is detected over a beat detection threshold. Then, the ST algorithm backs up 10 samples from the peak of the QRS complex to approximately land on the PR interval of the beat wave form. Next, a region of "minimum activity" is located and the baseline offset, identified as "Base Corr (i)", is found. The "minimum activity" region is found by finding the smaller of the two 3-point absolute value derivatives in a 5 sample window on the PR interval. The baseline offset is taken for the sample which is located 30 samples forward of the QRS peak which is thereafter identified as the ST segment. The baseline offset at the region of "minimum activity" is subtracted from the sample value at this point and the difference, measured in millimeters, is taken to be the ST level. Each time a ST level is calculated, a last eight beats ST level average is also calculated. Each ST level average during the minute is compared to the last eight beat minimum and maximum ST level average to find the minimum and the maximum eight beat average for the minute. Hourly and monitoring period minimum and maximum ST levels are also determined in the above fashion. ST level sums are also maintained in the minute summaries, hour summaries and the end of monitoring period summary, with the corresponding normal beat counts. The minute ST level averages are calculated by dividing the minute ST level sum by the normal beat counts during the minute. The hour ST level averages are also calculated in a similar fashion. The minimum, maximum, and average ST levels are each stored as a signed byte of information. Each value is used along with the gain set for each channel and the analog to digital range set for each channel in order to calculate the ST depression or elevation value. Since, the ST averages all require extensive computations, the computational load is spread over several periodic interrupt cycles. Minute ST level averages are monitored over the entire monitoring period to determine an ST "episode". An "episode" is detected if the minute ST level average in any channel is at least less than −1.0 mm and is sustained at this depressed level for more than a minute. ST episodes of less than −1.0 mm, −2.0 mm, and −3.0 mm and their duration time in minutes are recorded.

All these intensive computational niceties are done on a digital file known to be incomplete and with major fidelity, resolution and dynamic range deficiencies. Hence, it is not surprising that current algorithms miss 9 out of 10 patients whose ischemia can be identified with visual analysis.

In the current practice of cardiology, the goal of therapy for patients with coronary artery disease is being upgraded from simply controlling anginal pain to a more rational and forward looking reduction or elimination of silent and symptomatic ischemic episodes. Any form of ischemia, symptomatic or not, short or long can kill or induce myocardial infarction. Properly done, the Holter method is the only way to detect silent or atypically symptomatic ischemia and has to play an increasingly important role in the management of this serious condition. To play that important role in the detection and monitoring of ischemia the current Holter art risk of false negative analysis must be eliminated. Biologic signal analysis can and should make a quantum leap using, electronic technology, hardware and software developments achieved in the last decade.

Sudden cardiac death (SCD) claims over 350,000 lives annually in the United States; 50% of which had no premonitory symptoms or signs. SCD usually follows an abrupt disruption of heart rhythm primarily due to ventricular fibrillation. Fibrillation occurs when transient triggers impinge upon an electrically unstable heart causing normally organized electrical activity to become disorganized and chaotic. Complete cardiac dysfunction results and may end in sudden death. An episode of poor oxygenation of the heart (myocardial ischemia) is probably the most frequent cause of ventricular fibrillation and death.

A major, and as yet elusive, objective of preventive cardiology is to detect patients at risk for catastrophic arrhythmic cardiac events, including sudden cardiac death. Methodology used to identify subjects at risk must be improved. Electrical alternans is the electrocardiographic manifestation of heterogeneous myocardial repolarization and depolarization. Electrical alternans and ischemia are prominent indicators of risk factors for major catastrophic or lethal cardiac events. Gradual microvolt changes are seen in the ST segment and the T wave and are not as abrupt as the onset of abnormal QRS. Microvolt signals are easily obliterated by poor dynamic range, "decimating" compression algorithms, creation of "imaginary" points, etc used by algorithms in the quest for automation and trans-telephonic transmission of minimized Holter files.

Cost effective, non-invasive, techniques for mass screening and identification of individuals at risk for catastrophic cardiac events that affect close to 2 million persons per year in the US alone are needed. Diagnostic technology must be constantly revised to make full use of the ever improving developments in electronics as well as computer hardware and software. Prompt risk detection, will lead to immediate confirmatory diagnosis, interventional cardiac catheterization, coronary artery by-pass, pharmacologic management, etc., thereby allowing the saving of hundreds of thousand of lives in the world. There is need to develop an improved Holter analysis that can be cost effective in time and level of operator skill and still precise enough to avoid potentially catastrophic false negative reports.

Advent of Holter analysis as a reliable method to detect ischemia and risk for severe arrhythmia will also facilitate targeted new drug development by providing valid objective therapeutic end points, instead of unreliable surrogate endpoints. Cutting age technology has to be used to preserve the fidelity, dynamic range, time and voltage resolution of the recorded signal, a step of paramount importance for the accurate diagnosis of electrocardiographic abnormalities in the microvolt region. Holter analysis obsolescence is the medical counterpart of the Y2K problem with the difference that it's cost in mortality and morbidity is orders of magnitude greater than the Y2K can ever be. This problem is greatly reduced, if not completely solved, by the teachings of the present invention.

The use of the instant invention to process analog electrocardiographic signals makes it possible to evaluate every single beat of the ambulatory electrocardiogram by compacting the signal in a manner that will disclose sui-generis visual patterns which correspond to and readily identify classic, discrete anomalies of the electrocardiogram, described by experts in the field as part of pathologic conditions compromising the cardiovascular system. The understanding of these patterns make it possible to identify the abnormal elements of the electrocardiogram.

The immediate value to mankind provided by the instant invention is that it makes possible identification in a non-invasive and cost-effective manner, patients who have silent myocardial ischemia and hence are at high risk for myocardial infarction, sudden death and other catastrophic events. About one half of patients with myocardial infarction, sudden death, lethal arrhythmias, etc. are patients who have no history of coronary heart disease and are probably carriers of silent myocardial ischemia, which triggers the terminal events leading to the patient's demise. The instant invention enables timely discovery of this covert condition and enables timely anti-ischemic therapy which will result in the saving of millions of lives as well as a decrease in hospital use, disability and improvement of the quality of life of those affected by silent ischemia a potentially lethal condition.

As explained in detail above, instead of visual analysis, computer programs implementing mathematic algorithms are presently routinely used to perform analysis of electrocardiograms in an attempt to detect abnormalities therein. Such computer programs have had only limited success in diagnosing pathological conditions which compromise a patient's cardiovascular system. Due to their cost-effectiveness, however, such mathematical techniques are widely used today. As a result, many patients have had pathological conditions go undetected.

Thus, a need exists for improved methods and systems which enable improved detection of pathological conditions during analysis of the electrocardiogram and other waves of biological origin.

The instant invention advantageously uses algorithms and computer programs created for the purpose of editing, manipulating and/or analyzing sonic and/or electromagnetic waves, such as music processing programs.

SUMMARY OF THE INVENTION

A primary object of the instant invention is to increase the accuracy and decrease the cost of biologic signal analysis for use in mass screening, clinical practice and research.

The instant invention, referred to herein as the Computerized Visual Analysis Technique or "CVAT", generally relates to the use of up-to-date signal processing technology with state-of-the-art electronic and computer technology for the evaluation of biologic signals obtained from isolated cells, tissues, human and animal species to aid basic research and diagnosis of medical and veterinary disease states. CVAT can be used to process biologic signals such as, but not limited to:

- The electrocardiogram in all it's forms, and in particular, the continues electrocardiographic signal such as that obtained with the Holter technique or during on-line, real time monitoring of a patient.
- The electroencephalogram
- The myogram
- The phonocardiogram
- Respiratory sound waves including their correlation with the electrocardiogram and encephalogram to diagnose sleep disorders in the hospital and in out of hospital settings, etc will be evaluated.

The invention also enables the generation of a report of the evaluation and the triggering of alarms in the real time monitoring mode.

CVAT is different from current forms of biological signal analysis in that it preserves the integrity of the analog signal, enhances dynamic range, the fidelity and resolution of the original signal obtained. All these features lead to better interpretation of the signal using compressed visual patterns, which, in turn, leads to quick and easy identification of abnormalities suggestive of pathologic states. CVAT is based on the application to biological signal analysis of advances made in the software, hardware and electronic technology used to process and analyze sound waves. This is a major departure from current obsolete ways to digitize analog signals, which include the use of extreme lossy digital compression, Fast Fourier Transformation and other mathematical and autocorrelational engineering based algorithms which markedly deteriorate the quantity and quality of the signal to be evaluated.

A main application of the present invention is to improve the analysis of the Holter electrocardiogram. The invention departs from the current Holter ambulatory electrocardiogram analysis in that it replaces auto-correlational communications engineering techniques and quantification-dependent analysis of the electrocardiogram done with obsolete computer technology which eliminates most of the original signal and distorts the fidelity, resolution and dynamic range of the small fraction kept in the digital file for algorithm driven analysis.

Instead, CVAT relies on morphologic and pattern evaluation signal analysis complemented with quantification when necessary. The totality of the signal originally recorded is preserved with protection and enhancement of dynamic range, resolution and fidelity of the signal.

The following features represent the main aspects of the instant CVAT invention, and together enable the invention to provide optimal processing and analysis of biologic waves:

- Prior to analog to digital conversion, each lead of the ECG or other biologic signal undergoes electronic enhancement of the dynamic range;
- Analog to digital conversion is done with the best possible equipment and the slowest possible play back speed of the originally recorded signal;
- An optimum quality sound card is used for analog to digital conversion using the highest possible sample (preferably 44,100 Hz per second per channel or higher) and quantization (preferably 16-bits per sample per channel or higher) rates;
- Digital sound processing software and techniques are used for the processing and analysis of biological signals. The inventor has determined that one suitable sound processing software is SOUND FORGE, which is designed for processing digital audio. Other similar software programs (such as, but not limited to seismographic and geologic software) used for wave analysis may also be used in accordance with the present invention. Such software allows various steps to be performed to enhance the signal (without introducing distortion) in the voltage and time domains and enhances pattern visualization and other forms of analysis;
- The invention preferably used file formats originally created for sound wave applications (such as, but not limited to .wav and other similar file extensions) to process the biological signals;
- Computer sound cards (such as but not limited to the Montego Bay card) are used to code and decode the analog biologic signal;
- Visual compression of the analog signal is used to display the signal with high fidelity, resolution and dynamic range to identify visual patterns used as indicators of abnormalities which can be confirmed by expanding the signal;
- Use of visual pattern libraries to train technicians with low level skills to facilitate the cost effective use of CVAT for mass screening, clinical practice and research;
- Use of time interval measurements in the biologic signal to asses internal functional harmony as a reflection of normality or pathology. Such time intervals can be measured with a precision at or below $10,000^{th}$ of a millisecond and will be even more reliable when better recording techniques are introduced. Normal standards applicable to the method used will be created to replace normal values extrapolated from data obtained with better equipment and in different circumstances. Extrapolated quantitative standards lack precision; and
- Use of screen capture software (such as, but not limited to, Paint Shop Pro) to document the findings of the analysis and to transfer the images to graphic processing programs (such as but not limited to Adobe PhotoShop). This software is used for magnification and preparation of the report of the analyses.

In accordance with another aspect of the invention, internal harmony in the duration of different intervals of the electrocardiogram is advantageously used, and relies more on relative than on absolute duration. Internal harmony is done to evaluate repolarization of the myocardial cell according to the relationship between:

- Cycle length duration measured as the J-J interval
- Total duration of ventricular repolarization measured as J-Te and related to cycle length as (J-Te/J-J) X100
- Transmural repolarization time measured as Tp-e related to the total duration of ventricular repolarization as (Tp-e/J-Te)x100

In accordance with another aspect of the invention, the method is used to detect microvolt and lesser changes in the ST segment, T wave, etc., as an indication of myocardial ischemia or electrical alternans or non-homogeneous repolarization and/or depolarization in ambulatory, cost effective conditions.

In accordance with another aspect of the invention, the method is used for evaluation of microvolt and lesser changes in the PQ interval shown as Ta changes suggestive of atrial ischemia.

In accordance with another aspect of the invention, morphologic patterns are used to detect transient or intermittent myocardial ischemia when other forms of Holter analysis are useless in evaluating recordings with artifacts, bundle branch block, ventricular hypertrophy, previous myocardial infarctions, etc.

In accordance with another aspect of the invention, morphologic patterns are used to detect intermittent atrioventricular or intraventricular blocks potentially caused by cardiac pathology such as, but not limited to, ischemia.

In accordance with another aspect of the invention, the method is used to detect traditionally minor (less than 1 mm shift in the current art) considered "non-specific" ST segment shifts as sign of important ischemia risk. This is done by correlating the ST shift to the QRS as percent of the preponderant wave of the QRS normalized to its maximum potential using the CVAT software described herein.

In accordance with another aspect of the invention, the method is used for on-line monitoring of the electrocardiogram and other biologic signals.

In accordance with another aspect of the invention, the method is used to analyze simultaneously obtained upper airway breath sounds and the electrocardiogram to detect sleep apnea at home or elsewhere.

BRIEF DESCRIPTION OF THE DRAWINGS

These and other objects, features and advantages of the instant invention will become apparent from review of the following detailed description with reference to the accompanying drawings, in which.

DETAILED DESCRIPTION OF THE PREFERRED EMBODIMENTS

Figure 1:
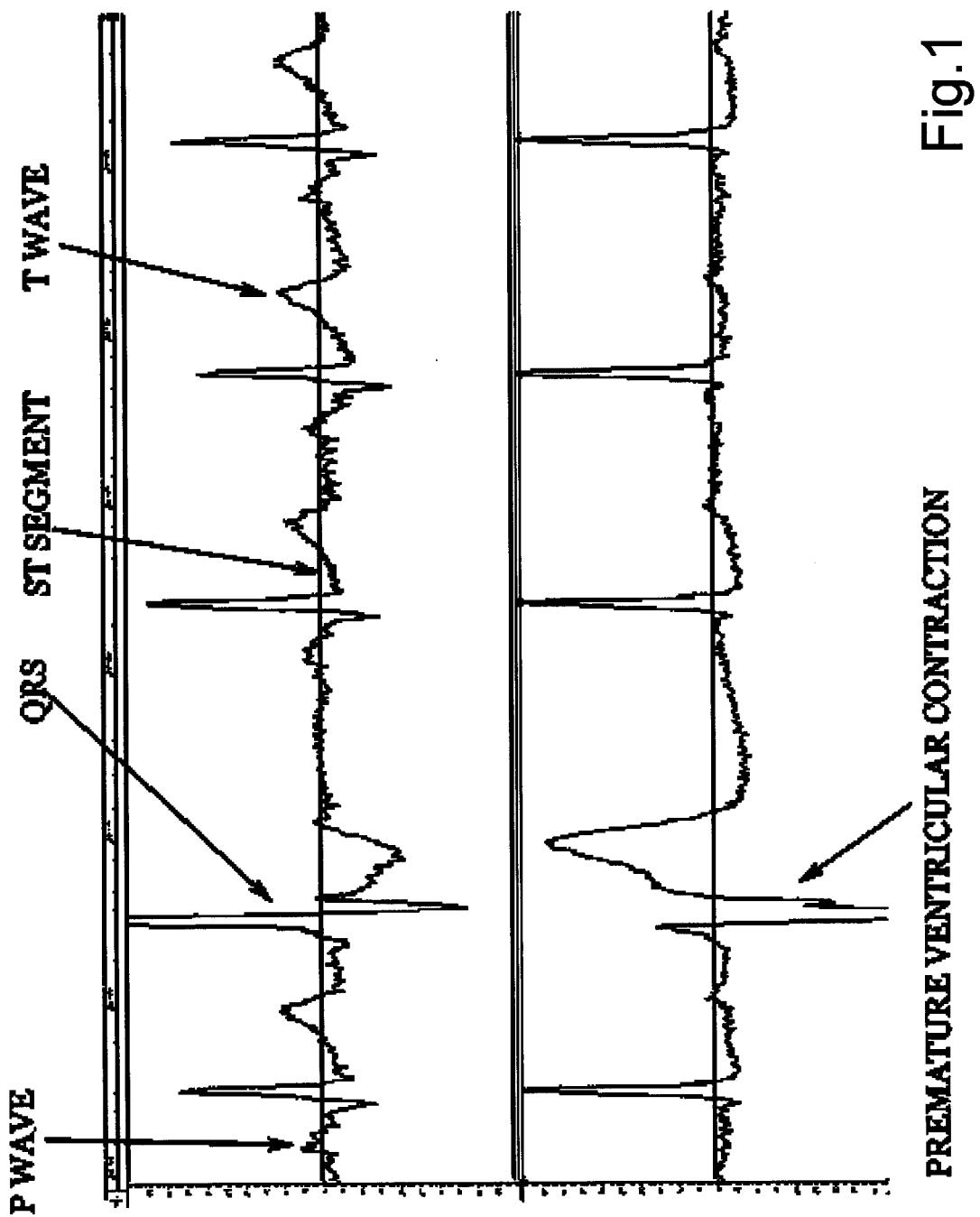
FIG. 1. Shows waves and segments of the electrocardiogram.

As described below, all the steps of the CVAT method, the electronic equipment, hardware and software used are preferably selected and devoted to the preservation and enhancement of the dynamic range, fidelity, resolution and integrity of the biological signals being processed. Compact visual analysis is done on an optimum analog signal retrieved preferably using the best possible technology. Various steps are taken to enhance visualization and facilitate analysis to aid basic research, medical and veterinary diagnosis. The quantity and quality of the signal is protected during analog to digital conversion using techniques such as: 1) independent electronic channel dynamic range modulation; 2) slowest possible play back speed of the magnetic tape; and 3) maximum possible sampling and quantization rate.

For the same reason, digital compression, smoothing of the data, filtering, Fast Fourier Transformation etc., are preferably avoided to preserve the integrity and quality of the biological signal. The CVAT methodology, electronic equipment, hardware and software used in accordance with the instant invention are preferably upgraded over time to keep pace with the fast development of signal analysis electronics and computer technology.

The following described equipment and software are preferably used when implementing the CVAT method to process and analyze the Holter ambulatory electrocardiogram.

A Denon cassette recorder model 770 R for the slow play back of the cassette tapes in which the 24 hr electrocardiogram was recorded. The right and left channel outputs of the cassette deck being connected (using high quality, well shielded RCA type cables) into the input jacks of a Stereo Sound Mixer.

A Radio Shack SSM-60 Stereo Sound Mixer, wherein the cable connected to the right channel output of the Denon cassette deck is fed into the right channel input of the CD Line 2 jack in the audio mixer. The cable connected into the left channel output of the cassette deck is fed into the left channel input of CD Line 1 in the audio mixer. The fading slider in the Audio Mixer is preferably placed exactly in the middle position to feed equal signals from Line 1 and 2 into the audio mixer output jack. High quality, well shielded RCA cables are preferably used to connect the right and left channel output jacks of the audio mixer using an RCA to mini (3.5 mm) stereo jack conversion piece into the stereophonic input of a sound card.

A high quality sound card is preferably used, such as (but not limited to) the Turtle Beach Montego A3D 64 Voice PCI Sound Card installed in a Dell mini tower. This card has greater than 90 decibels signal to noise ratio, sampling rates as high as 96 kHz per channel at 16-bit per channel digital, coder/decoder software for recording and play back of high fidelity, high resolution, high dynamic range signals. Another sound card installed in a Gateway Solo 9100 Multimedia Notebook has also been determined by the instant inventor to provide suitable functionality for use with the instant invention.

Windows 98 PC platforms are preferably used, such as a Dell Dimensions XPS R400 MHz PENTIUM Mini tower with MMX technology with 348 MB SDRAM memory and a Gateway Solo 9100 Multimedia Notebook with a Pentium MMX 266 MHz and 192 MB of RAM. It is noted, however, that any other suitable computer platform me be used in accordance with the instant invention.

In accordance with an important aspect of the instant invention, software dedicated or otherwise used for signal analysis of waves including, but not limited to, software used in w the processing of digital sound, seismography, identification of extraterrestrial radio waves, etc. is advantageously used to process the biological signal. The instant invention is applicable to the use of all different combinations of programming, mathematical analysis techniques, etc., devoted to the retrieval, storage, display, analysis, etc., of biological waves indicative of the function of any and all organs or tissues, intact or isolated from human or other biologic species. Such processing of biological waves includes retrospective (e.g. analysis of ambulatory recordings of electrocardiograms or electroencephalograms), as well as real time analysis of a stream of signals such as (but not limited to) continues monitoring of electrocardiograms or encephalograms. The CVAT method is dedicated to preserve the integrity and enhance the dynamic range, fidelity, resolution, and other important parameters of such waves.

In accordance with the invention, use of existing (and future) digital audio processing programs, such as Sound Forge XP (offered by Sonic Foundry, 754 Williamson St, Madison, Wis. 53703) and all the like sound processing and editing programs are advantageously applied to the analysis of biological waves. Sound Forge XP has been determined by the inventor to work well in connection with the method described herein. Other similar software programs for use in PC, Apple, Linux, Unix and any other computer platforms may also be used.

It is noted that Sound Forge supports an extensive set of file formats dedicated to digital audio editing and processing. Historically, almost every type of computer platform used it's own file format for audio data, some files are more generally applicable, and conversions between almost any pair of formats is possible, but losing information is a risk. The invention advantageously uses any of these or similar file formats for the specific use of biological wave analysis. Examples of some of the files which can be used are:

Active Streaming Format (.ASF)
Ad Lib Sample (.SMP)
Amiga SVX (.VSX/.IFF)
Covox V8 (.V8)
Creative Labs VOC (.VOC)
Dialogue VOX (.VOX)
Gravis Patch (.PAT)
InterVoice (.IVC)
Macintosh AIFF (.AIF/.SND)
Macintosh Resource (.SND)
MIDI SDS (.SDS)
NeXT/Sun(Java) (.AU/.SND)
Raw Files (.RAW/.*)
Real Media (.RM/.RA)
Sample Vision (.SMP)
Sonic Foundry Sample Resource (.SFR)
Sound Designer 1 (.DIG/.SD)
Sounder/Sound Tool (.SND)
Video for Windows (.AVI)
Wave (.WAV) etc The signal analysis software is used in accordance with the instant invention to code and decode (codec) the biological waves as well as to retrieve, display, process and analyze biological waves for basic research, medical and veterinary diagnosis.

The analog signal retrieved from the source is displayed, in the analog compressed (compacted) or expanded formats, using maximum fidelity, resolution, color depth and refresh rates. A cathode ray tube (Dell Computer) as well as a liquid display system (Gateway Solo notebook) were used. Both and all-future forms of compacted or compressed analog display of digital data in the fashion described herein may be used whether it is from retrospectively obtained (e.g. from any recording media) or real time signals from patients, animals, isolated organs, tissues, cells, etc.

To document and preserve findings displayed on the screen, to further magnify the signal or subject it to image enhancement, etc., a screen capture software program is preferably used, such as Paint Shop Pro 5. Photoshop 5 may be used to process the image, enhance contrast, enter legends, further magnify etc. Microsoft Word and Microsoft Publisher are preferably used for the preparation of reports to summarize the findings of the signal analysis. JPEG encoded images may inserted within the text. The above and similar programs and digital image files for the different processes needed for visual or instrumented analysis, image enhancement etc of the analog signal representing biological waves processed using digital sound or other wave technology process are preferably used. The images obtained can be printed using, for example, an inkjet Hewlet Packard Printer Model 1120C.

The CVAT method of the instant invention is designed to process and analyze biological waves using digital sound or any other computerized wave analysis software or techniques, including but not limited to the use of digital audio acquisition, editing, reproduction etc., as tools to facilitate computer aided visual as well as algorithmic and mathematical analysis. The purpose of CVAT is to enhance the use of signal analysis as an aid to basic research, medical and veterinary diagnosis. The CVAT method of the instant invention preferably includes, but it is not limited to, the following sequential steps:

Transferring the analog signal from the original media into the computer hard drive. This is preferably done using the best possible electronic equipment, enhanced dynamic range and optimum play back speed.

Using computer software for high sampling and quantization rates (at least 44,100 Hertz at 16 bits per sample, per channel where the sampling rate is the number of frames per second), to preserve the dynamic range, integrity, fidelity and resolution of the analog signal encoded in the original recording media.

Allocation of optimum amount of computer memory to preserve the integrity, dynamic range high fidelity and resolution of the signal. Digital compression algorithms, filtering, smoothing or any other signal deteriorating or diminishing manipulation likely to compromise the integrity, fidelity, resolution and dynamic range of the original analog signal are preferably avoided at all times.

CVAT is preferably done with the high quality hardware (codec chips, etc.) and software to code and decode the analog signal to recover and display it in a high fidelity-high resolution mode in a computer monitor at or above 1600×1200 pixels with 32-bit color and high refresh rate.

CVAT is preferably done using a high quality computer system to magnify waves in the X and Y-axes. Magnification along the X and Y-axes is done to allow precise measurement beyond microvolt and microsecond levels to facilitate visual morphologic analysis in the compressed or expanded modes. Enhanced resolution, fidelity and dynamic range further facilitate detection of morphologic changes of biologic waves such as the ECG, encephalogram, myograms, etc. Since its discovery at dhe beginning of this century, electrocardiography has been a visual pattern recognition discipline. Computers can be used to facilitate such pattern recognition but in final analysis trained technicians are still superior to computers to discriminate normal from abnormal patterns.

Use of high quality programs for screen capture and further image processing of selected representative portions of the recordings is also an integral part of CVAT.

Each of the above-mentioned steps will be described in greater detail below. The caveat is that keeping pace with the fast improvement in electronic equipment, computer hardware and software, the tools and techniques used in each step of this method will continue to improve and translate technologic advances to the benefit the different patient populations served by CVAT. For instance, 24-bit quantization as well as 192 kHz sampling rates are envisioned to soon become an integral part of the CVAT technology.

The invention may also employ Direct Stream Digital (DSD) technology for the analysis of biological waves for basic research, medical and veterinary diagnosis. DSD uses Delta Sigma modulation to generate a bitstream that represents the analog signal being recorded. Instead of sampling the signal at a particular instant determined by a converter clock, the DSD converter does something quite different. It keeps the previous sample in memory (actually in a feedback loop, since the system does not record signal levels) and monitors the waveform as it continues to change. If the signal value is higher than that of the previous sample, the converter records a one, if not, it records a zero. In this manner, full positive signals are represented by a string of 1's and full negative signals by a string of zeros. Silence (or the isoelectric line in the ECG or EEG) is represented by alternating ones and zeros. It is not linear pulse code modulation. The density of the pulses represents the instant amplitude of the signal. Since DSD is not organized into 16 or 24 bit samples, DSD simply records the bitstream itself and it is and looks "analog-like". DSD claims 120 dB signal-to-noise ratio through what is known as noise shaping. The DSD analog/digital converter uses 64 times oversampling achieving four times the density of current music CDs recorded at 44,100 Hz and 16-bit quantization. This technology will allow simultaneous processing and analysis of up to 72 channels (signal streams) for use in CVAT analysis of electroencephalograms and 12-lead electrocardiograms.

The invention is, for example, applicable to analysis of 24 hours ambulatory electrocardiograms recorded with current art Holter technology. The CVAT Holter analysis aims to find classically described electrocardiographic signs compatible with silent, atypically symptomatic or symptomatic ischemia, a major cause of morbidity and mortality. Detection of Risk for lethal arrhythmias is also improved by CVAT. lschemia is probably the most common cause of lethal arrhythmia and sudden death. Hence, electrocardiographic signs of increased risk of serious arrhythmia (such as depolarization and repolarization heterogeneity and preservation of the within patient harmony of the repolarization periods) are described herein. CVAT may also be used to detect increased risk of arrhythmia and sudden death in patients with congestive heart failure (CHF).

Cassette format magnetic tape is still the most commonly used media to record the ambulatory electrocardiogram from leads attached to a patient. To facilitate 24 hr recording without changing cassettes, the tape transport speed is slowed to 1.1 or 0.55 mm (depending on the manufacturer) per second instead of the 55 mm per second used to record music or other sonic waves. Differently from current Holter analysis and to preserve the quality of the analog electrocardiographic signal, CVAT technology uses as-slow-as-possible play back speeds. As described above, a Denon cassette deck model 770 R that normally plays back at 47.6 mm per second may be used. This model has variable play back speed. For CVAT, the slowest play back speed is preferably used at a transport tape rate of 40.4 mm per second. Hence, Holter tapes recorded at 1.1 mm per second are preferably played back at 36.7 times real time. In CVAT, slow play back speed is an important step in the preservation of the fidelity and resolution of the signal during the analog to digital conversion of the file. The slow speed used in CVAT should be compared to the much faster play back speeds used in current Holter analysis to accelerate analog to digital conversion despite deterioration of the signal quality. Current Holter analysis play back speeds between 60 and 480 times real time, 240 and 480 times real time are probably the most common play back speeds.

CVAT preferably uses 44,100 and 96,000 Hz-16 bits per channel as the standard sampling and quantization rates. At 44,100 sampling rate, a single sample is taken every 0.000023 seconds of clock time. A 24 hr Holter recording (more than 100,000 heart beats) is digitized by conventional art using, at best, 8,000 Hz samples per second followed by drastic lossy compression schemes that reduce the digital file to about 1.2 megabytes. The same file is encoded by CVAT in 350 megabytes, using 44,100 Hz, 16-bits quantization and no compression schemes. This 1.2/350 ratio in the richness of the digital file is a reflection of the difference in sampling and quantization rates, tape play back speed, and the use-no use of "lossy" digital data compression.

The sampling rates used by current Holter analysis are frozen in the early 90's and are, at best, 8,000 samples per second of clock time. When fast play back speed is factored in, the result is about 33 samples per second recorded time if the play back speed is 240 times real time. In CVAT at sampling rates of 44,100 or 96,000 Hz there are 1,188 to 2,376 per second of recorded time respectively.

Even the recently introduced flashcard technology is subjected to the artificial limitations imposed by the desire to transmit compressed data over telephone lines. An ambulatory recording system with 500 samples per second, 10 bits per sample, three channels, and 24 hours recording, requires the storage of about 162MB. To accommodate this data on a 20MB flash memory card requires a compression ratio of 8:1 or higher. However, the perceived need for transtelephonic transmission limits the flash card files to about 8-MB which require more drastic compression schemes and/or 8-bit quantization. The signal retrieved is still incomplete and of poor quality.

Conversion of the analog signal to digital format is a crucial step which determines the final quality of the signal preserved for analysis. Neither the magnetic cassette play back speed or the sampling rate undergo modulation to compensate for acceleration of the heart rate which are likely to happen during the recording period. The number of digital samples per heartbeat of the ECG can be referred to a normal heart rate of 60 beats per minute or one heart beat per second of recorded time. The table below compares the number of digitally sampled points per heart beat using current Holter analysis art at different play back speeds and CVAT at two different sampling rates

|  | SAMPLES PER SECOND | PLAY BACK SPEED | POINTS PER HEART BEAT* |
|---|---|---|---|
| CURRENT ART | 8000 | 240 × REAL TIME | 33 PER HB |
| CURRENT ART | 8000 | 480 × REAL TIME | 16.6 PER HB |
| CVAT | 44,100 | 36.7 × REAL TIME | 1201.6 PER HB |
| CVAT | 96,000 | 36.7 × REAL TIME | 2615 PER HB |

*Digital data points available to reconstruct one ECG cycle length (one heartbeat) at 60 beats per minute In the time domain, at 60 beats per minute, the current Holter art has, at best, only 2.7% of the sampling points of the lowest CVAT rate (33 vs 1,201 points per heartbeat). The fastest (and probably most common) sampling rate used in the current Holter art has only 0.61% of the time points CVAT offers (16.6 vs. 2,615). Hence, starting with the analog to digital conversion and prior to any of the other data degrading steps, the current art deletes between 97.3 and 99.39% of the signal encoded in the magnetic tape. The data loss increases with increasing heart rate. If the heart rate goes from 60 to 120 per minute, only one half of the above points will be converted from the analog to the digital format and enter the computer file. For the current Holter analysis, this loss happens prior to further signal degradation due to lossy compression, replacement of real for imaginary points (through Fast Fourier Transformation), filtering, etc which is not the case when CVAT is used. This data elision is compounded by the current Holter analysis use of 8-bit instead of 16-bit cards. Quantization with 8-bit cards gives only 0.39% (256 points per channel) of the voltage resolution afforded by 16-bit cards (65,536 points per channel). This calculation does not include the signal deteriorating effect of failure to do independent control of dynamic range prior to digital conversion.

The importance of quantization rate and independent channel gain control for the preservation and enhancement of dynamic range will now be described. It is being increasingly recognized in electrophysiology of the heart that microvolt level and lesser magnitude voltage changes encode very important diagnostic and prognostic information. Current computerized Holter analysis sacrifices dynamic range, fidelity and resolution to high-speed analog to digital conversion and the need to fit the 24 hr signal in a small digital file to facilitate telephonic transmission. It is well known that lack of dynamic range affects foremost the lower voltage changes in the signal. If dynamic range is not optimized prior to digital encoding of the analog signal, the range of voltage describing points above and below the isoelectric line is not fully utilized; hence the ST-T changes in the ECG are less apparent. A primary difference between CVAT and the conventional art is that CVAT strives for the preservation and enhancement of the dynamic range to facilitate identification and interpretation of microvolt and lesser voltage changes used to detect ECG signs of potentially lethal conditions. Independent channel modulation of the dynamic range, slow tape play back, high sampling and quantization rates achieve optimum storage, recovery and display of microvolt range signals. CVAT is preferably done with 16-bit quantization rate, but 24-bits and higher may also be used. The signal to noise ration at 16-bits per sample and 44,100 Hz is about 90 dB. Current Holter analysis use of 8-bits quantization drops the signal-to-noise ratio to 40 dB or less. Noise is known to induces more interference in the quieter periods in music and around the isoelectric line and the ST-T region of the ECG. Signal smoothing and filtering done in current Holter analysis further deteriorate discrimination of microvolt range changes in the signal.

In CVAT independent electronic gain control is possible because morphologic analysis relies on the internal harmonic relationship of the electrocardiographic waves and relative rather than quantitative changes in the signal. Microvolt measurement in current Holter analysis is based on numerical conversions using voltage calibration (1 millivolt=10 mm deflection) signals which often are faulty and hence unreliable. In CVAT, independent electronic gain is adjusted in order to use the Y-axes to it's full extent with the QRS deflection as (or near) 100% of it's potential height. This is done to expand the dynamic range and to obtain the greatest possible benefit of the 16-bit quantization rate. By optimizing dynamic range prior to digital conversion, as much of the potential 65,536 points available per channel in the Y-axes are used. High dynamic range and resolution in the Y-axes facilitates evaluation of microvolt and lesser voltage changes in the ECG. These steps are essential for the detection of ischemia and arrythmogenic risk. Current Holter analysis does not optimize dynamic range prior to digitizing at 8-bits per sample, these results in only partial use of the 256 points provided by 8-bits in the Y-axes. Hence, the effective difference in dynamic range preservation and voltage resolution between the conventional art and CVAT is well beyond 65,536/256. Hence, the current Holter quantization has 0.39% of the resolution offered by CVAT quantization rate. Additionally, during CVAT analysis a voltage optimization (VO) bit interpolation process can be used to magnify the Y-axes. Voltage optimization can be applied to selected regions of the visually compressed file, individual heartbeats or selected waves within it. Voltage optimization takes the selected part of the signal to 100% of it's potential above or below the isoelectric line. In the current electrocardiographic art, reliable detection of microvolt changes is confined to costly and time consuming techniques such as signal averaging done in the electrophysiologic laboratory and not useful for mass screening or applicable to Holter analysis. Detection of certain types of microvolt changes is valuable as tool to identify serious risk for arrhythmia. Such changes are usually more evident at times of physical and/or emotional stress. Ambulatory detection of microvolt changes, applicable to mass screening is now made possible by CVAT and should result in major improvement in cardiovascular diagnosis for prompt intervention and important reduction of mortality and morbidity.

Current Holter analysis relies upon signal amplitude (voltage) calibration done prior to recording by introduction of a 1 millivolt signal directly into the magnetic tape. In theory this calibration signal should be equal in both channels and should render an even 10 millimeters deflection when visualized in the electrocardiogram. If all goes well, a 1 mm (0.1 mV) shift of the ST above or below the isoelectric line is to be taken as an electrocardiographic sign of ischemia. This concept is a direct extension of the very long experience with exercise tolerance testing done with stationary 12-lead electrocardiographs, more precise instruments than the average Holter recorder. In 12-lead electrocardiographs, the electronic gain can be adjusted at the time of calibration. In current Holter art, gain adjustment in the recorder is not possible. The Holter recorder calibration signal frequently has significant variation within and across recorders and it does not give as reliable conversion factor for microvolt evaluation as the 12-lead electrocardiographs.

Figure 2:
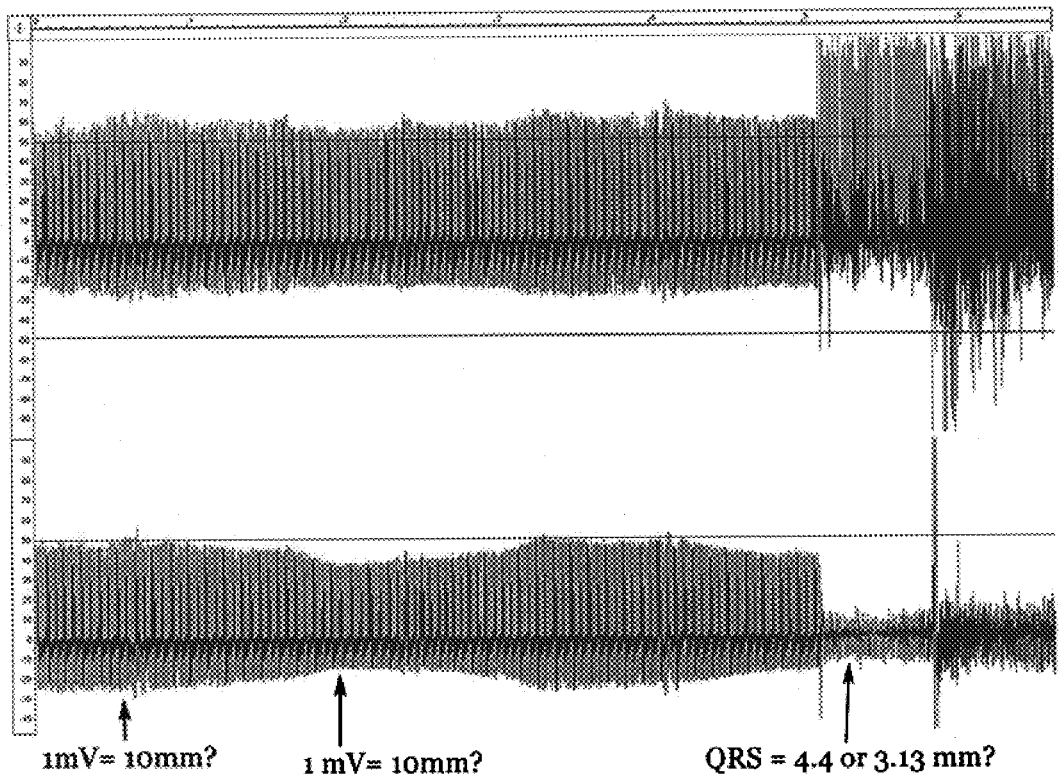
FIG. 2. Shows inaccuracy of the voltage calibration signal in current Holter recordings.

FIG. 2 shows an example of uneven calibration signal in a Holter recording. The size of the QRS voltage in the lower lead could be 4.4 or 3.1 mm depending on which part of the calibration signal would be chosen to represent 1 millivolt as a 10 millimeters deflection.

Figure 3:
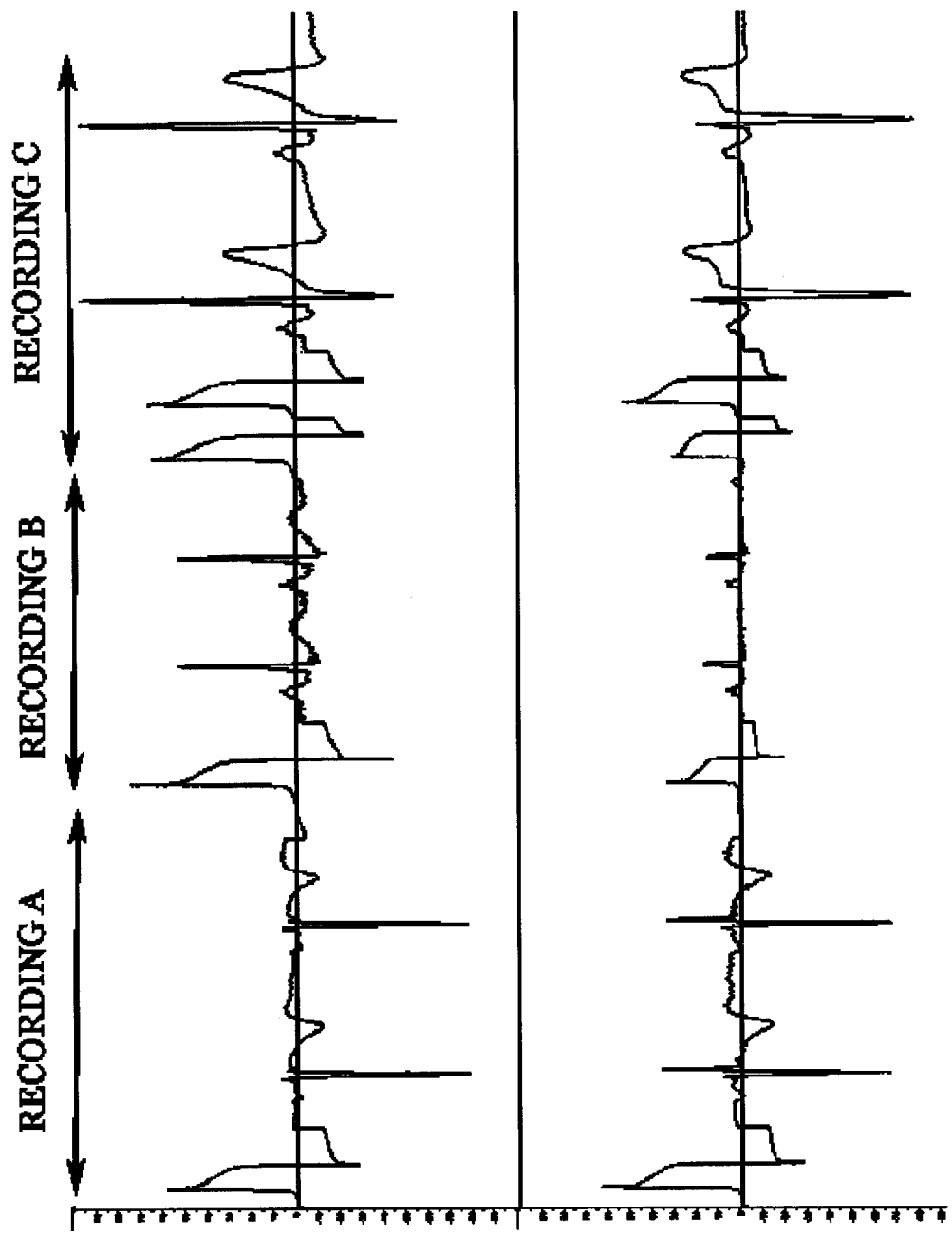
FIG. 3. Shows examples of voltage calibration differences across and within Holter recordings.

FIG. 3 shows the difference in the size of the calibration signal obtained from 3 different recordings, also note the difference in the height of the signal in the lower channel of Holter C.

Reliance on the calibration signal to quantify the severity of microvolt range changes around the isoelectric line is not as precise and useful in Holter recording as it is in 12-lead electrocardiography. Conversion based on unreliable calibration hampers within and most importantly across patients comparisons. Furthermore, the voltage of the electrocardiographic waves does not remain constant during the 24 hr Holter recording period. Voltage changes may be due to physiologic (e.g. positional, respiratory cycles, etc) as well as pathologic reasons (ventricular distention and mechanical incompetence of the ischemic ventricle is an important reason for change). Under these conditions, absolute quantification of the ST segment, using the calibration signal as valid gage, may lead to erroneous conclusions. This is probably a reason for the poor performance of current Holter analysis in detection of myocardial ischemia.

Figure 4:
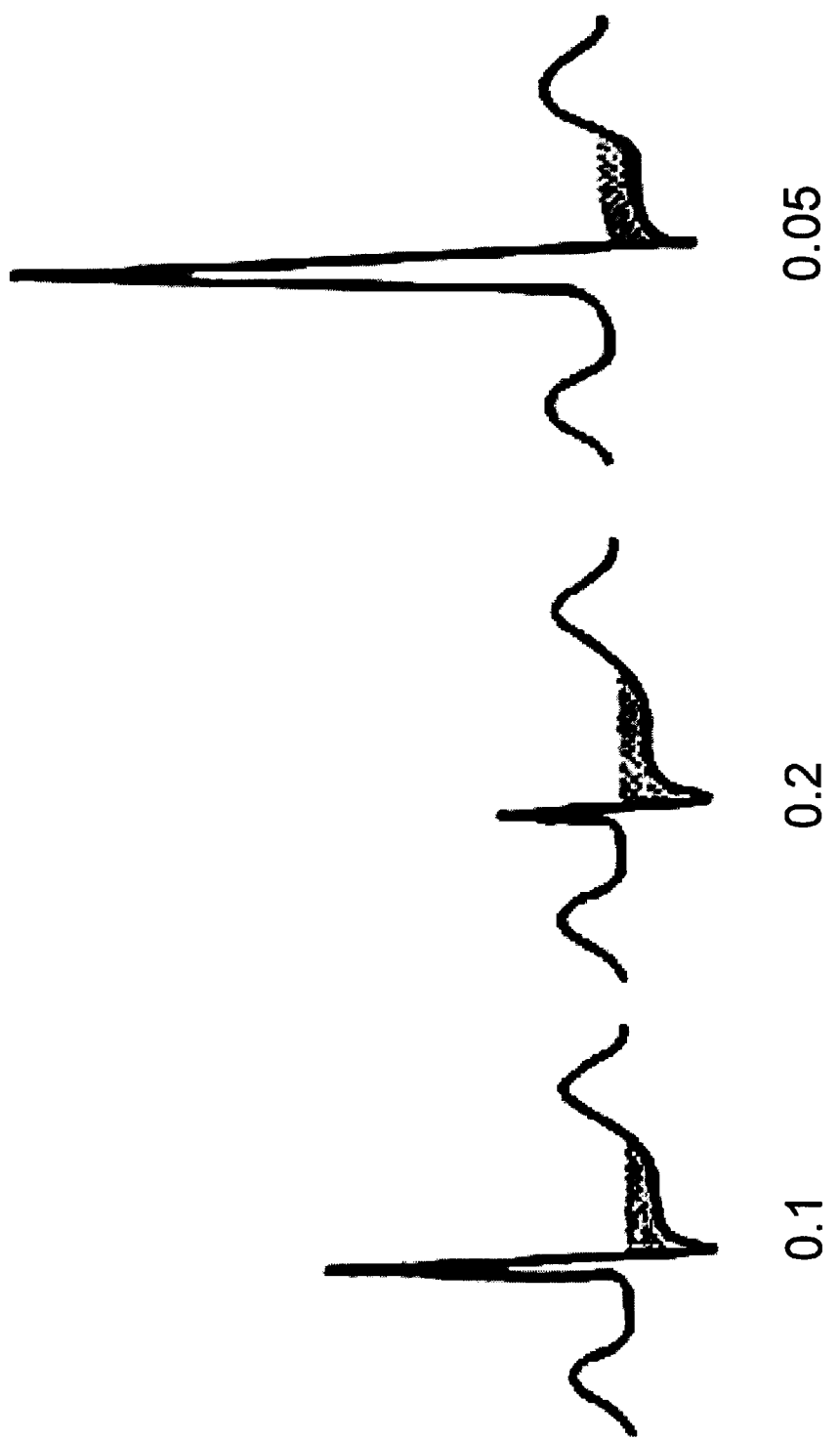
FIG. 4. Shows evaluation of ST segment shift as percent of the QRS.

More than 20 years ago, Marvin Ellestad M. D. called attention to the importance of judging ST segment shifts as a percent of the QRS in the same heartbeat. This work has been recently quoted in Ellestad M; American College of Cardiology Educational Highlights; Summer 1998: 15–21 from which FIG. 4 was taken. This figure is used by Ellestad to emphasize the importance of describing ST segment deviation as a percent of the major deflection in the respective QRS. Ellestad observation is the product of intensive and classic work in exercise stress testing done with 12 lead electrocardiographs, better and more reliable instruments than Holter recorders. Ellestad suggested 10% shift of the ST as the cutoff point for the diagnosis of ischemia. However recent data ("Association of Nonspecific Minor ST-T Abnormalities With Cardiovascular Mortality", Daviglus M. L. et al. JAMA. 1999; 281:530–536) indicates than even lower degrees of ST shift are likely to carry increased risk of mortality and morbidity. In CVAT voltage changes are evaluated as percent of the dominant spike in the QRS deflection for which voltage is optimized to 100% of it's potential. Using CVAT, non-cardiology trained technicians can detect ST segment shifts as small as 2% of the QRS.

The CVAT methodology for detection of myocardial ischemia using ST segment shift will now be described. Evaluation of the ST segment in isolation leaves most of the repolarization events out of diagnostic consideration with consequent loss of valuable information. Most of the epicardial, and all the endocardial and mesocardial repolarization data are not encoded in 60 to 100 milliseconds of the ST segment adjacent to the J point. To be able to properly evaluate the T wave in the standard 12 lead ECG, it is necessary to increase the paper recording speed from 25 mm per second to 100 mm per second. The voltage gain must be doubled to inscribe 1 mV as a 20 mm deflection using a well maintained and calibrated electrocardiograph. ECG recordings done in this manner have enough detail to visualize all the repolarization nuances, especially, T wave morphology.

Current computerized Holter analyses compares only two 8-bit points. One 8-bit point in the ST segment (placed 60 to 100 ms beyond the J point) is compared to an 8-bit point in the PQ segment which is taken to be the isoelectric line without regard or correction for the presence of atrial ischemia (Ta). This is done with strict quantitative adherence to the 1 mm shift (compared to the calibration signal)

concept derived from 12-lead electrocardiography. Current Holter analysis considers less than 1 mm shift as being normal, this results in a high rate of false negative Holter reports when algorithm analysis is not compared to visual analysis of the analog signal by expert cardiologists. Current computerized Holter analysis does not do morphologic evaluation of the T wave. In current Holter analysis the digital ECG file is not a complete and accurate representation of the originally encoded analog signal. To properly evaluate the ST segment and the T wave it is imperative to have a high fidelity and resolution signal with optimum dynamic range. The ECG signal recovered by CVAT has enough detail in the microvolt region to render precise details for accurate evaluation of all the ECG. Current Holter algorithms lack detail in the data stored and do not have the means to render a faithful depiction of the T waves recorded in the magnetic tape.

In Holter analysis, unreliable voltage calibration and unexpected voltage changes during the recording render the 1 mm shift at one point in the ST segment a handy but imprecise extrapolation from 12 lead electrocardiography. It will be a major improvement to evaluate the ST segment shift as what it is, a line, and not a single point as current algorithms do. The extent of the shift from the isoelectric line is best described as a percent of the largest voltage element of the QRS, as proposed by Ellestad more than 20 years ago. CVAT is able to do a thorough evaluation of the ST segment and complement it with a complete morphologic evaluation of the T wave, a major index of myocardial repolarization. CVAT can quickly identify shifts as small as 2% above or below the isoelectric line. Traditionally, minor changes in the ST segment and the T wave have been dismissed as "non specific" and without prognostic or diagnostic importance. However, recent data ("Association of Nonspecific Minor ST-T Abnormalities With Cardiovascular Mortality", Daviglus M. L. et al. JAMA. 1999; 281:530–536) link these "minor" abnormalities to increased mortality risk.

Figure 5:
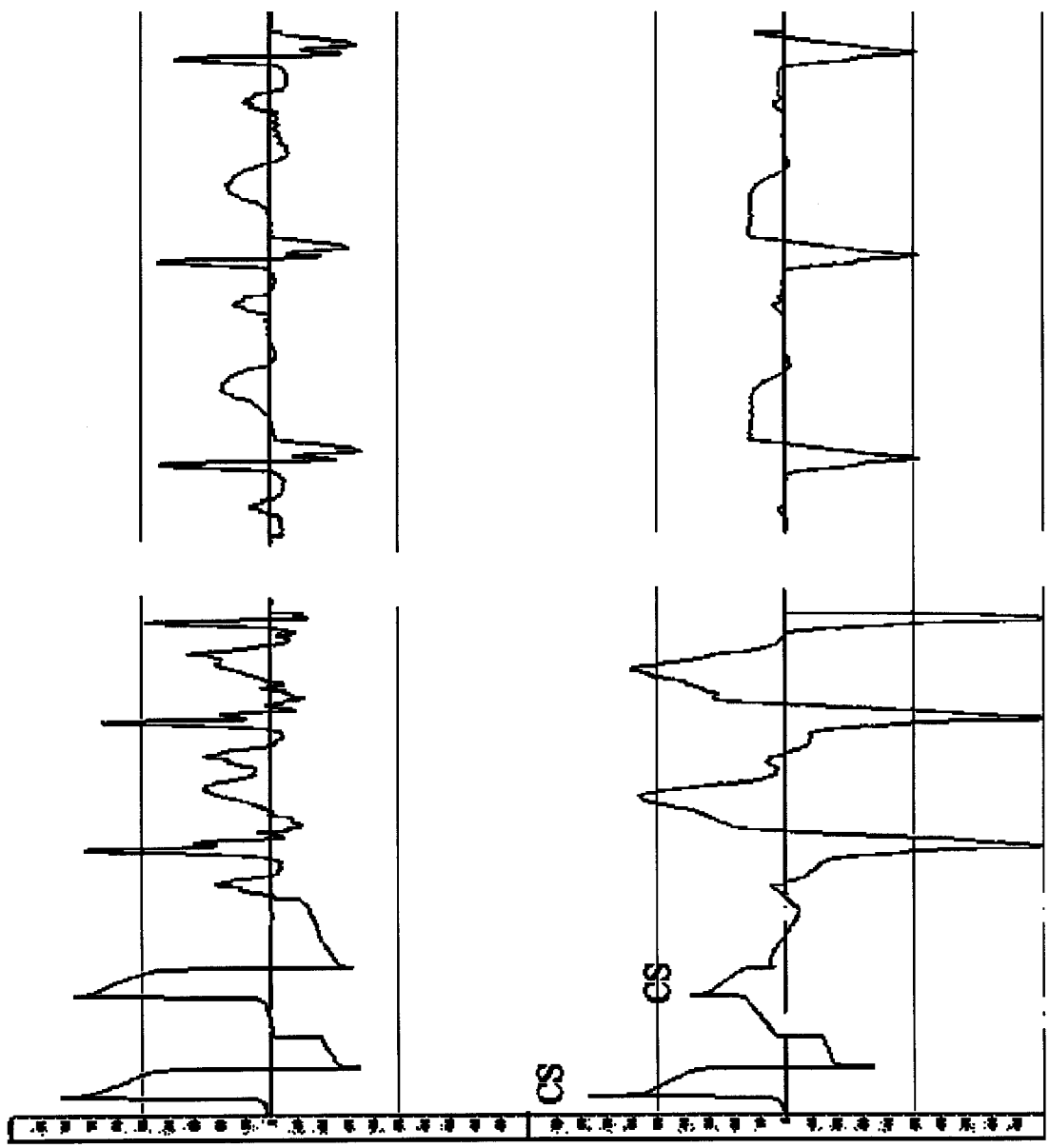
FIG. 5. Shows calibration and voltage changes during a recording.

FIG. 5 shows the difference between the $1^{st}$ and $2^{nd}$ calibration signals in the lower lead as well as the marked voltage differences found within the recording period. Quantification of the ST segment shift will depend on which complex is taken as a gage; the changing QRS voltage is another source of error. The morphology of the T wave is a valuable confirmation of abnormal repolarization which is not used by current computerized Holter analysis. The recording from which this figure was taken was not processed with voltage or dynamic range optimization.

Figure 6:
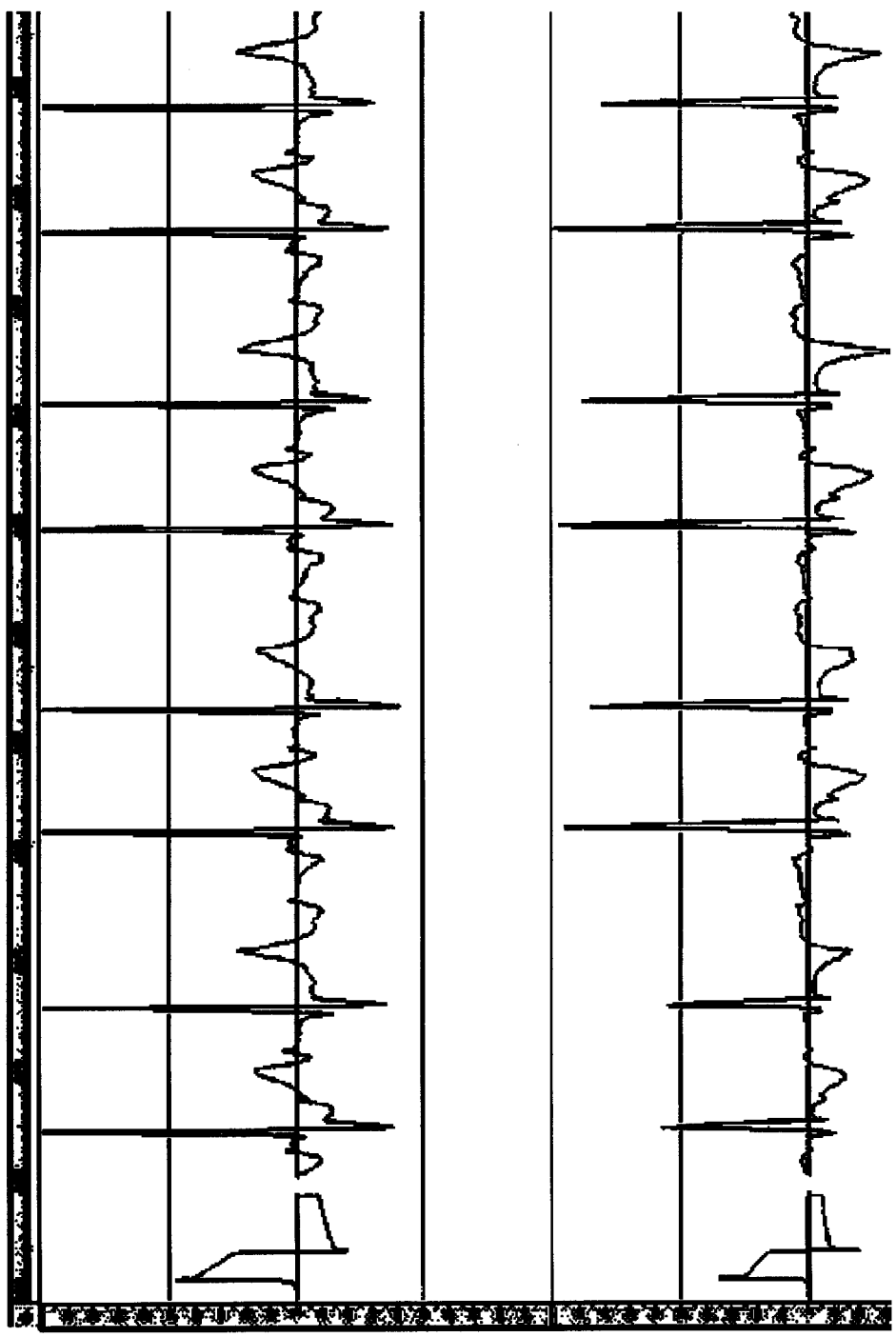
FIG. 6. Shows examples of voltage optimization in a recording done without enhancing the dynamic range.
Figure 7:
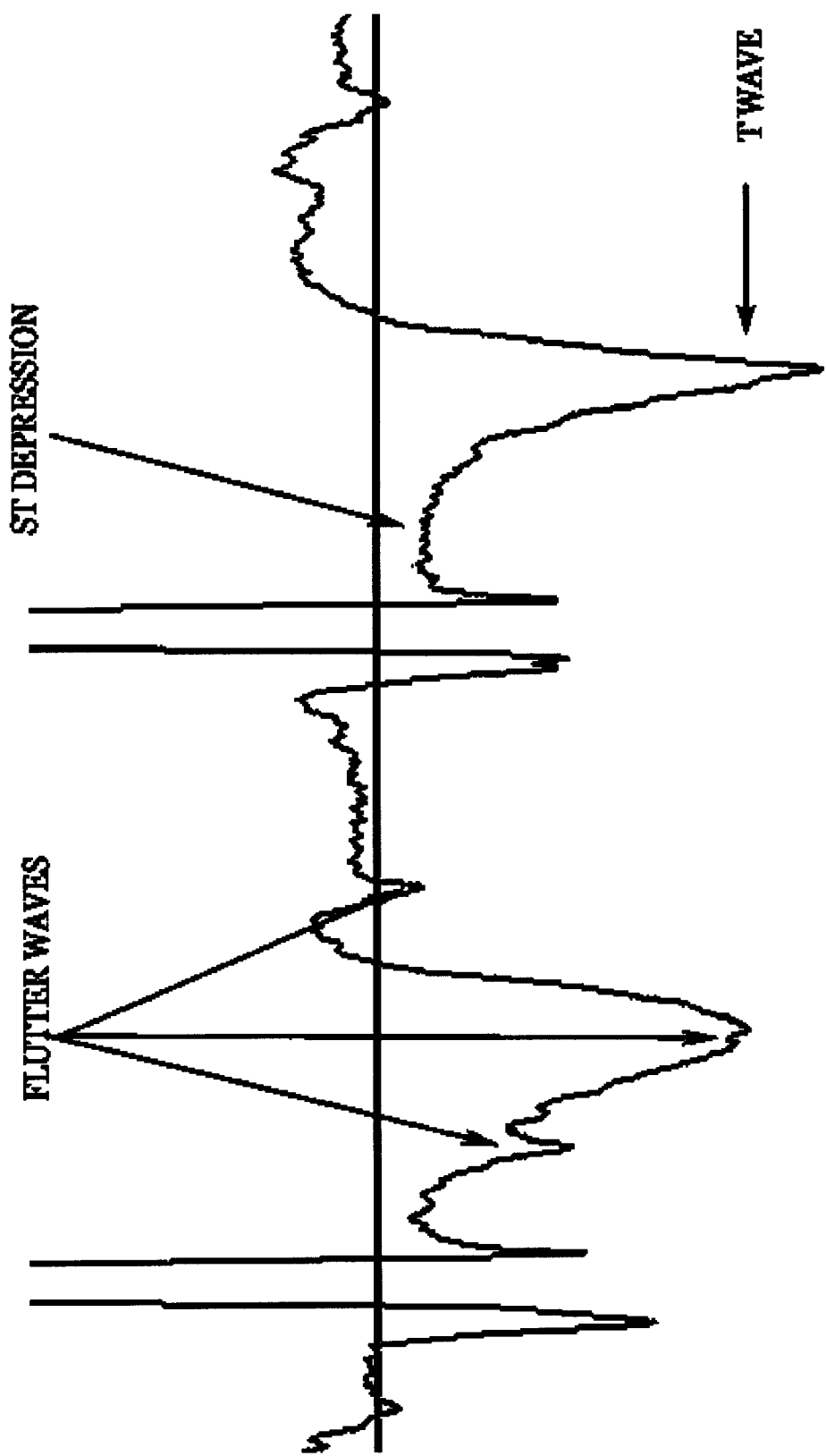
FIG. 7. Shows an expanded view of FIG. 6 to show visually identifiable electrical alternans.

FIG. 6 show a minor example of the advantage of voltage optimization in a recording digitized without optimizing dynamic range. In FIG. 6, a "minor" (less than 1 mm) ST segment depression in the lower lead becomes evident and important after the signal is voltage optimized in the lower lead. Current Holter analysis would consider this to be a non-diagnostic ST shift. The morphology of the inverted T wave, which has a fast inscribing initial limb that makes it symmetric and arrow-point-like (best seen in alternating beats), validates the ischemic nature of the ST depression. The alternating morphologic difference (arrow point like versus slightly rounded top) in the T waves is suggestive of repolarization heterogeneity probably due to ischemia. Two consecutive voltage optimized T waves from the lower lead are further magnified in FIG. 7. In this figure, the ST shift is more evident in the second beat and the morphologic differences in consecutive T waves are obvious. Flutter waves are seen as the downward small spikes going down from the isoelectric line. Detailed morphologic analysis of a high fidelity enhanced quality signal is possible with CVAT and impossible with conventional Holter algorithms. With CVAT, much greater degrees of magnification than shown above are possible if necessary.

Figure 8:
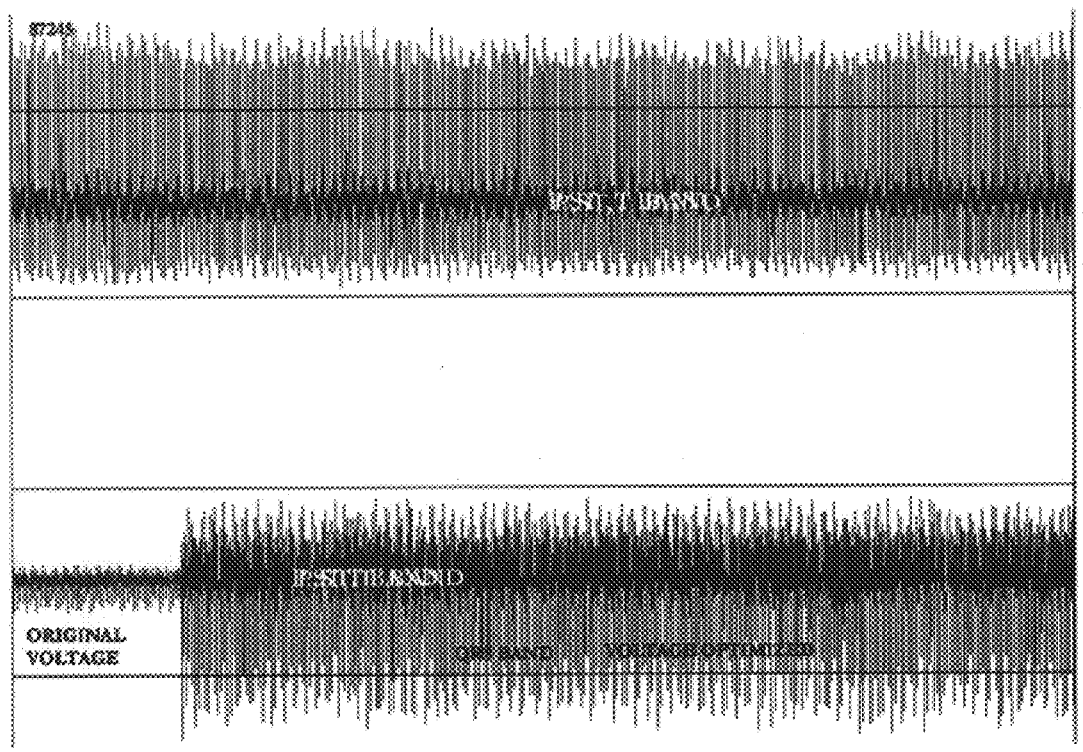
FIG. 8. Shows visually compressed CVAT pattern to illustrate normal elements thereof.

The visual compression and morphologic evaluation of the ambulatory electrocardiogram will now be described. CVAT visual analog signal compression is a powerful tool to expedite and add precision to Holter analysis. FIG. 8 is CVAT's visually compressed pattern of a normal ECG tracing showing the different components of the compressed signal. This recording was done without optimizing the dynamic range prior to analog to digital conversion. Most of the lower lead has been voltage optimized and it shows the difference CVAT does when applied to a recording done without independent channel modulation of the dynamic range. Normally, the P, PQ, J, ST, T and TP (PT band) are superimposed to each other to form a solid band in the middle of the visually compressed analog signal. The QRS band surrounds the PT band as a lighter component where the individual heartbeats can be seen. The density of the QRS band increases and decreases with increasing and decreasing heart rates respectively. The QRS also shows the regularity or irregularity of the heart rate in characteristic patterns which allow quick recognition of a single heart beat blocked (dropped). Pathology such as intermittent conduction defects, sick sinus node (tachy-brady) syndrome atrial flutter, fibrillation, etc have distinctive patterns in the QRS band. The best rate of visual compression depends on the sampling rate and heart rate. It ranges between $\frac{1}{64}$ to $\frac{1}{256}$. The lowest rates of compression works best when the heart rate is fast or when the sampling rate is low and vice versa. Expansion of the pattern in the window with resampling to higher rates or limitless magnification, whenever necessary, allow precise identification of classic electrocardiographic signs.

Figure 9:
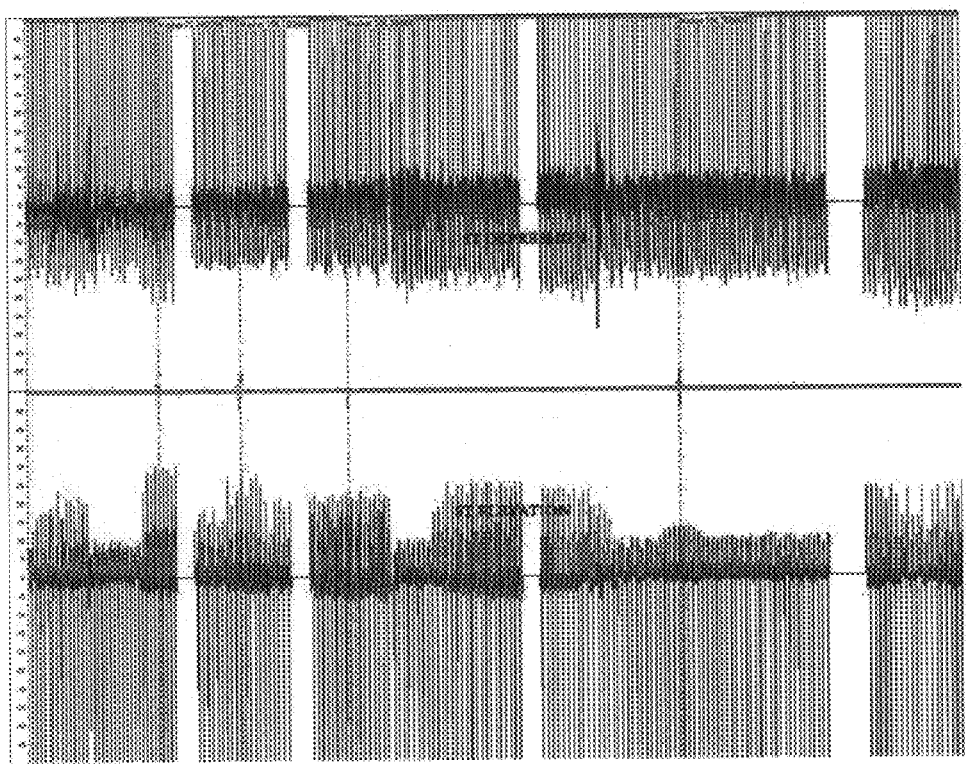
FIG. 9. Shows examples of CVAT patterns compatible with ST segment elevation and depression.

FIG. 9 is a composite of different recordings shown examples of how CVAT compressed analog displayed facilitate quick identification of ST segment shifts by technicians without biomedical training or skills in electrocardiography. The upper lead shows compact patterns of ST depression. The PT band is seen with a solution of continuity in it's middle portion. The white area which hugs the isoelectric line is composed by the PQ and portions of the T (depending on the changes in T morphology) and TP. The lower band which moves into the negative voltage area represents down shift of the J point, ST and portions of the T (depending of the morphology of the T wave). The black space separating the PT band into two diverging portions is patognomonic of ST shift. In the lower lead examples of ST elevation are collected. Notice that the arm of the bifurcated PT band which departs from the isoelectric line has moved into the positive voltage area denoting ST segment elevation. A library of patterns can be used for training technicians who will do CVAT analysis. Expansion of this tracings show the classic signs of ischemia described in the PQ for atrial ischemia and the J point to the end of the T wave for ventricular ischemia. Transient conduction blocks, which can be secondary to ischemia, also have characteristic patterns.

Figure 10:
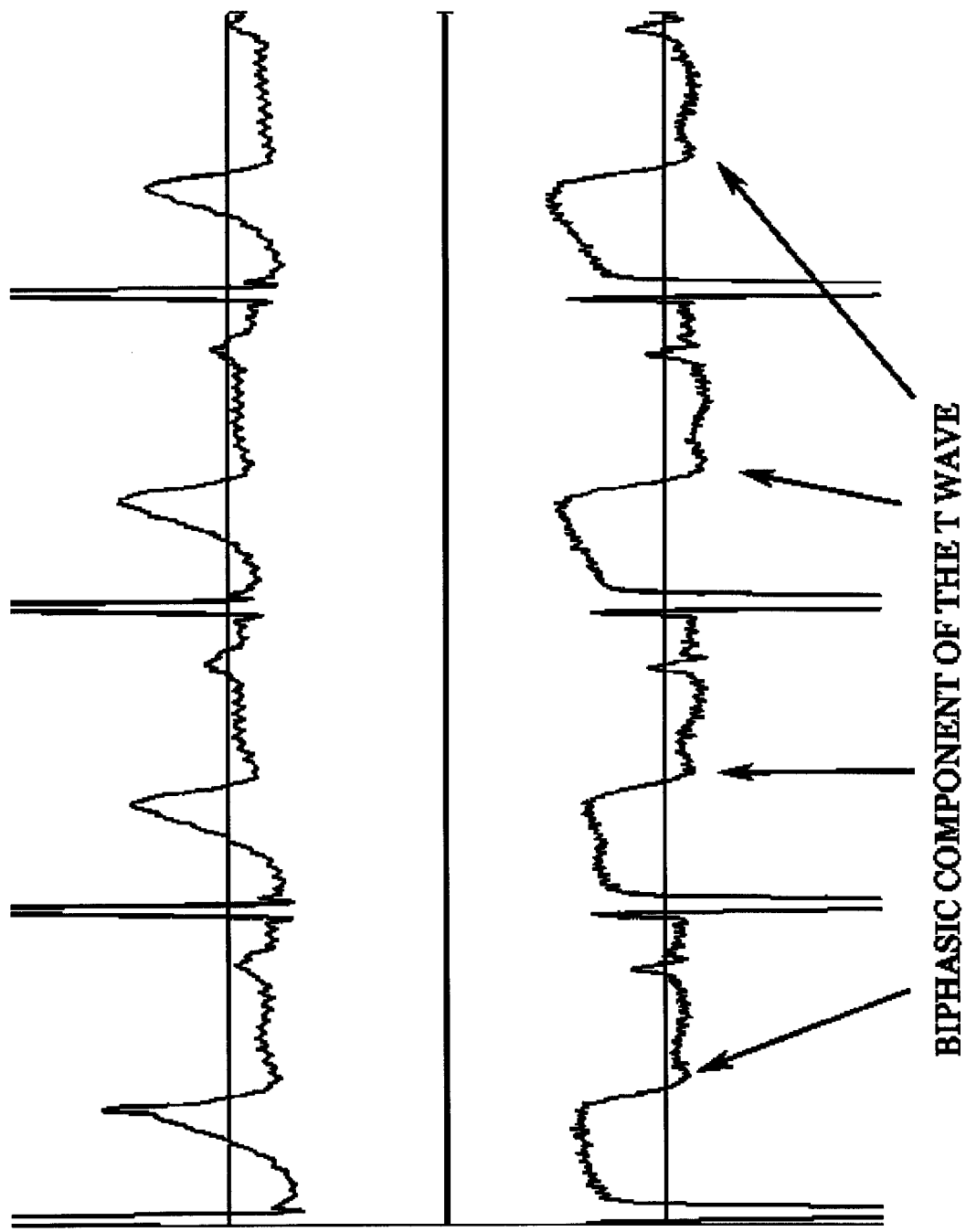
FIG. 10. Shows expanded ECG showing ST elevation and T wave changes.
Figure 11:
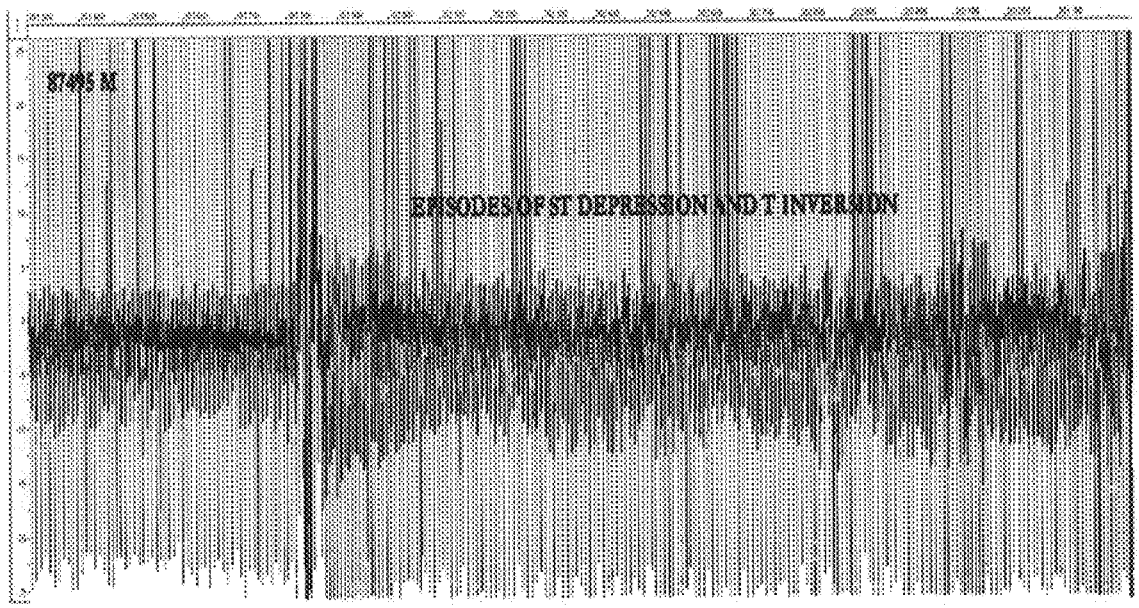
FIG. 11. Shows a CVAT pattern of ST depression and T wave inversion.
Figure 12:
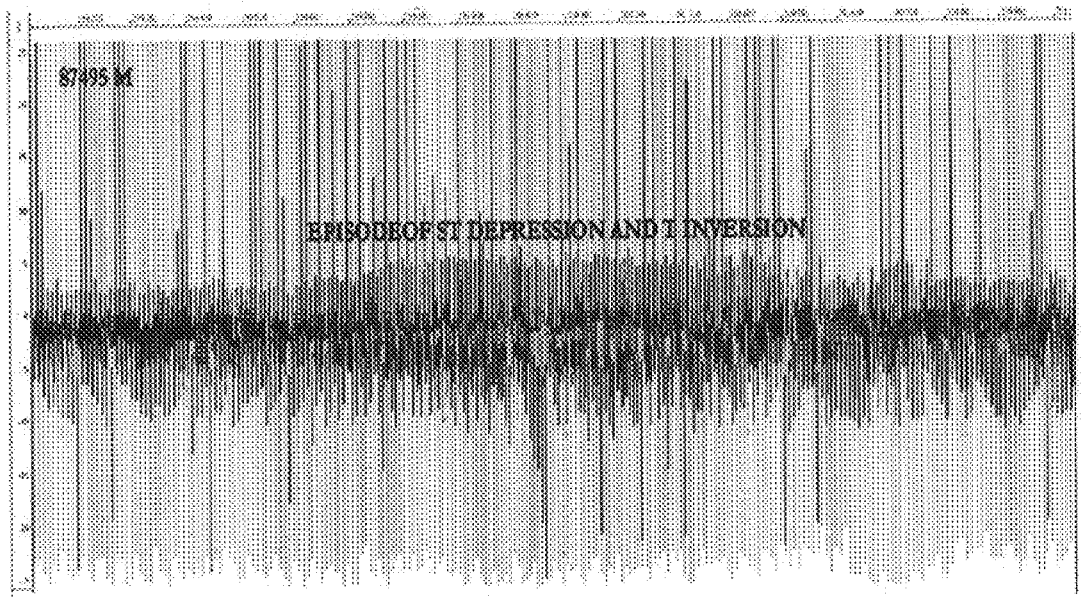
FIG. 12. Shows a CVAT pattern compatible with ischemia showing slow onset and offset of the ST shift.
Figure 13:
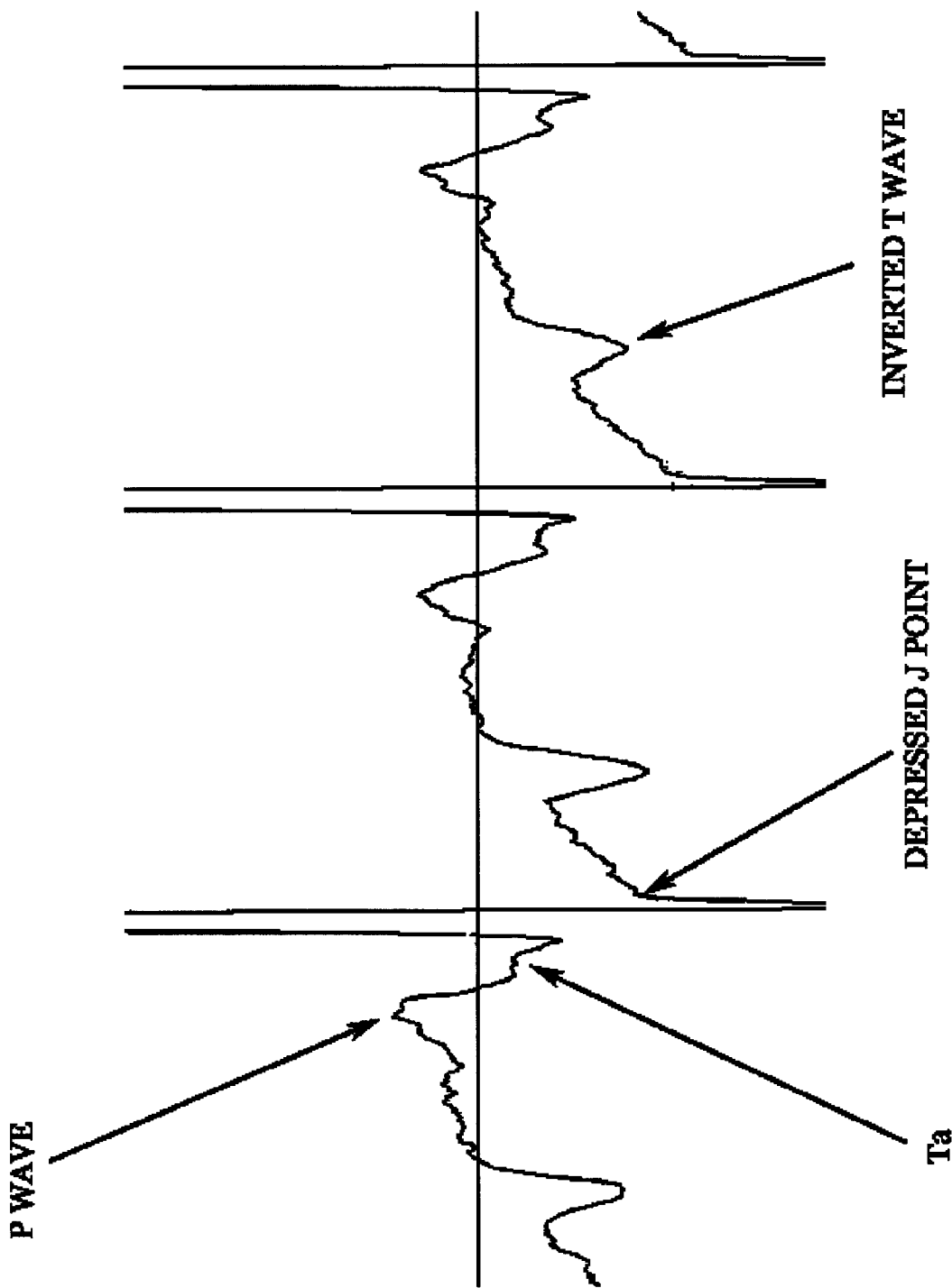
FIG. 13. Shows expanded ECG to illustrate Ta, ST depression and T wave inversion.
Figure 14:
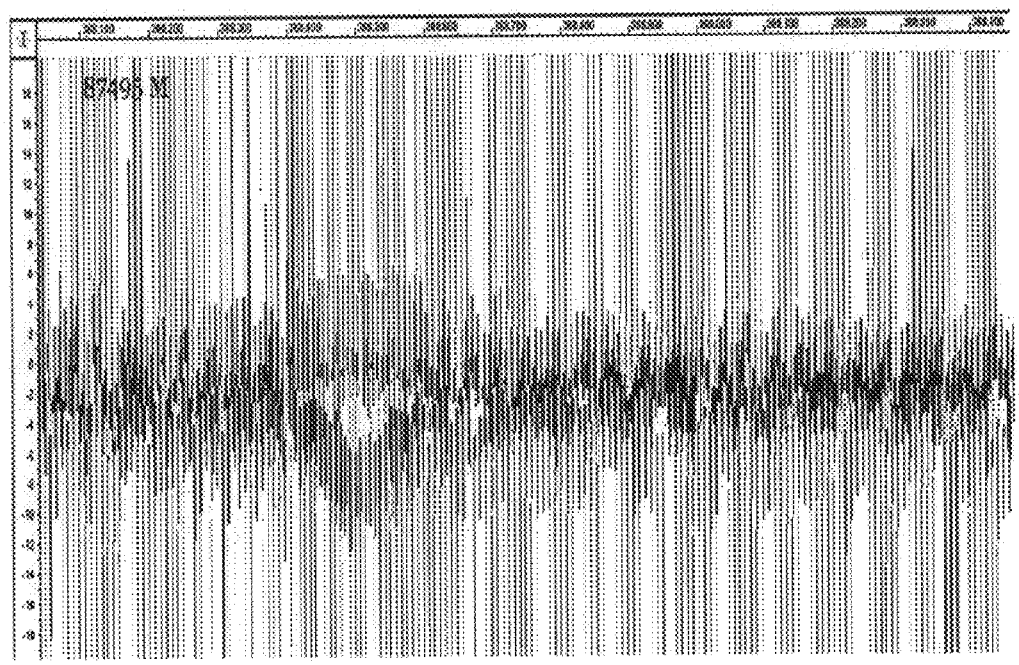
FIG. 14. Shows a CVAT pattern of brief period of ST depression.

FIG. 10 shows ST segment elevation and T wave changes in an expanded view used to confirm the findings on the compressed pattern. FIGS. 11 and 12 show visually compressed patterns of episodes of ST depression with inversion of the T wave. FIG. 11 shows best the gradual onset and offset of the ST segment shift characteristic of a true ischemic episode. FIG. 13 shows an expanded view of ST depression with inverted T wave. FIG. 14 shows a short episode of ST depression with T inversion. This episode most likely would not have been detected with conventional Holter analysis. If detected, it would have been dismissed since it does not last one minute which is a convention for acceptance of an episode in current Holter analysis. FIG. 13 also shows Ta as a sign of probable atrial ischemia. This ECG sign is not commonly seen because of the lack of dynamic range, fidelity and resolution of current ECG tracings.

Figure 15:
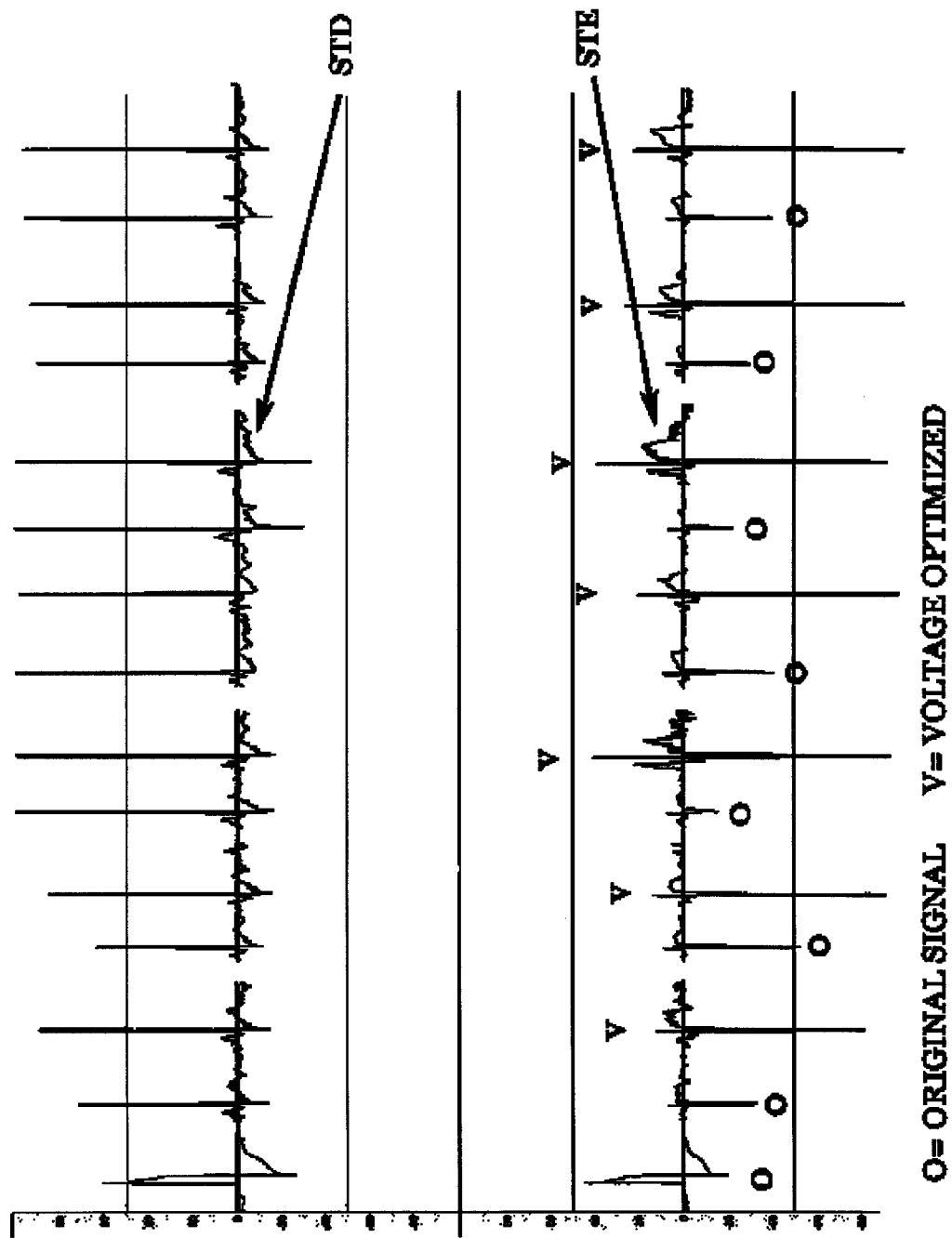
FIG. 15. Shows ST shift which becomes apparent only after voltage optimization.

FIG. 15 shows non-consecutive segment (two beats each) from a recording done without independent gain modulation. In both leads, the first wave is the 1 mV calibration signal followed by pairs of consecutive beats taken from different parts of the recording. The first beat of each pair is as it was originally recorded (O) and the second (V) is voltage optimized using CVAT software. Both the upper and lower leads are similarly treated. The $5^{th}$ pair in the lower lead, which has the lowest QRS voltage in the original signal, is the one which shows the most distinct ST segment elevation in the voltage optimized beat in the lower lead and depression in the opposite lead. The ST elevation can not be seen in the original beat. If we quantify the S wave in the original beat of the $5^{th}$ pair according to the calibration signal, this S wave would be about 6 mm in total and the ST elevation would not be equal to the 1-mm criterion. However the voltage optimized, second beat of the $5^{th}$ pair, shows that the ST elevation is about 20% of the S wave. This figure shows well the constant variation in the QRS voltage for which there is no adjustments possible in the calibration-based ST shift quantitative approach.

Figure 16:
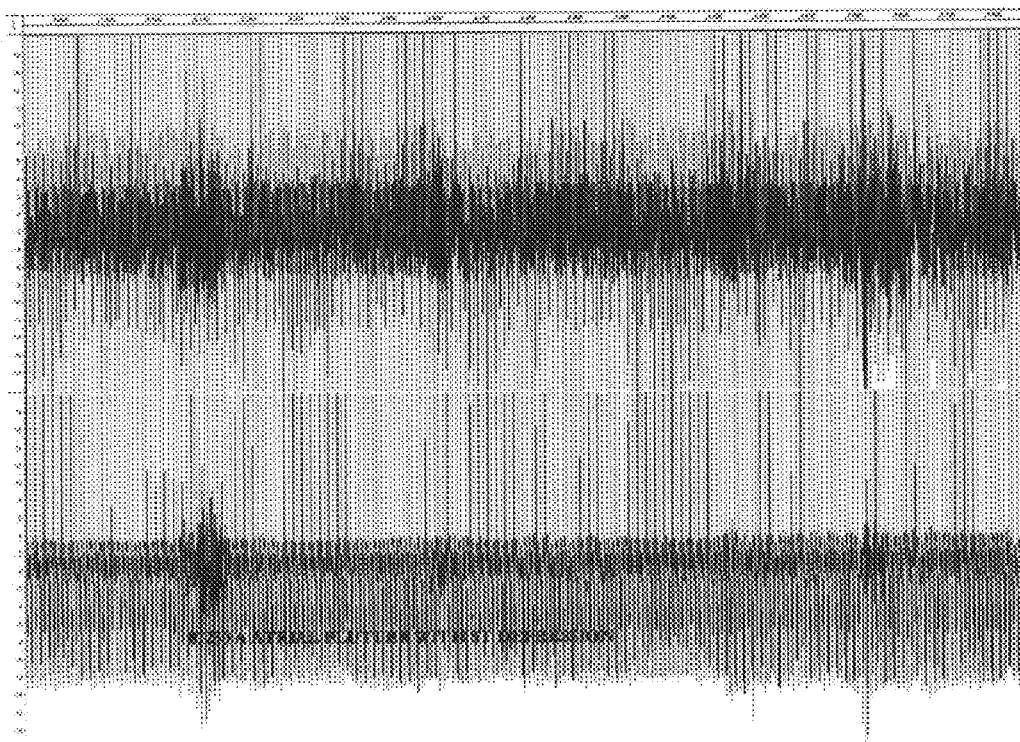
FIG. 16. Shows a CVAT pattern of ST depression and atrial flutter.

In FIG. 16, the QRS band shows the regular irregularity of the heart rate due to atrial flutter in a patient who also has ST depression. Both are readily identified in the visually compressed CVAT pattern.

Figure 17:
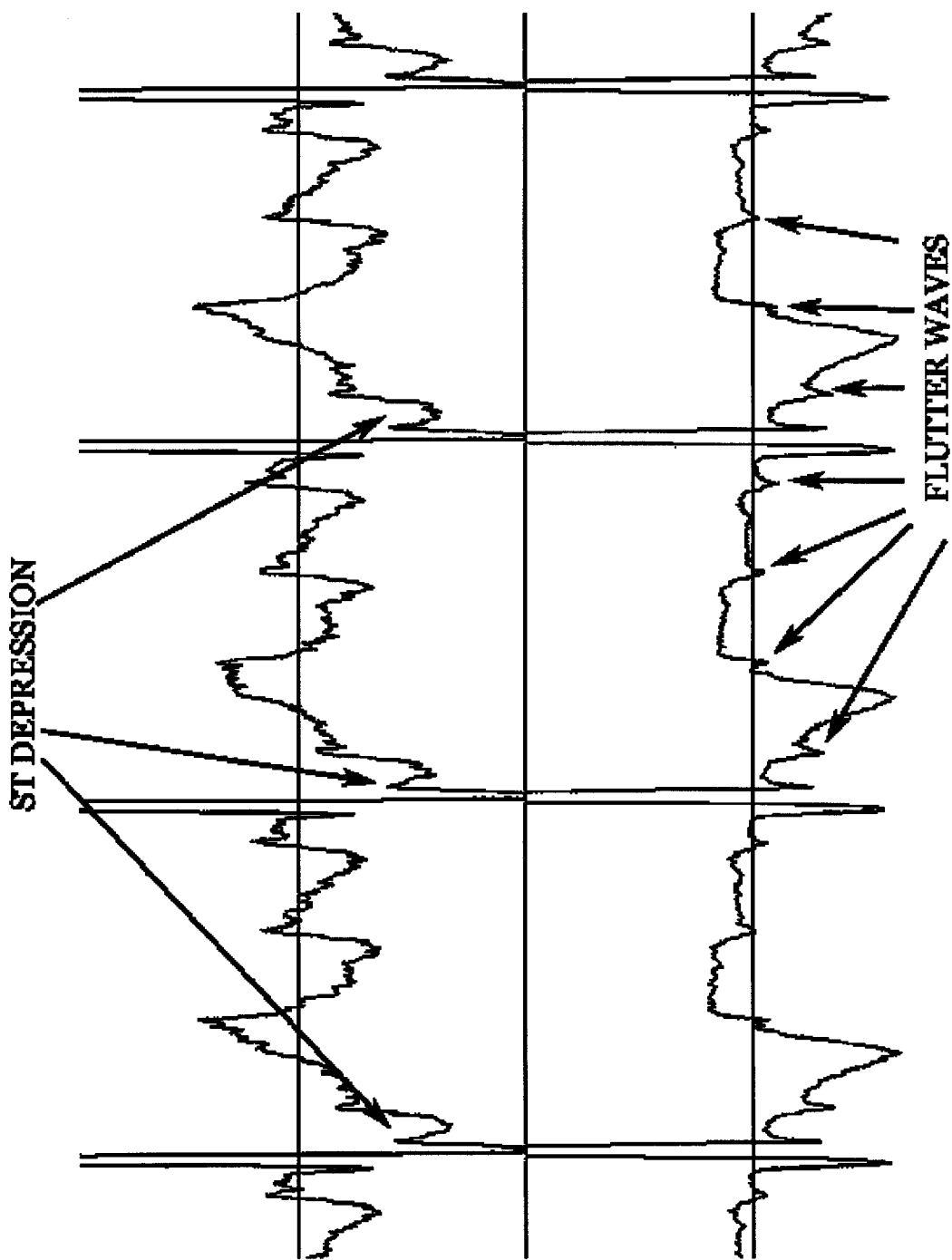
FIG. 17. Shows ST depression and atrial flutter in an expanded ECG.

FIG. 17 is an expanded tracing of the pattern showing atrial flutter and ST depression; the flutter waves are visible showing a 4:1 ventricular capture rate. This degree of visualization of the ECG is not possible with conventional Holter analysis.

Next, intermittent atrioventricular and intraventricular conduction defects are described. The conduction system is relatively more resistant to ischemia than the rest of the myocardium; hence when it is affected enough to show conduction blocks, a severe degree of ischemia must be suspected. Atrioventricular and intraventricular blocks can be readily found using CVAT. The nature of the conduction abnormality can be further defined by expanding and magnifying the signal if necessary. In the compressed CVAT mode, conduction blocks have characteristic patterns.

Figure 18:
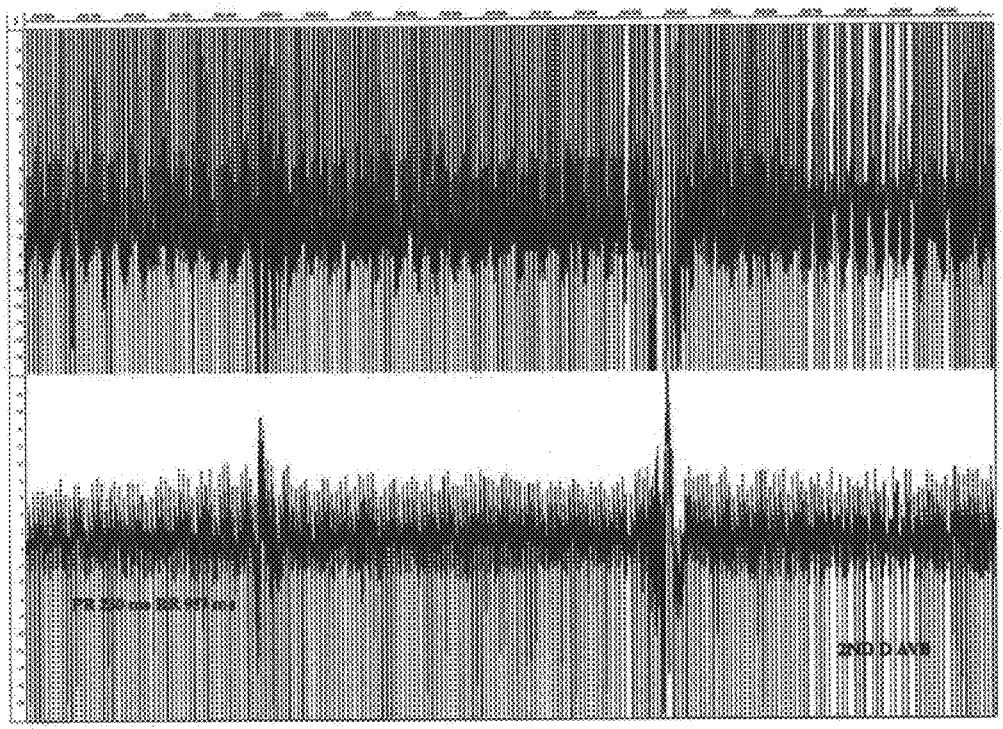
FIG. 18. Shows a CVAT pattern of intermittent $2^{nd}$ degree atrioventricular (AV) block.
Figure 19:
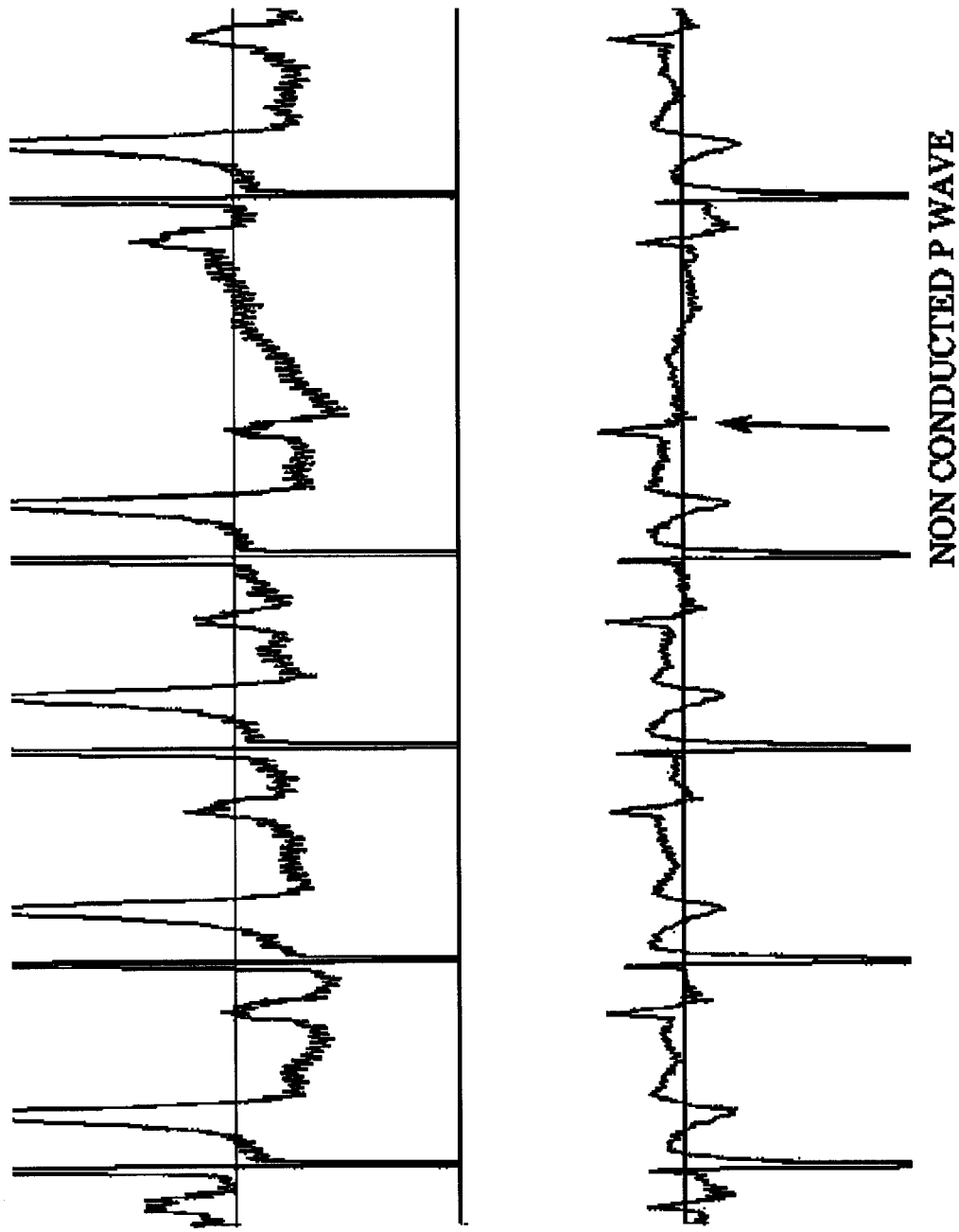
FIG. 19. Shows $2^{nd}$ degree AV block in an expanded ECG.

FIG. 18 shows the compressed CVAT pattern of intermittent second degree AV block. The QRS band in the right size of the figure has gaps which resemble a comb with broken teeth. FIG. 19 is an expanded view of this record in which the second-degree atrioventricular block is readily visualized. Two P waves are identified, the first does not conduct to the ventricle, and the second triggers a ventricular contraction. The pattern is repeated in consecutive cycles. Independent channel gain was not used in this recording.

Figure 20:
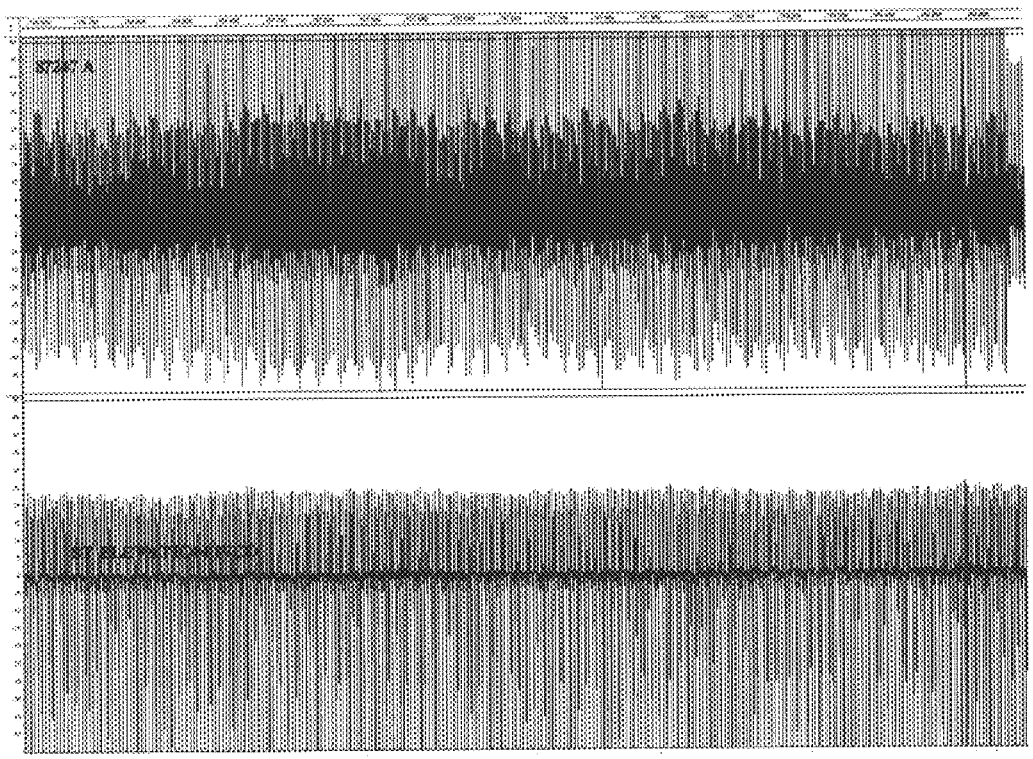
FIG. 20. Shows a CVAT pattern of ST elevation and intraventricular conduction delay.
Figure 21:
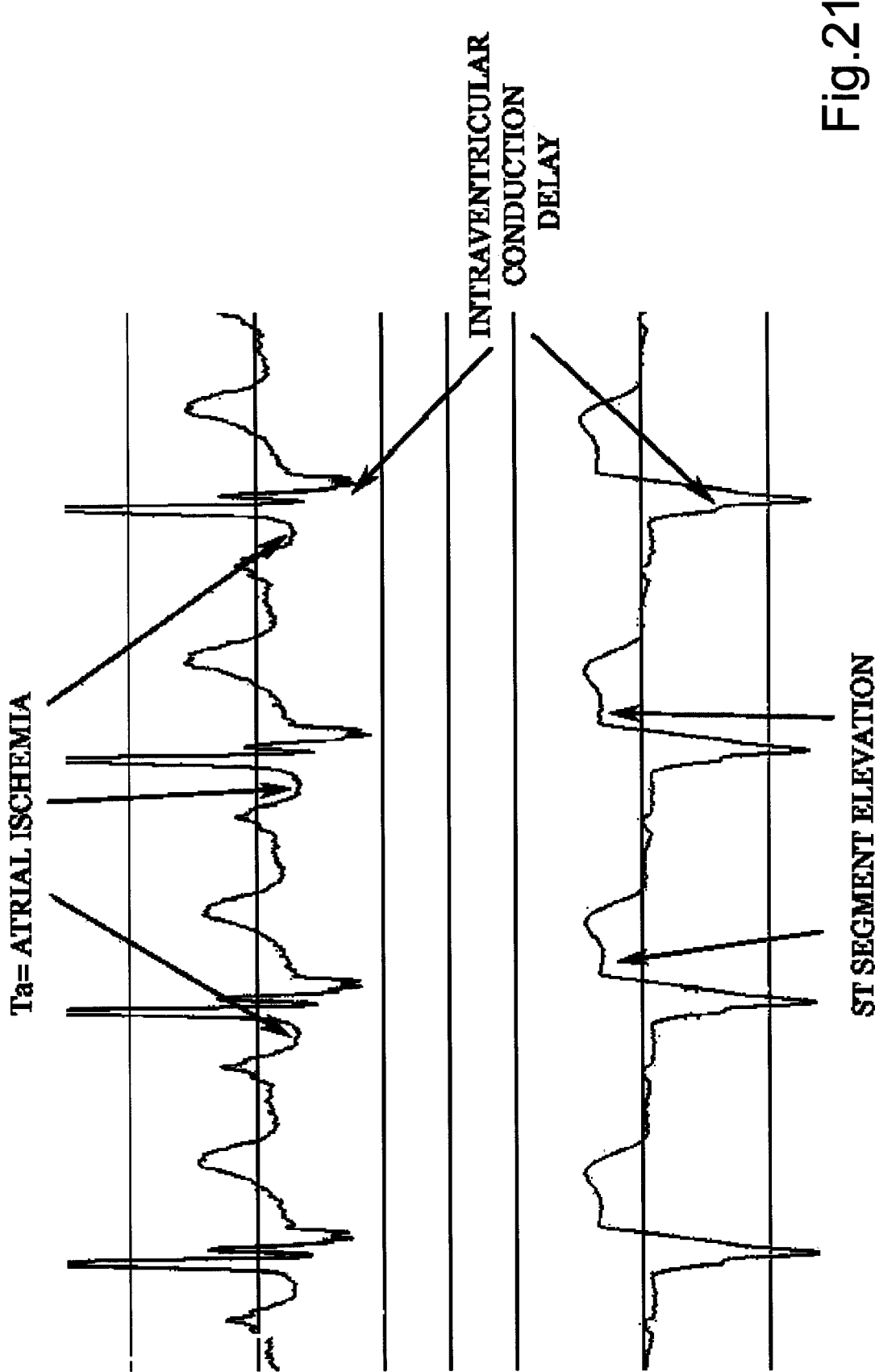
FIG. 21. Shows intraventricular conduction delay (ICD) and ST elevation in an expanded ECG.

FIGS. 20 and 21 show the visually compressed and expanded patterns of ventricular ischemia (ST elevation) and intraventricular conduction delay. Atrial ischemia (Ta) is readily apparent in FIG. 21.

Figure 22:
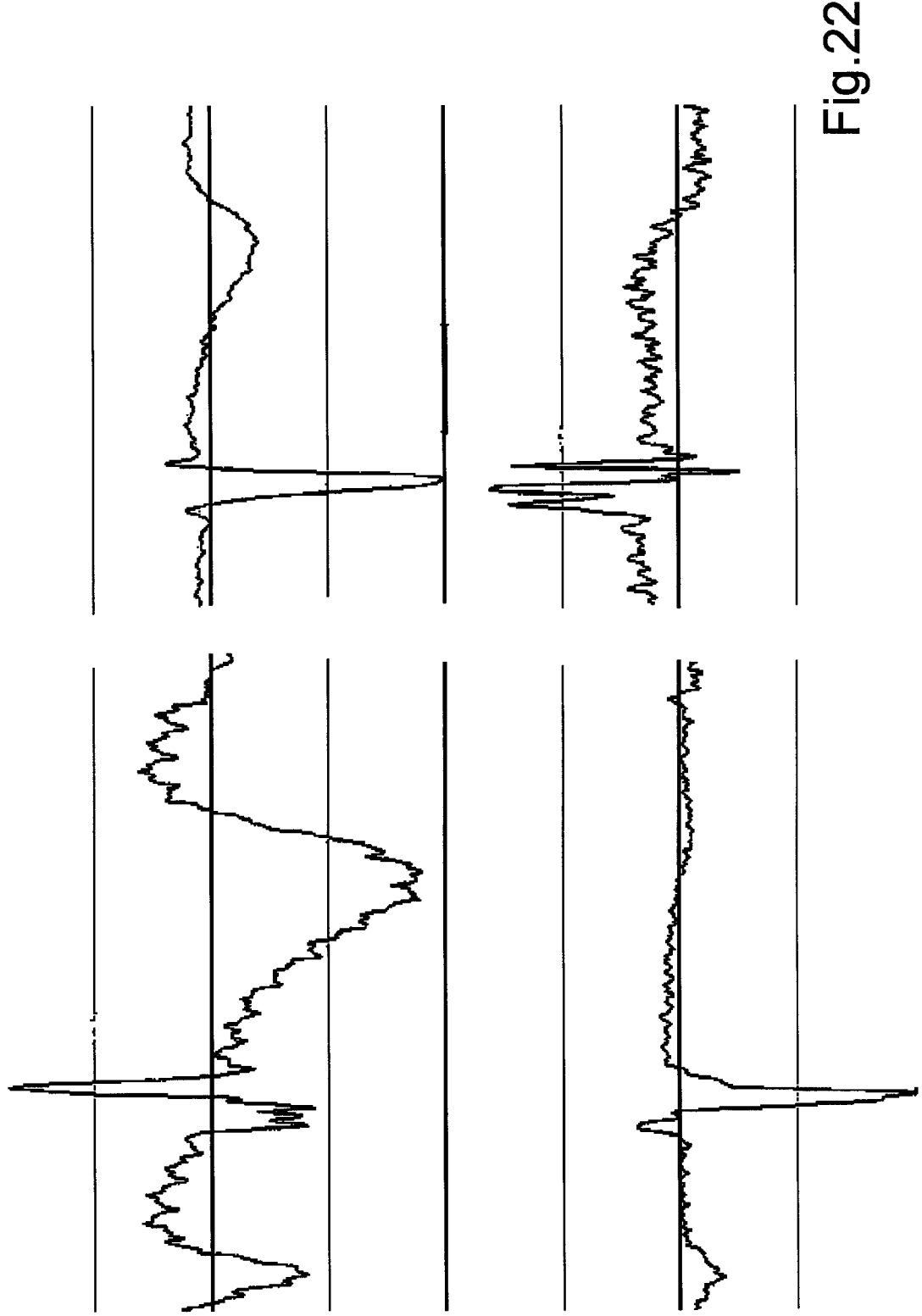
FIG. 22. Shows intermittent, shifting ICD.

FIG. 22 shows alternating intermittent intraventricular conduction defect (ICD) in the $1^{st}$ beat of the upper lead and the second beat of the lower lead. The beats are not contiguous, are placed next to each other for comparison only. This patient had changes in the upper lead alternating with changes in the lower lead, suggesting a shifting location of the ischemic area of the heart. Note the widened QRS and the initial slurring of the deflections in the $1^{st}$ upper and $2^{nd}$ lower beats. Compare these beats with their counterparts in the opposite leads which have a near normal configuration. Note also that the T waves following the beats with abnormally conducted QRS have a different configuration of the T waves compared with the other beats. The abnormal T waves reflect the disarray in repolarization consequent to the aberrant intraventricular conduction in the preceding QRS.

Current Holter algorithms lack integrity, dynamic range, fidelity and resolution and can not match human ability to recognize morphologic patterns. For these and other reasons, current Holter analysis can not benefit from the wealth of ECG signs of ischemia and it is limited to dubious quantification of one point in the ST segment. CVAT is designed to identify all the valuable electrocardiographic signs described in the peer-reviewed literature (mainly from studies done in exercise testing laboratories) to improve Holter analysis and facilitate ischemia detection.

T wave morphology changes as sign of abnormal repolarization will now be described. Current Holter analysis algorithms rely on mathematical formulae which use calculated slopes and intersects in an attempt to identify electrocardiographic landmarks that are difficult to precise even with visual magnification of specially taken 12 lead ECG's. Analog reconstruction of the T wave with current algorithms is poor due to lost data, and poor fidelity, resolution and deterioration of the dynamic range of the scanty signal preserved. Morphologic evaluation of incomplete electrocardiographic signal of poor quality is questionable, at best. The low quality of the highly compressed and filtered ECG signal encoded by the current Holter algorithms does not permit retrieval of the analog electrocardiogram as it was encoded in the magnetic tape. CVAT recovers the intact signal and enhances it to create a rich digital file using state-of-the-art software dedicated to preservation of the dynamic range, high fidelity and resolution. CVAT can accurately magnify at will both the time and voltage domains rendering ECG's of optimum quality suitable for all kinds of measurements and morphologic evaluation.

Figure 23:
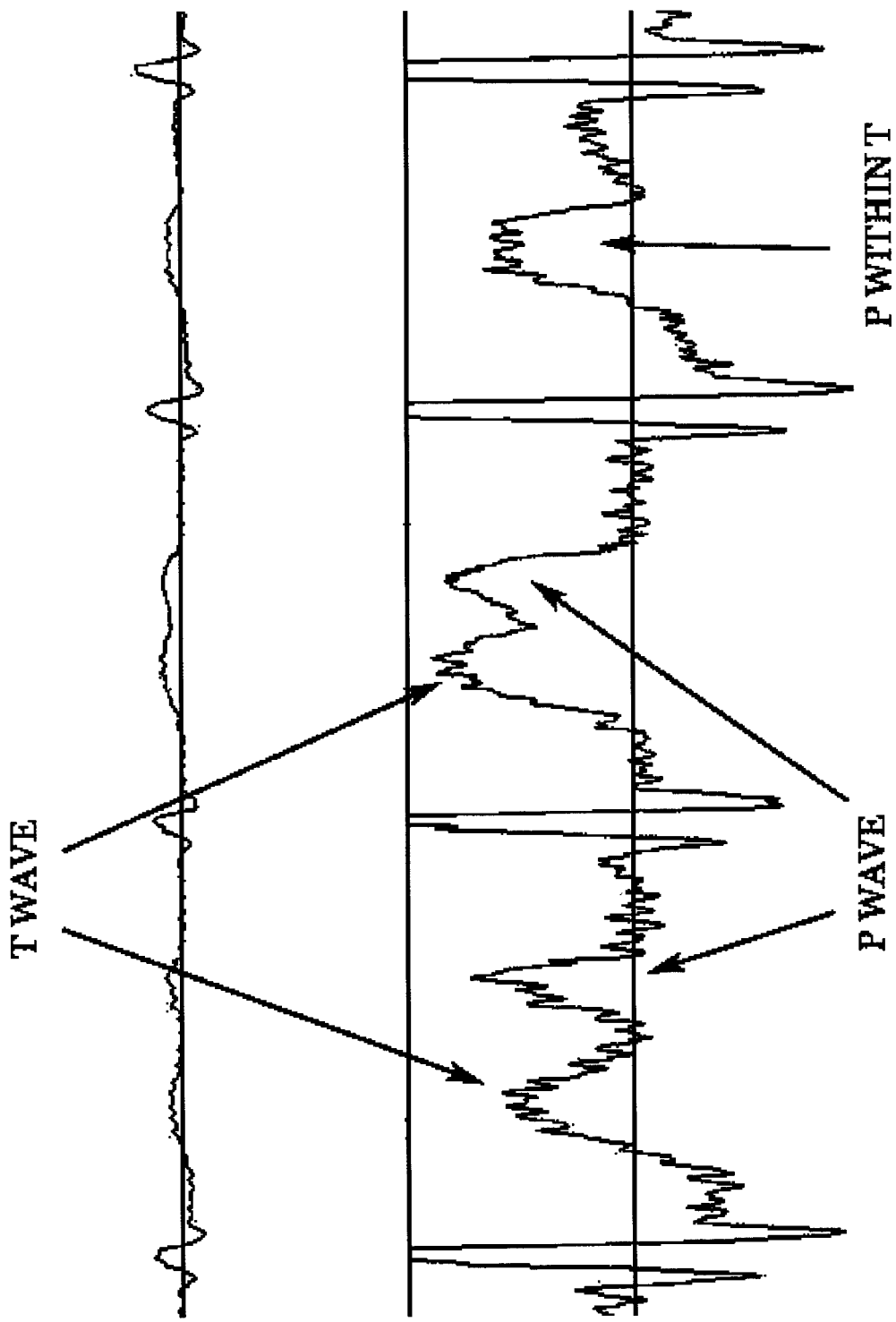
FIG. 23. Shows a P wave marching on the T wave visible through voltage optimization.

The four beats in the upper and lower rows of FIG. 23 are the same beats, duplicated from the same lead. This portion of the file has been resampled from 44,100 Hz to 96,000 Hz in both rows. In the Y-axes, the voltage has been optimized in the lower row only. Note, in the lower row, the marching of the P wave into the T wave (second beat) to merge with the T in the third beat. This kind of evaluation is not possible with current Holter algorithms.

Repolarization abnormality is a harbinger of potentially lethal arrhythmia (see "Electrical Alternance" below) myocardial infarction, or sudden death. Abnormal T wave morphology suggests myocardial intracellular changes which alter orderly, normal, cardiac cell repolarization. Abnormal repolarization can be a consequence of abnormal depolarization or ischemia and the cause of serious arrhythmia.

Under normal conditions, the T wave has the same polarity than the QRS deflection. Inscription of the T wave starts when the plateau of the action potential of the epicardium separates from that of the mid myocardial cells (mesocardium). As the voltage gradient between the epicardium and the mesocardium continues to expand, the ascending limb of the T waves is inscribed in the ECG at a slower rate than the descending limb of the T wave. The ascending limb inscribes the peak of the T wave when the epicardium is fully repolarized. In the opposite side of the ventricular wall, the plateau of the endocardial cell action potential separates from that of the mesocardial cell generating an opposing voltage gradient that limits the amplitude of the T wave and starts inscription of the descending limb of the T wave. The full repolarization of the mesocardium marks the end of the T wave. The time elapsed from the peak to the end of the T wave is an index of the degree of transmural dispersion of repolarization. A disproportionate prolongation of the action potential in the mesocardium prolongs the time from the peak to the end of the T wave (Tp-Te) and widens the T due to slower rate of descent of the distal limb. This prolongation of the Tp-Te may be also out of phase with changes in the R-R interval; i.e. it does not shorten or elongate proportionally when the heart rate increase or decrease, respectively.

The internal harmony of repolarization intervals will now be described. When electrocardiographic intervals are measured to assess repolarization, the standard reference for comparison is correction to an "ideal" heart rate of 60 beats per minute. More important than this comparison is the lack of pari passu shortening of repolarization with shortening of the cycle length. The corrected QT (QTc) interval is considered a surrogate of the cellular action potential duration. The QT interval includes electrical depolarization and repolarization of the ventricles and is a limited reflection of the complex electrogenesis of ventricular repolarization. The QTc has been shown to be of no value to predict mortality or arrhythmic events (Circulation 1998; 97:2543–2550). A study (J Am Coll Cardiol 1987; 10:1313–21) in which 19 automated QTc measurement systems were compared found standard deviations as large as 30 ms when locating the end of the T wave compared with 6 ms for the QRS onset. This study compared recordings done with conventional 12-lead electrocardiographic equipment. The inferior quality of the Holter recordings would give similar or greater standard deviations if subjected to the same type of study. Any evaluation of T wave duration is complicated by the T wave changing morphology within a recording period. Valid diagnostic conclusions can not be based on imprecise landmarks, measurements "normalized" with formulae established for more precise and complete signal obtained with superior type of equipment and when the standard deviation of the method is probably larger than the elongation supposed to be clinically significant.

There are researchers who believe that T wave morphology is more important than its total duration. The duration of repolarization usually changes in unison and in harmony with the duration of each heartbeat. Harmonic change is probably more important for diagnosis and prognosis than milliseconds of difference in "corrected" QT. The concept of measuring the interval between the peak and the end of the T wave as a measure of ventricular repolarization has been proposed several years ago (Antzelevitch et al J Am Col Cardiol; 1994; 23:259–77). This time interval represents the transmural dispersion of repolarization: the longer it is the more fragmented and abnormal repolarization is likely to be. Evaluation of the morphologic features of the ST segment and the T wave, looking for manifestation of electrical alternans, assessing the internal coherence of the repolarization intervals and their concordant change with heart rate variation are more valuable than the simple determination of the QTc.

The instant CVAT method proposes that better measurements of repolarization and its accommodation to changing heart rate are:

Duration of repolarization measured from the J point to the end of the T excluding the QRS since this complex reflects ventricular depolarization.

Time from the J point to the end of the T (J-Te) reflects epicardial, mesocardial and endocardial repolarization time Tp-e stands for the time from the peak (Tp) to the end (Te) of the T wave as an expression of ventricular transmural repolarization time Time from J point to J point (J-J) as a measure of one heart beat duration (Tp-e/J-Te)×100 represent the relative duration of transmural repolarization time as a percent of the total duration of the repolarization. Prolongation of the transmural repolarization, in disproportion to the total duration of repolarization, is likely to reflect transmural repolarization dispersion, prolongation of the vulnerable period and heightened risk for ventricular arrhythmia. This percent value, determined continuously or at regular intervals (such as every 15 to 60 minutes) plotted, in the Y-axes, against clock time of Holter recording, in the X-axes, represent circadian variation in the relative duration of transmural repolarization.

(J-Te/J-J)×100 express the relative duration of total repolarization time (epicardial plus transmural) as part of total cycle length and correlates total repolarization to heart rate.

Normally, J-Te should shorten as J-J shortens. Plotting this percent value versus clock time will give an idea of the circadian variation in total repolarization time as part of it's own cycle length (and hence heart rate) from which valuable diagnostic and prognostic information could be derived.

Preliminary data suggests that normal repolarization (J-Te) may be at or below 30% of the cycle length (J-J) and transmural (epicardial to endocardial) repolarization (Ta-Te) should also be at or below 30% of J-Te. Further work is being done by the instant inventor to further precise these relationships.

Figure 24:
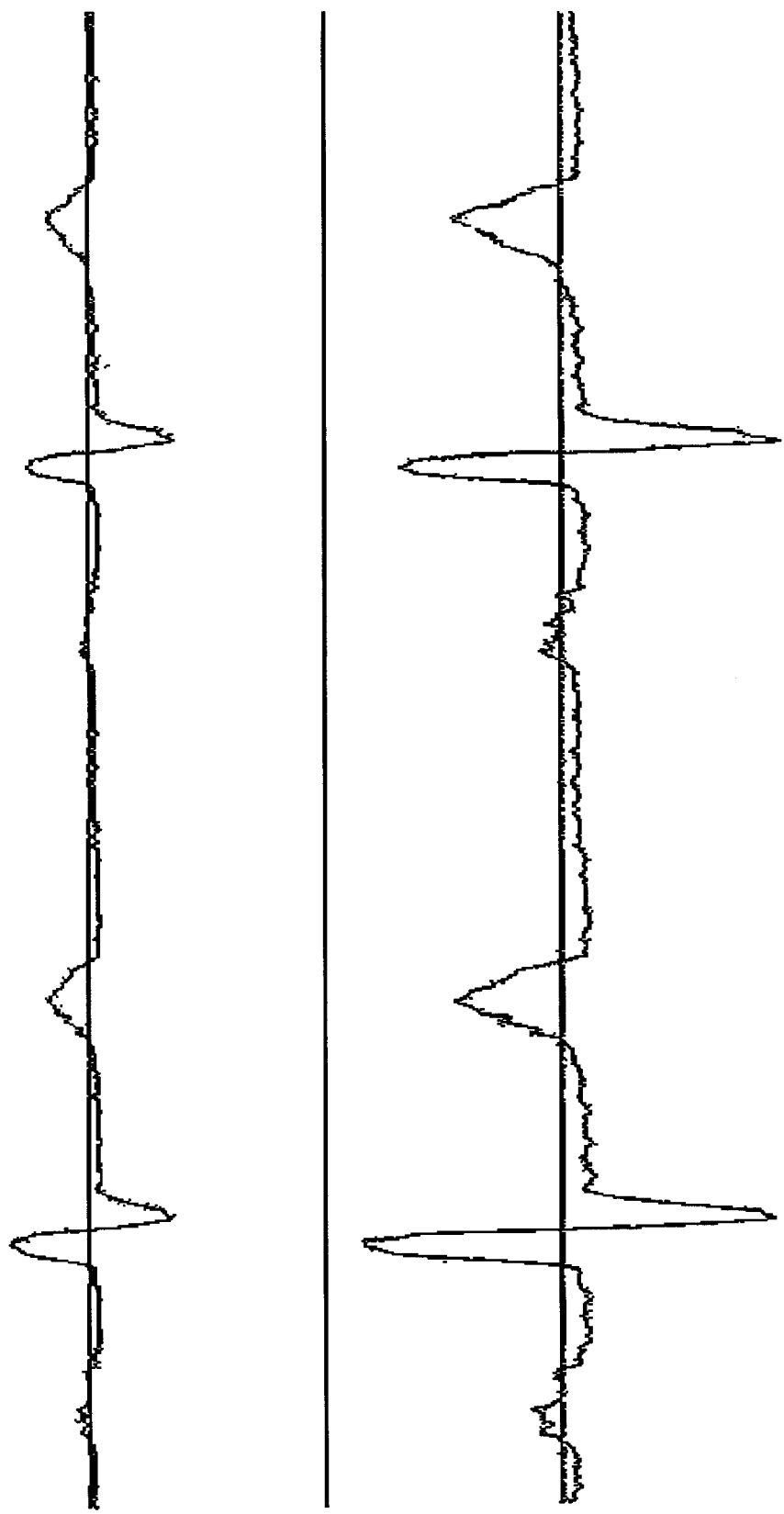
FIG. 24. Shows an example of resampling and voltage optimization.

In FIG. 24, the two consecutive beats in the upper row were copied in the lower row. The ECG signal was resampled from 44,100 to 96,000 Hz, in both leads. Only the lower lead was voltage optimized. This process can be used to expand the time and voltage domains for precise identification of electrocardiographic landmarks. In this figure, the T wave has a symmetric (arrow point like) shape, different from normal where there is a slower ascending than descending limb. The J-J is 791.5 ms (heart rate=76 beats per minute). J-Te is 237.5 ms, Tp-e is 50 ms. Hence, the transmural repolarization (Tp-e) is 21% of the total repolarization time (J-Te) and the total repolarization time (J-Te) is 30% of the total cycle length (J-J).

Figure 25:
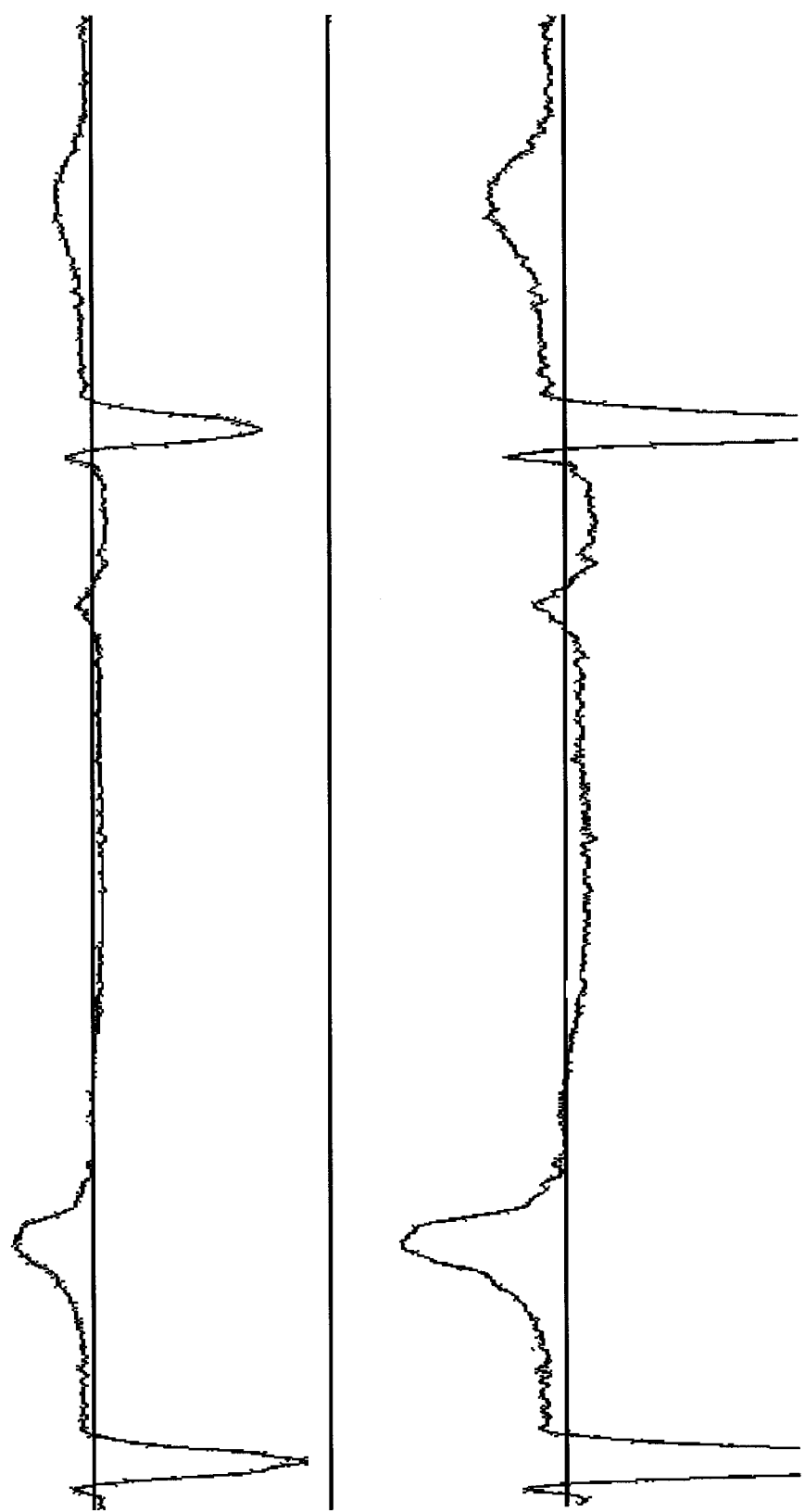
FIG. 25. Shows beat to beat change on T wave morphology.

In FIG. 25, two consecutive beats are duplicated in the lower row, both were resampled, only the lower row was voltage optimized the cycle length is 1054.1666 ms (heart rate=56.9 beats per minute). The first T wave J-Te is 279ms; Tp-e is 96.6 ms or 34.6% of J-Te. The second T wave J-Te is 291.6 ms; Tp-e is 83.3 ms or 28.5% of J-Te. The relative longer duration of the transmural repolarization of the first T wave (Tp-e of 34.6% vs. 28.5% of their respective J-Te) coupled with the distinctly different morphology and height (the first T is 2.5 times taller and more peaked than the second) suggest heterogeneous repolarization (electrical alternans).

Figure 26:
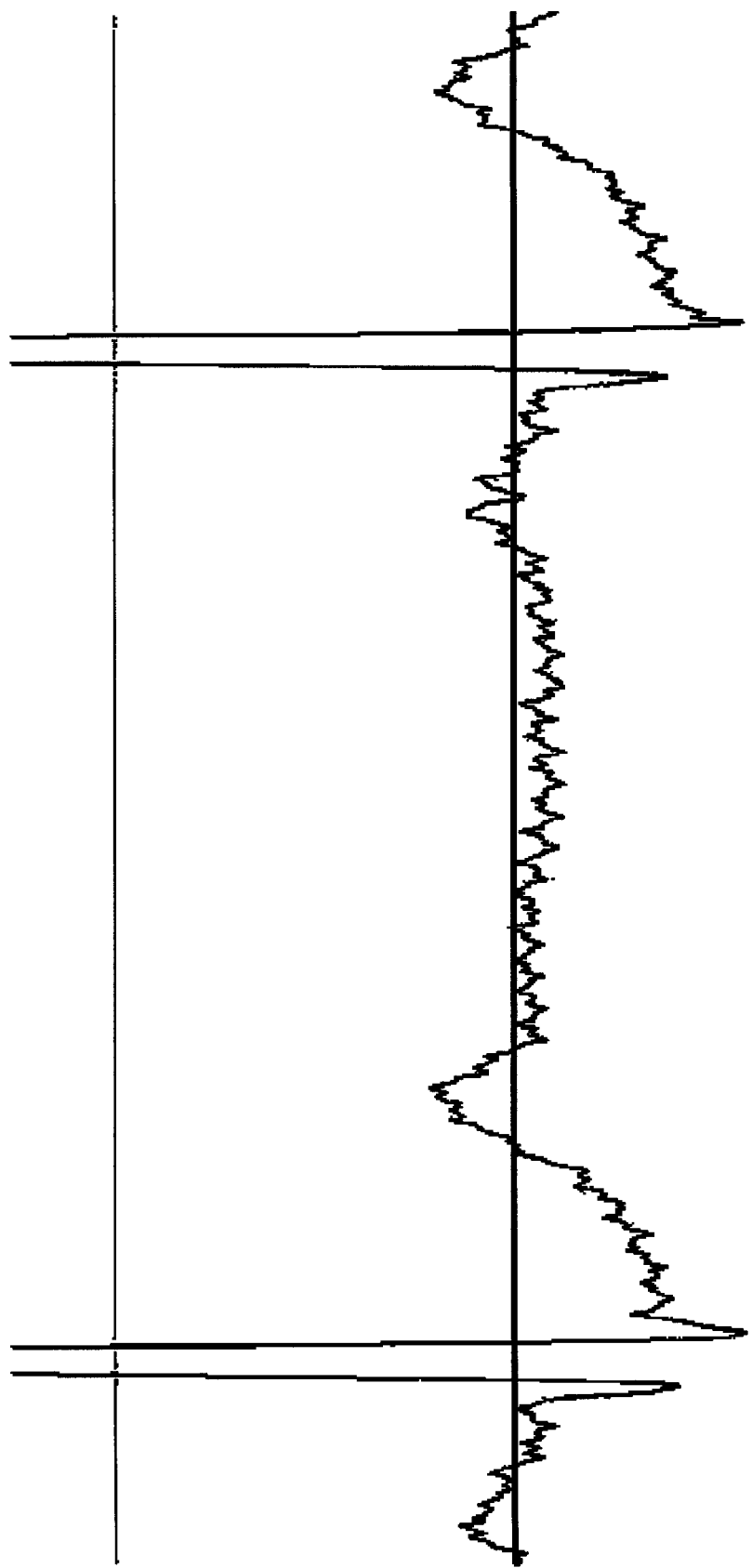
FIG. 26. Shows ST depression in the beats opposite to those in FIG. 25.

FIG. 26 shows the opposite lead to that shown in FIG. 25, the two beats opposite to those shown in FIG. 25 have been isolated. Significant horizontal ST segment depression is shown. Electrical alternans and heterogeneous repolarization may be caused by myocardial ischemia.

Figure 27:
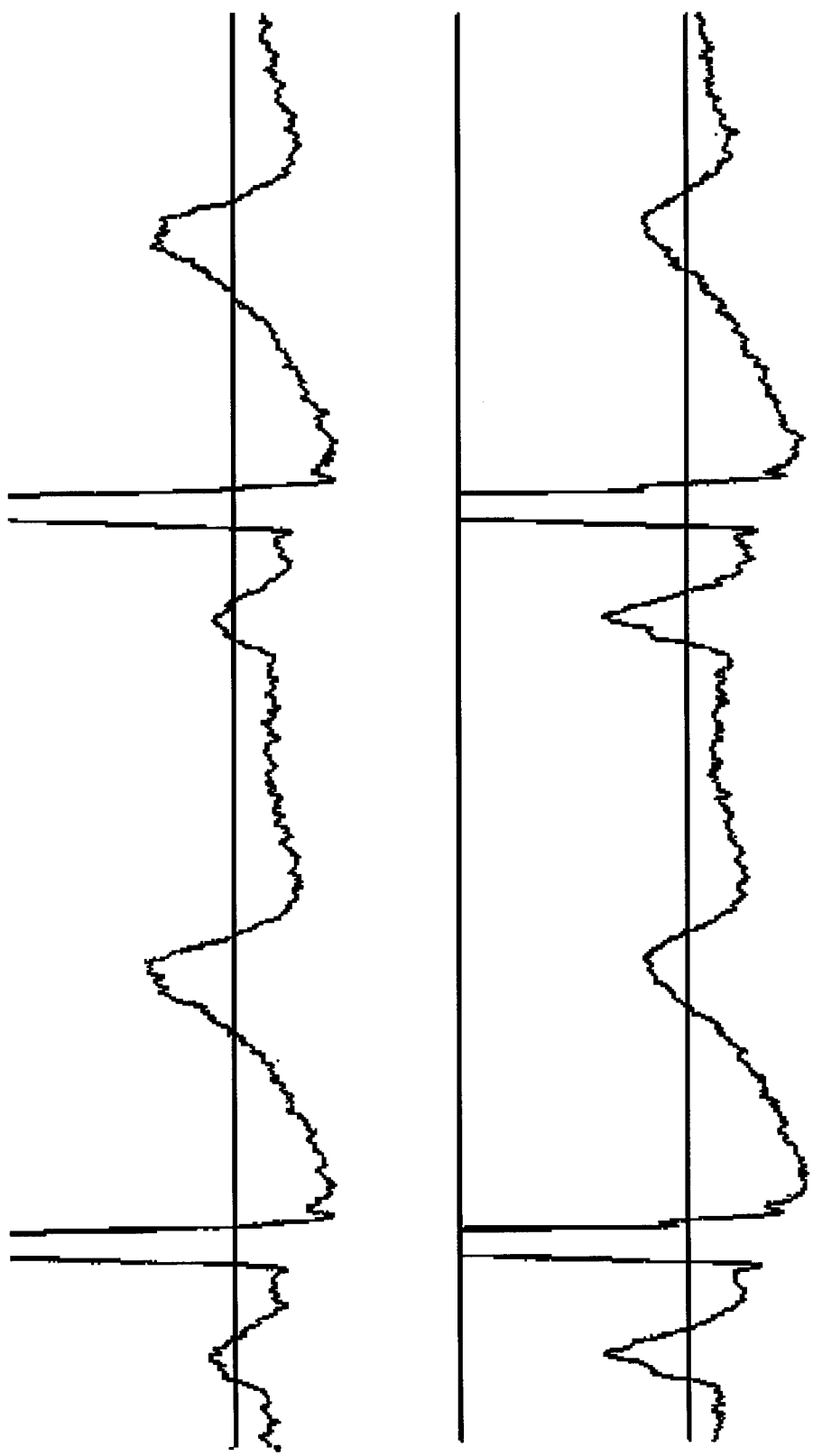
FIG. 27. Shows an example of ST depression and biphasic T waves.

In FIG. 27, ST segment depression and biphasic (+−configuration) T waves are present in both leads. The cycle length (J-J) is 783.3 ms (heart rate=76,5 beats per minute), J-Te is 458.33 ms, Tp-e is 195.83 ms Transmural repolarization (Tp-e) takes 42.7% of the total repolarization time (J-Te) which represents 58.5% of the cycle length (J-J). The relative prolongation of both the total and the transmural repolarization times is in keeping with the ST segment depression seen in both leads. Current Holter analysis would have placed the end of the T at an intersect with the isoelectric line based only on a line fit onto the down sloping arm of the first (positive) phase of the biphasic T. The negative phase of the biphasic T would have been excluded by the placement of the slope. Furthermore, its unlikely that the degraded signal would have shown the negative phase of the biphasic T. The ST segment depression has an upsloping trend; however, the ST fails to return promptly to the isoelectric line. The morphology of the ST in conjunction with that of the T wave strongly suggests ventricular repolarization abnormality probably due to ischemia.

Figure 28:
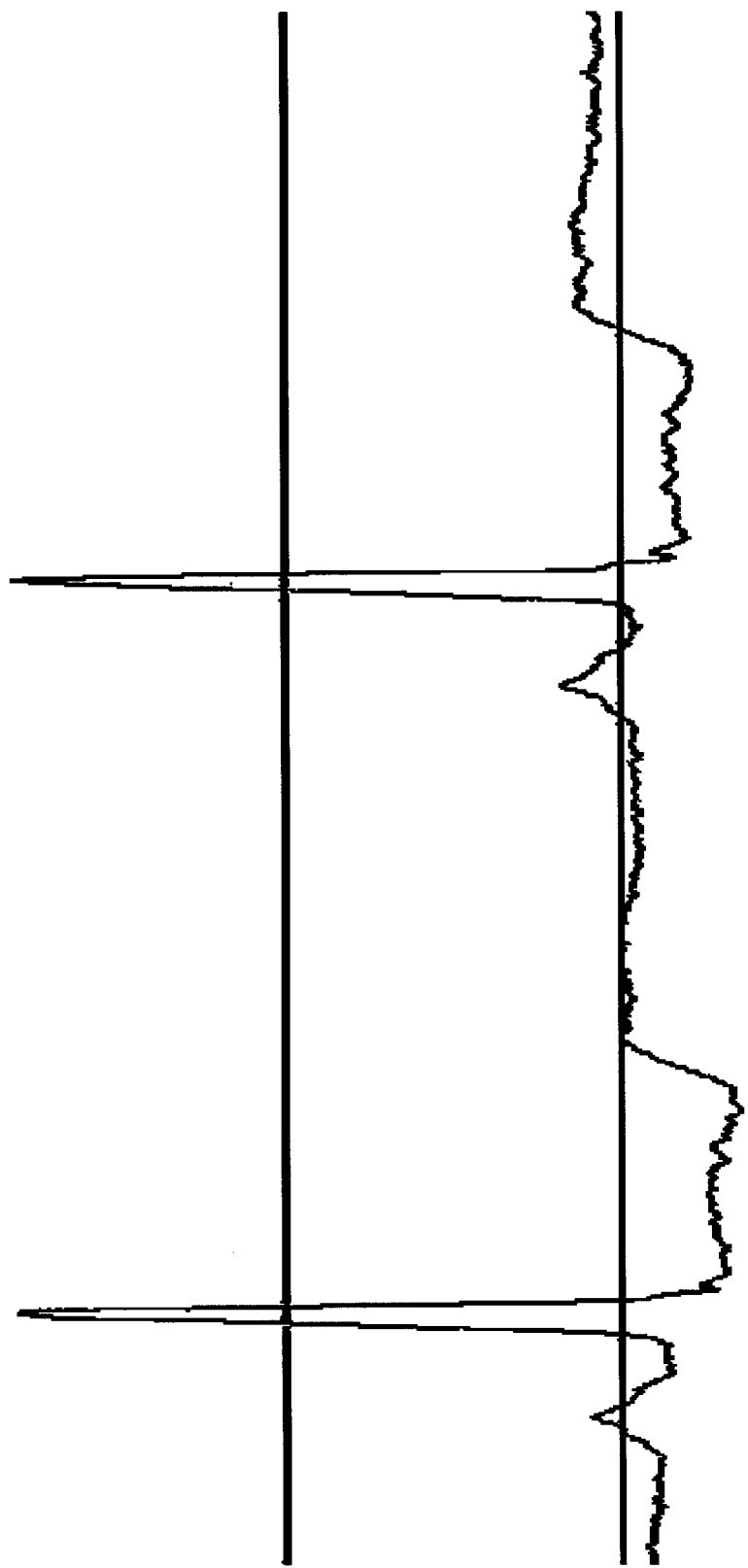
FIG. 28. Shows ST depression in the recording from which FIG. 27 was taken.

FIG. 28 is a tracing from the lower lead of the recording shown above a little later in the recording period. Distinctly horizontal ST segment depression with T wave inversion is documented which confirm the likelihood of myocardial ischemia in this patient.

Figure 29:
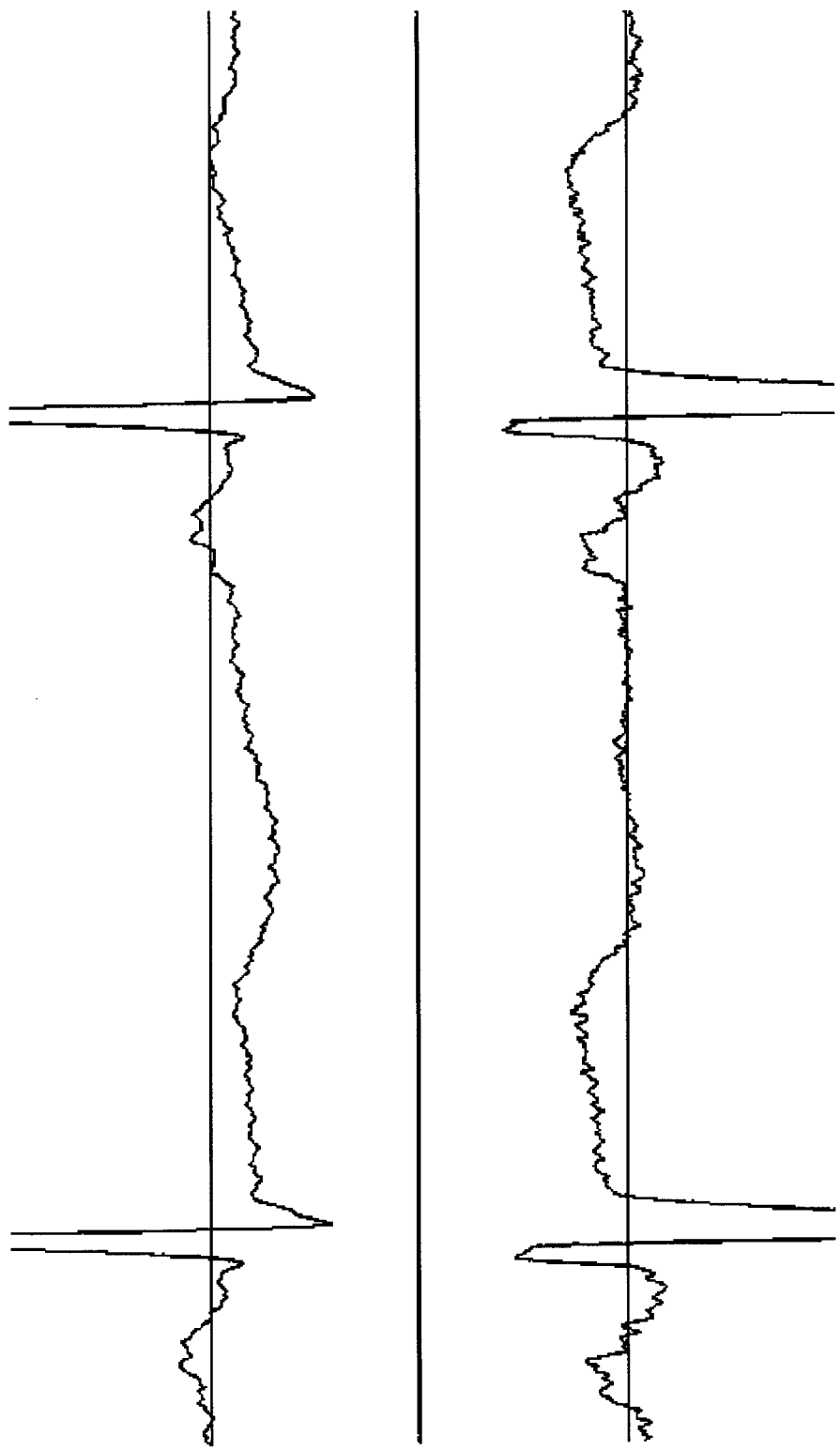
FIG. 29. Shows biphasic T waves.

The T waves in both leads of FIG. 29 are biphasic. In the lower lead J-J is 912.5 ms (HR=65.7 bpm), J-Te is 458.3 ms (50.2% of J-J) and Tp-Te is 270.1 ms; hence, 58% of the total repolarization is taken by transmural repolarization. ST segment depression in the upper lead and elevation in the lower lead are also present.

Figure 30:
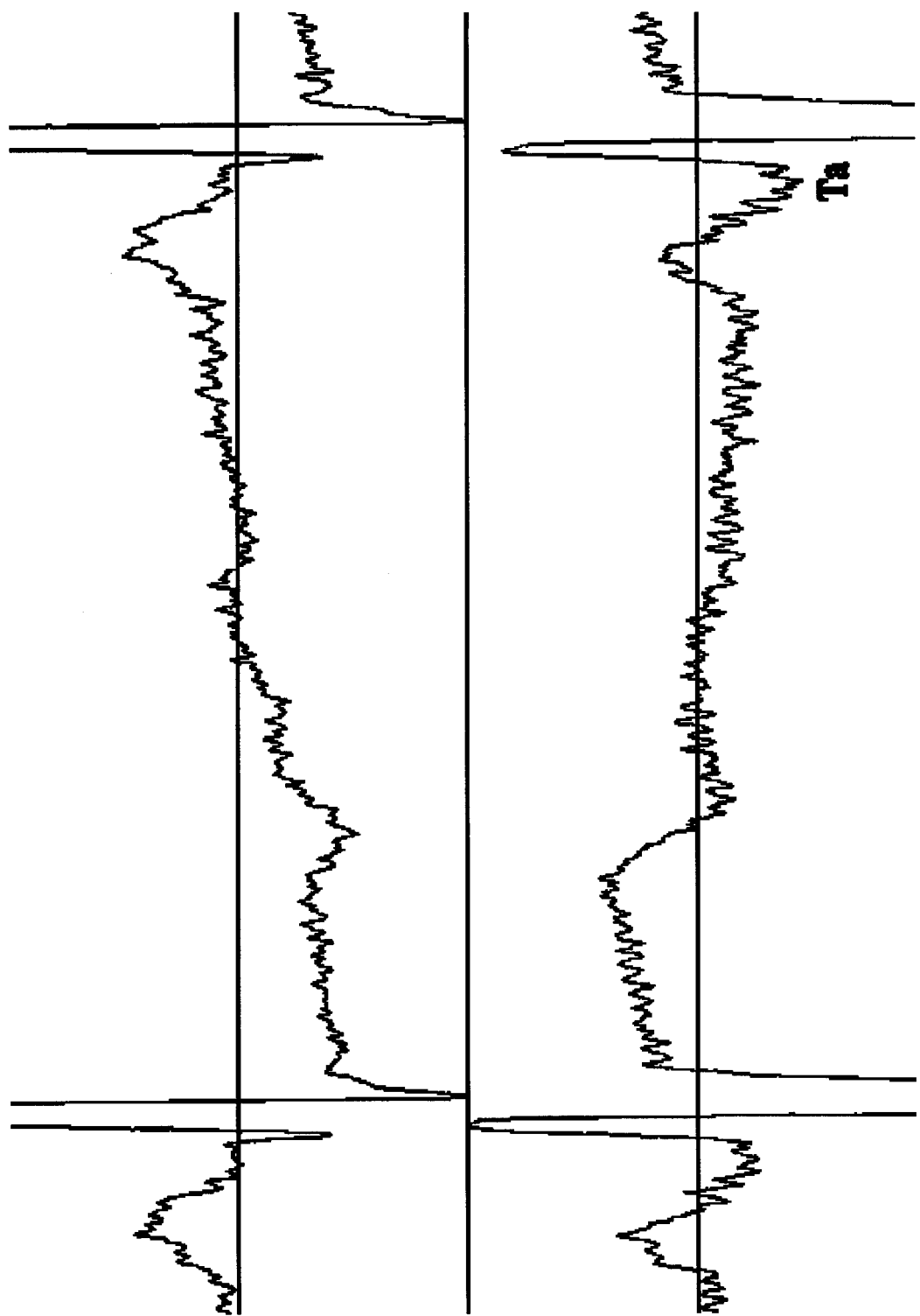
FIG. 30. Shows Ta, ST depression and elevation in the recording from which FIG. 29 was taken.

FIG. 30 is a tracing taken later in the same recording as FIG. 29. Compared with the previous figure, note the more pronounced horizontal ST depression in the upper lead and the ST elevation in the lower lead, confirmation of myocardial ischemia in this patient.

Figure 31:
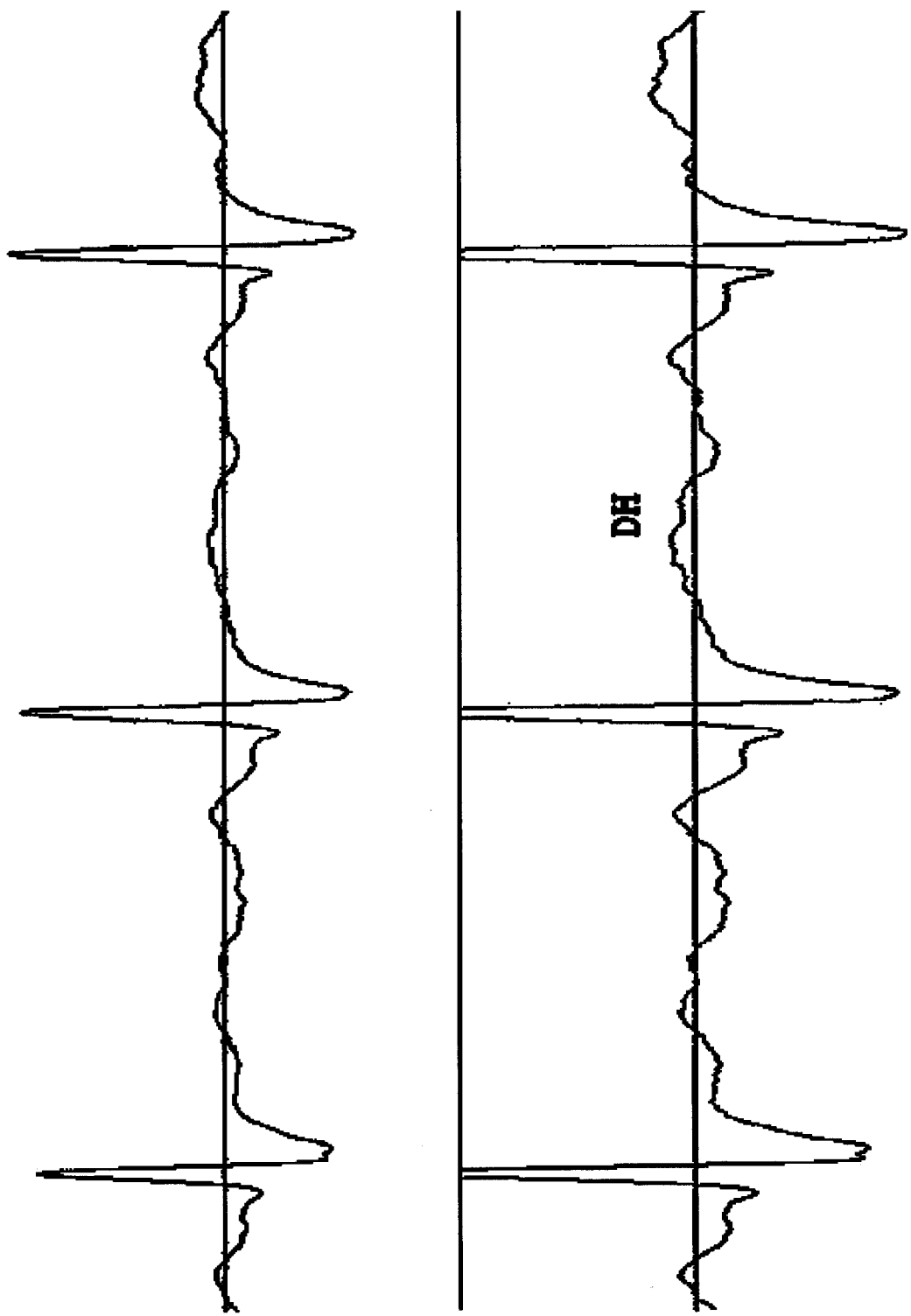
FIG. 31. Shows expanded and magnified ECG to show double hump T wave.

FIG. 31 shows three heartbeats in the same lead duplicated and resampled. Only the lower tracing was voltage optimized. The T wave has double hump morphology. This tracing raises the question: Is the transition from epicardial to endo-mesocardial repolarization at the peak of the first hump?

Figure 32:
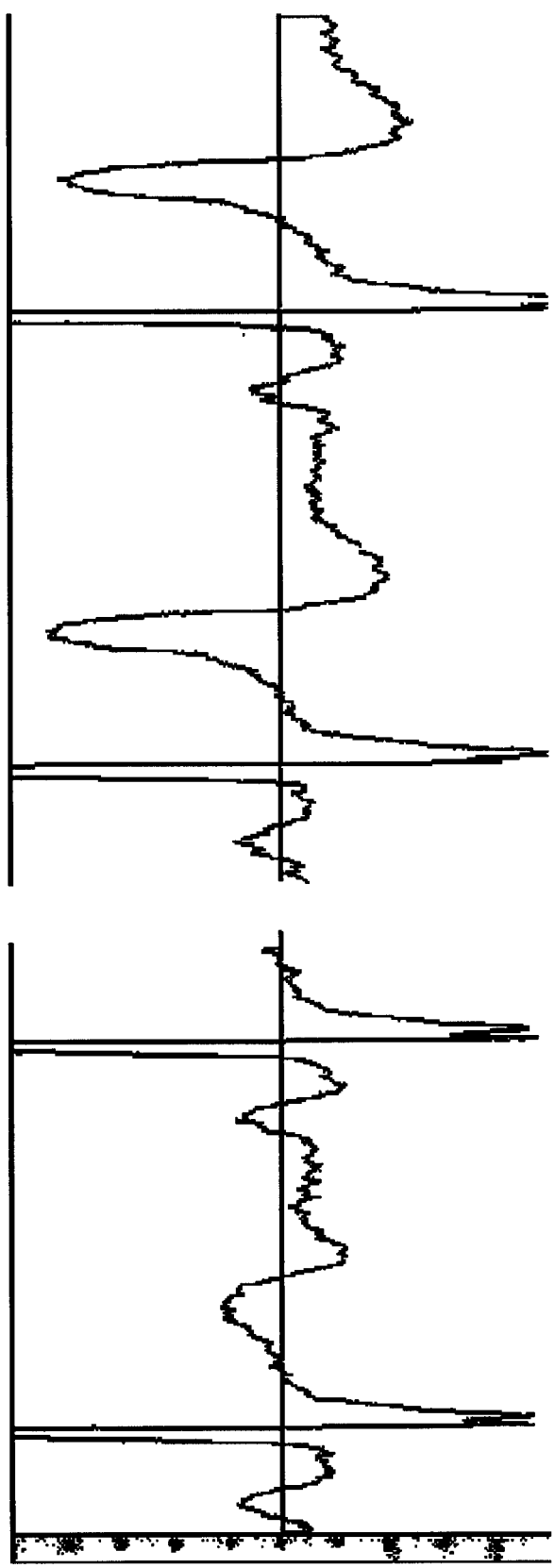
FIG. 32. Shows marked and quick change in T wave morphology.

FIG. 32 shows two heart beats (1stB and $2^{nd}$ B) located in the same recording, same lead, 20 seconds apart. The $1^{st}$ and $2^{nd}$ QRS constitute one cycle length and the $3^{rd}$ and $4^{th}$, the second cycle length.

The following measurements were taken from the first cycle length in FIG. 32:

| | |
|---|---|
| J-J | 770.83 ms (77.8 beats per minute) |
| J-Te | 362.50 ms (47.0% of J-J) |
| Tp-e | 187.50 ms (51.7% of J-Te) |

For the second cycle length:

| | |
|---|---|
| J-J | 883.33 ms (67.9 beats per minute) |
| J-Te | 406.25 ms (45.9% of J-J) |
| Tp-e | 220.83 ms (54.3% of J-Te) |

The positive phase of the biphasic T wave in the second beat is 4.3 times (apex of the T to the isoelectric line) taller than the T wave which follows the first QRS. The double hump morphology shown in FIG. 31 was observed in the same recording of the patient.

Work is ongoing by the instant inventor to further identify additional morphologic patterns, internal correlation of intervals and voltages in normal subjects and patients with different cardiovascular pathology as well as during percutanoeus transluminal coronary artery balloon dilatation.

The electrical alternans will now be described. Temporal heterogeneity in repolarization can be expressed in an individual beat (spatial heterogeneity seen as repolarization dispersion comparing the same ST-T in two or more different leads) or in a sequence of beats (dynamic heterogeneity shown as differences in duration and/or amplitude) also known as electrical alternans. Electrical alternans represents heterogeneity of cardiac muscle repolarization and/or depolarization as a consequence of myocardial ischemia and other forms of cardiac disease. It can be considered a harbinger of malignant arrhythmias.

Beat-to-beat microvolt alternation of the amplitude, unstable morphology and/or changing polarity of the T wave are markers of vulnerability to potentially lethal ventricular arrhythmia. There are research efforts to identify patients who have this electrocardiographic risk marker using sensitive spectral signal-processing techniques in specialized laboratories, by highly skilled electrophysiology experts. Electrical alternans documented during exercise induced tachycardia is a better predictor of arrhythmia vulnerability than signal averaged electrocardiography (Estes NA et al. Am J Cardiol 1997; 15:1314–8) or electrophysiologic testing in the cardiac catheterization laboratory (Hohnloser SH et al J. Cardiovasc Electrophysiol 1996; 7:1095–111).

Figure 33:
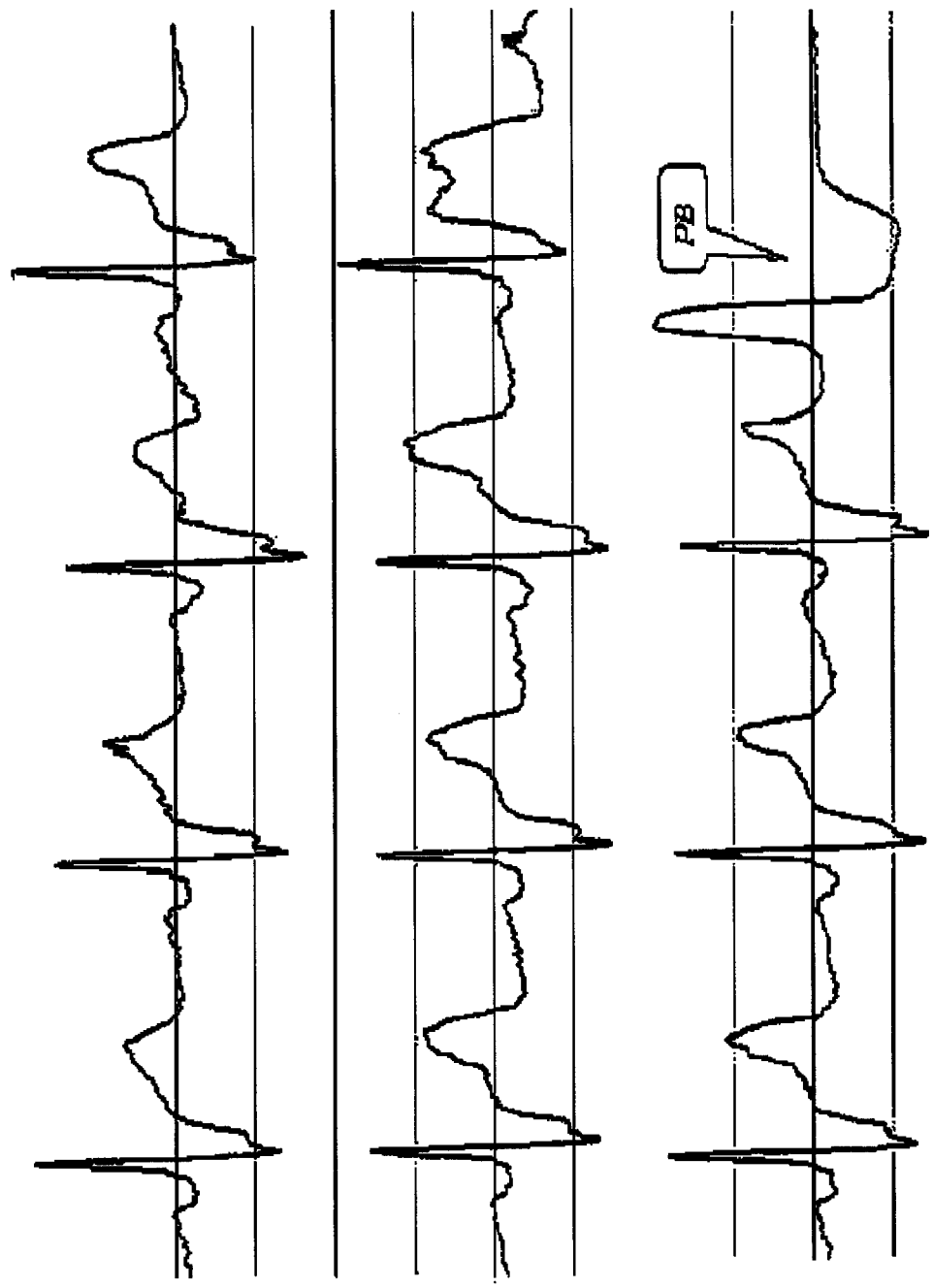
FIG. 33. Shows continuous tracing to show beat-to-beat changes in T wave morphology prior to a premature beat.

FIG. 33 is a 16 seconds consecutive strip from a recording analyzed with CVAT. Macroscopic beat-to-beat variation of the T wave morphology is noticeable; especially the peculiar morphology of the T wave that precedes the premature beat (PB). CVAT allows visual identification of beat-to-beat T wave morphologic changes which correspond to microvolt beat-to-beat variations in repolarization. Current Holter analysis lacks signal quality and quantity to match CVAT accurate morphologic analysis. CVAT brings into daily clinical practice a diagnostic tool heretofore available only as a costly experimental tool in few research laboratories and not yet applicable to patient care or large scale risk screening, both possible with CVAT.

Measuring time intervals in the Holter electrocardiogram is now discussed. As it is the case with data on microvolt range ECG signals, knowledge on electrocardiographic time intervals is the result of studies and experienced acquired using well maintained, standardized and calibrated stationary 12-lead electrocardiographs. Concepts arrived at in this manner were extended to Holter analysis. However, the following are some of the reasons to believe that the 12-lead ECG intervals are not necessarily applicable to the evaluation of ambulatory electrocardiography:

Holter recordings are done with relatively simple, battery-driven motors which run at very slow speeds without feedback regulation of the speed drive. The magnetic tape runs across the recording head at critically low speeds of 1.1 to 0.55 mm per second. Ten percent fluctuations in speed are said to be common in Holter recordings, and probably a 3% variation is the best that can be expected with the best equipment available today which is not used outside of few research centers. This factor of error in the conversion from time in the recording to real (24 hr) time is usually not accounted for. Servo control and closed loop technology can improve the steadiness of the tape transport speed at the critically low speeds needed but have not yet been incorporated into commercial Holter recording. The instant inventor is researching better technology and media to be used for the ambulatory recording of biologic waves.

Very fast play back of Holter recordings done at critically low speeds are another factor for the potential distortion of the time intervals and variation both within and across equipment used.

Tape stretch, wow, flutter, tape biasing etc. are likely to introduce more problems leading to less than precise determination of the duration of the intervals in the ambulatory electrocardiogram.

In current Holter analysis, duration of the QT and other intervals is measured in milliseconds. CVAT technology can measure down to one $10,000^{th}$ of a millisecond of real time in recordings digitized at 44,100 or 96,000 Hertz per second. Recordings digitized at 44,100 Hz can be resampled at 96,000 Hz. Sampling rates higher than 96,000 Hz are being tested. Lacking steady recording speed during Holter recording, absolute time measurements have to be interpreted with caution as useful to judge relative duration of different elements within a recording, but difficult to extrapolate and compare across recordings or across patients. Hence, in CVAT, internal concordance, as an expression of harmonic relationships within the electrocardiographic intervals of a given patient, is considered more important than absolute time measurements. It is believed that judging intervals relationship as an expression of harmonic continuity of electrophysiologic cardiac function is more useful than "correcting" time intervals using formulas developed for 12-lead electrocardiography. Basset's QTc and other formulas correct the QT interval using as reference "normal" population intervals at an ideal heart rate of 60 beats per minute. The formulas were derived from and for 12-lead electrocardiography. Critically low recording speeds, variable play back rate, tape stretch, wow flutter etc do not exists as factors of error in 12-lead ECG interval measurement. Hence, correction factors developed for 12-lead ECG are probably unsuitable for application to conventional Holter analysis.

Until better Holter recording equipment (e.g. with servo controlled recording speed and with precise 10, 100 and 500 Hz calibration) will be commonly available, the advantages of the CVAT mode of analysis can be applied to Holter recordings done with currently available equipment.

The 1 millivolt per second signal used today can be a used as a gage to measure time intervals. Across patient and across recorders comparisons may not be as precise as CVAT can be, but search for within a recording harmony of time intervals can be done until better recording equipment will be available.

Using Sound Forge, a window is opened to record 5 to 10 seconds of silence (a blank canvas) at identical sampling rate than that used to store the analog signal into the hard drive. The input format used should be samples per second. A 12 to 15 cycle length calibration signals is copied into the canvas from the middle or most stable part of the calibration period in the recording to be analyzed. Any beats, or waves within a beat, which need to be measured are also copied from the recording being analyzed into the canvas.

The first step is to expunge the areas of each beat which do not require precise duration measurement. Unless there is a need to measure QRS duration it is best to eliminate the QRS from the canvas. If not expunged, the height of the QRS becomes an obstacle for maximum magnification of the P and T waves using the voltage optimization feature of CVAT. Magnification of the P and T waves using pixel interpolation is a great aid for precise identification of the beginning and end of the waves. Resampling to a higher sampling rate expands the time domain and adds precision to time intervals measurement. Using CVAT time intervals can be measured to the 10,000 th of a millisecond.

Figure 34:
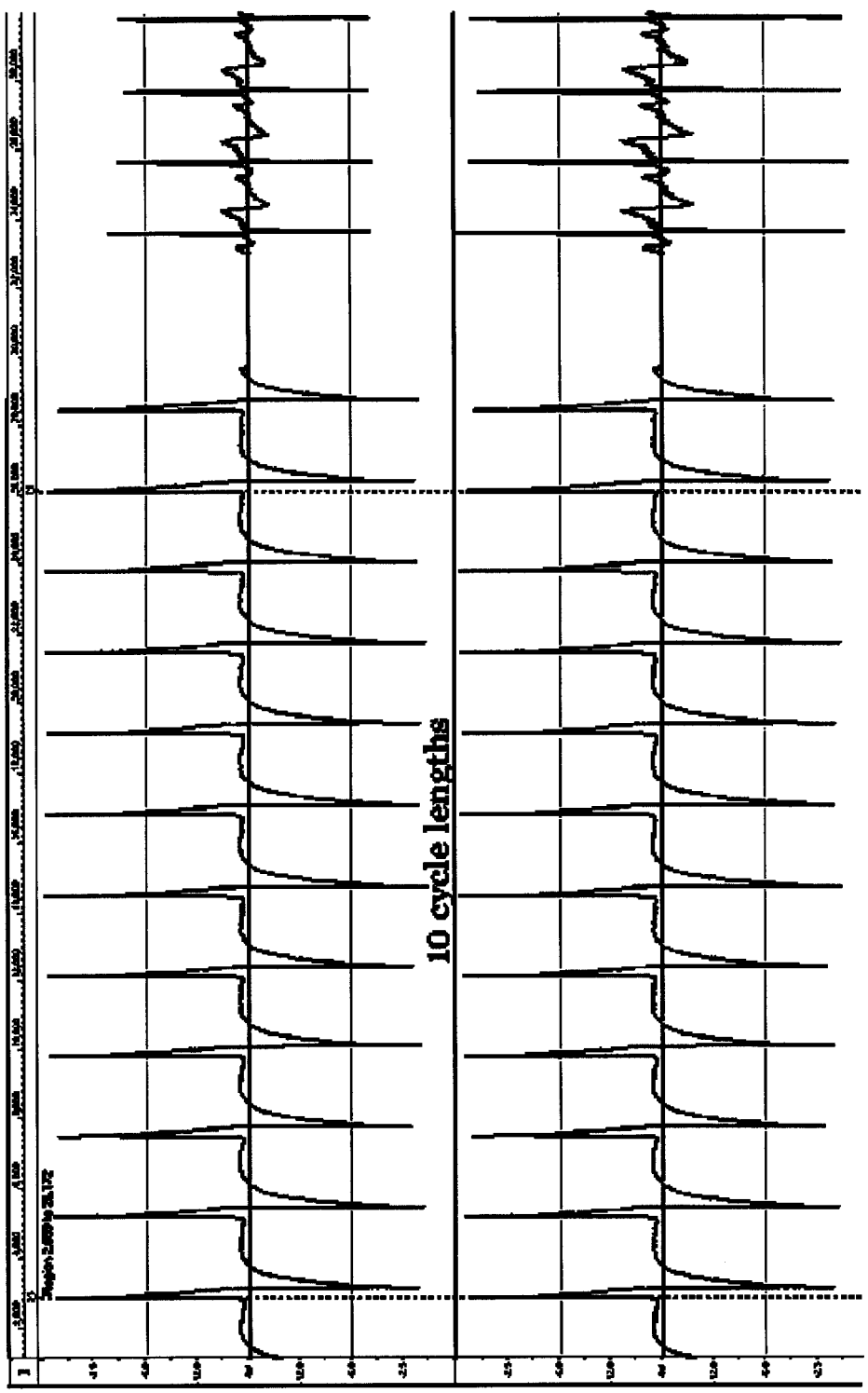
FIG. 34. Illustrates use of the calibration signal to find the number of samples per second of clock time during the recording period.

FIG. 34 shows a canvas in which the signal in the upper channel was copied into the lower channel for the purpose of demonstration of the steps described above. Both channels were resampled from 44,100 to 96,000 Hz. Only the lower channel was voltage optimized. The record calibration voltage waxed and waned in height between 68 and 100%. This is a reason not to trust voltage measurements from Holter recordings. Six calibration cycle lengths on either side of the tallest signal in a period located about the middle of the calibration segment were transported into the canvas. In FIG. 34, 10 calibration cycle lengths were isolated; cursors were placed at the apex of the first and last signal with the recording opened at 1:1 scale for best visualization and precise placement of the markers. The 10 cycle lengths measured as 23,274 samples; hence One cycle length=1 second=2,327.4 samples.

This is the constant used to calculate the time periods in this recording and in the FIGS. 35 to 38.

Figure 35:
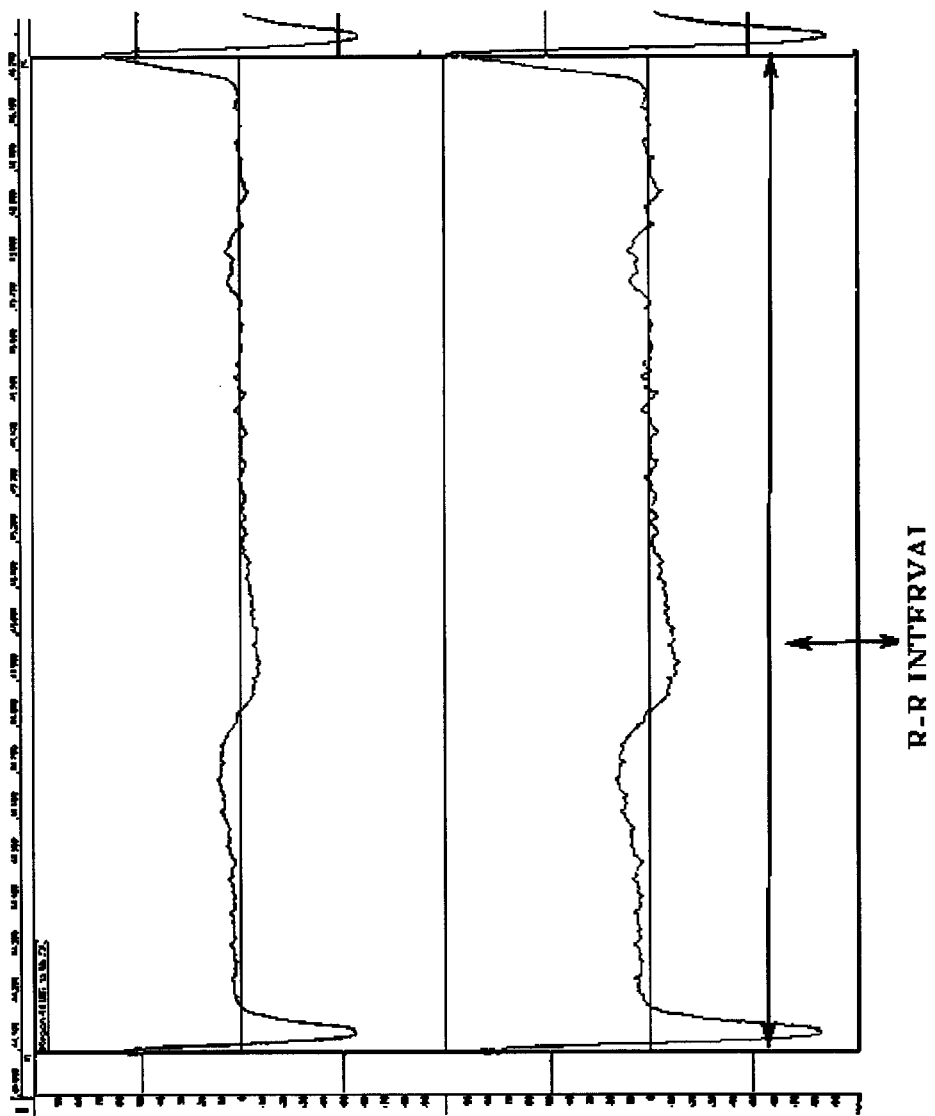
FIG. 35. Illustrates measuring cycle length in a resampled and voltage optimized tracing.

FIG. 35 shows one heartbeat with the cursors placed at the apex of two consecutive R waves with the screen opened at 1:1 ratio, to fit the figure into a size suitable for reproduction, the window was contracted to 1:2 ratio. There were 2,153 samples from R to R, hence 2,153/2,327.4=0.9250665 seconds which gives an instantaneous heart rate of 64.86 beats per minute.

Figure 36:
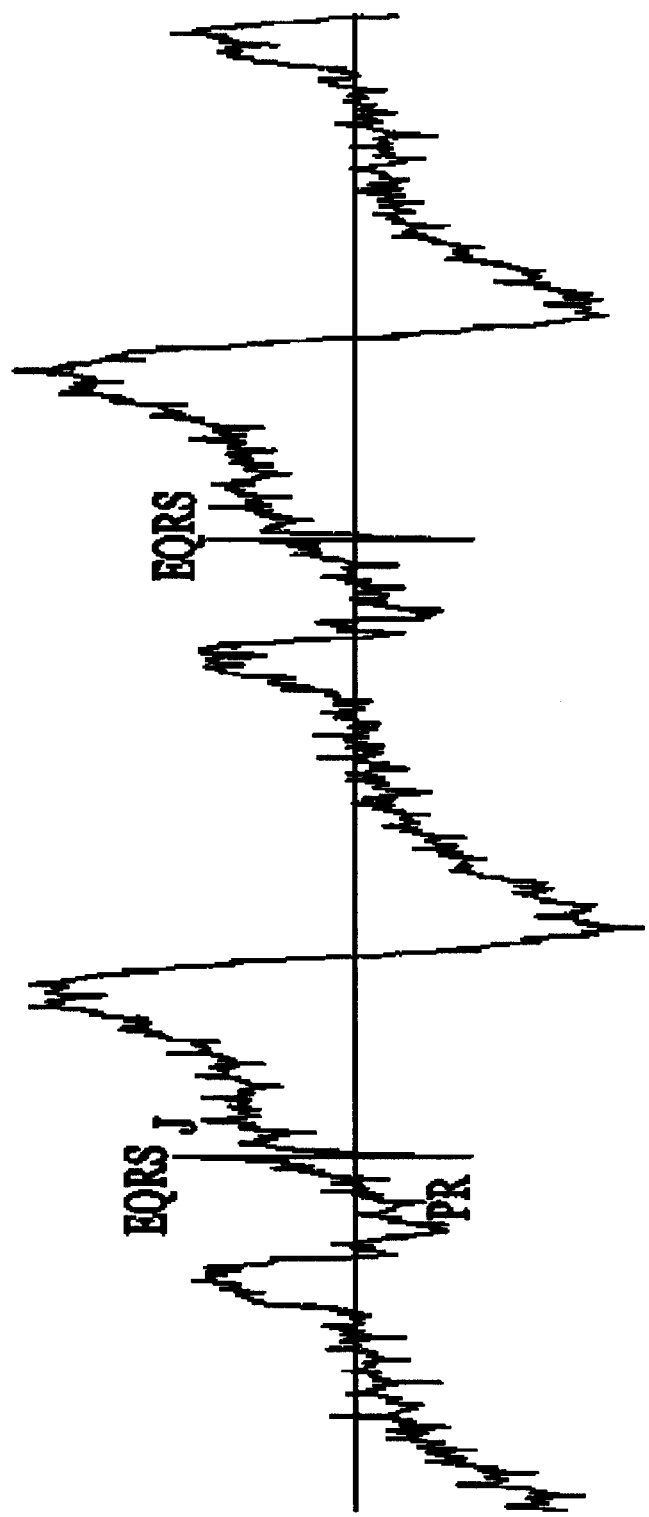
FIG. 36. Shows expunged QRS to magnify microvolt range waves.

To obtain the full benefit of voltage optimization of the P and T waves, the central portion of the QRS was excised in FIG. 36. After voltage optimization the tracings were further magnified to best visualize the microvolt components of the ECG and allow precise identification of the T and P morphology. The small sharp spikes between the P and the T waves are the take off of the R wave and the return to the isoelectric line of the S wave. These landmarks have been left to identify the PR and J points respectively, as noted in the figure.

Figure 37:
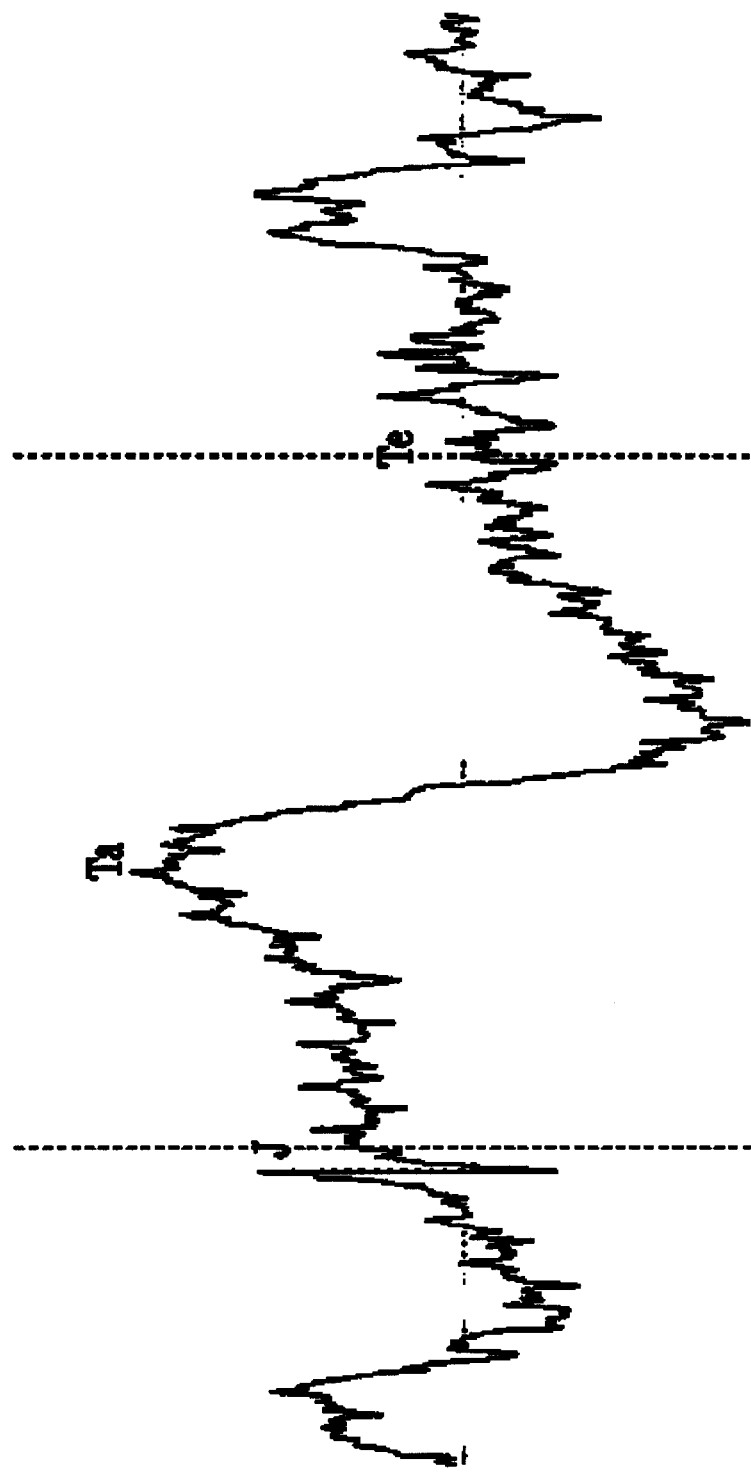
FIG. 37. Shows measuring of J-Te.

FIG. 37 is a close-up of the beat used to calculate the instantaneous heart rate in FIG. 34. Cursors were placed at the J point and at the end of the T wave (Te) located visually with the window opened at 1:1 scale. Precise placement of the cursor at the end of the T was verified as the intersect of end of the negative phase of the biphasic T with a line traced from the beginning of two consecutive P waves taken as the isoelectric line. The number of samples from the J point to the end of the T wave were 1,163 which divided by the number of samples for one second (2,327.4) equals 0.4996992 seconds.

Figure 38:
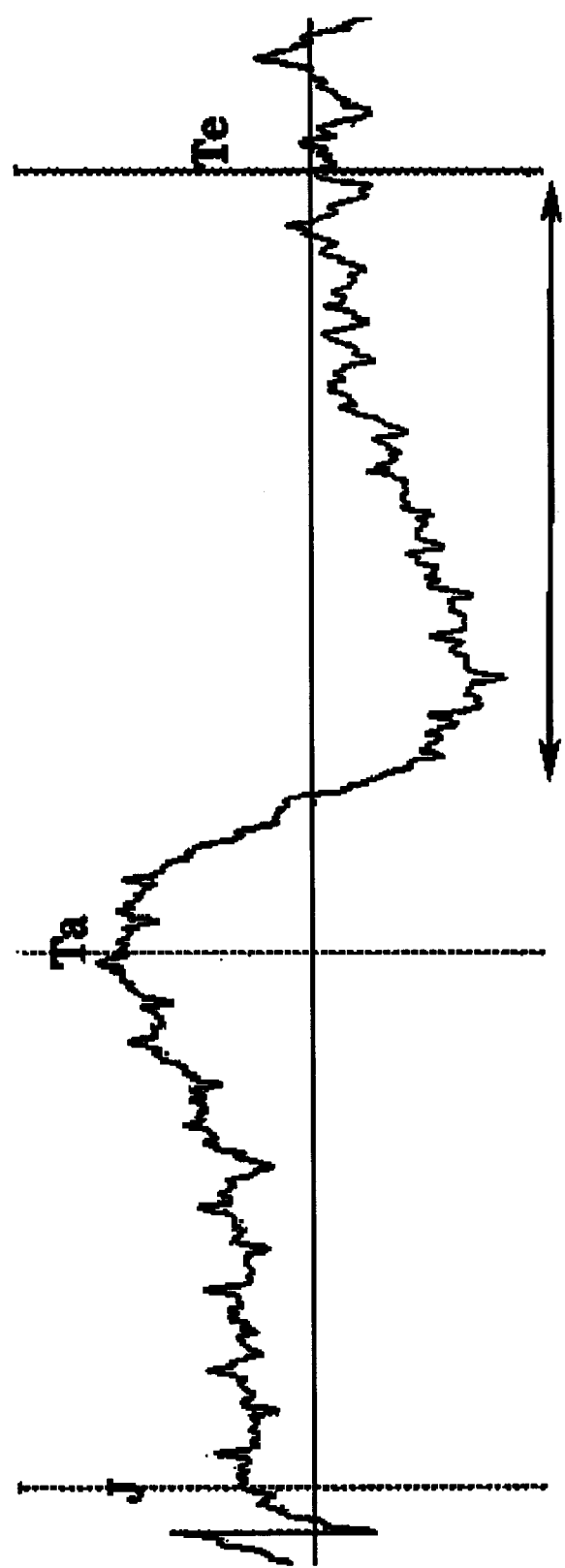
FIG. 38. Illustrates reason for algorithm failure to measure biphasic T waves.

FIG. 38 shows time measurement from the apex of the T (Tp) to the end of the T (Te) for the same beat in a 1:1 scale. Tp-Te equals 692samples divided by the constant 2,327 equals 0.2973274 seconds for mesocardial and endocardial repolarization time. FIG. 38 also shows the difference (black area) that would exist between an automated slope based T wave measurement and CVAT. The algorithms for automated QT interval measurement from Holter tapes would fit a slope on the descending limb of the positive (first half) segment of the biphasic T wave. By doing so the algorithms would disregarded the 450 samples of the negative phase of this biphasic T. A slope based measurement would have resulted in 450 samples, or 0.1933488 seconds, shorter T wave (J-Te at 0.3063504 seconds instead of 0.4996992 seconds), a greater difference than that between normal and pathologic states JT dispersion and circadian variation and relationship with R-R (J-J) changes can be measured by selecting 5 to 10 beats at regular intervals depending on the purpose of the measurement. Within the constrains imposed by variation in the tape recording speed, CVAT gives a better measurement of time intervals than current algorithms.

Next, the evaluation of implanted pacemakers function in accordance with CVAT will be described. The high fidelity, high dynamic range of CVAT makes it suitable for pacemaker function evaluation.

Figure 39:
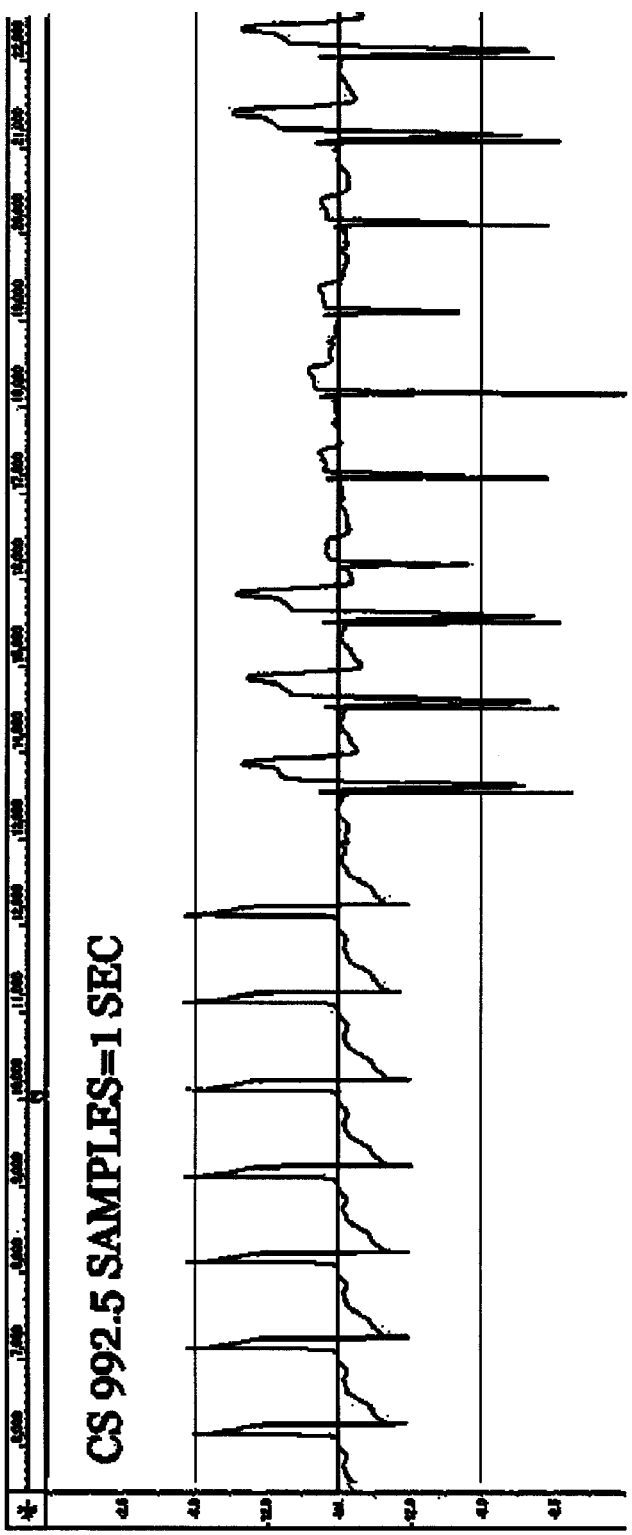
FIG. 39. Shows time conversion to measure pacemaker function.
Figure 40:
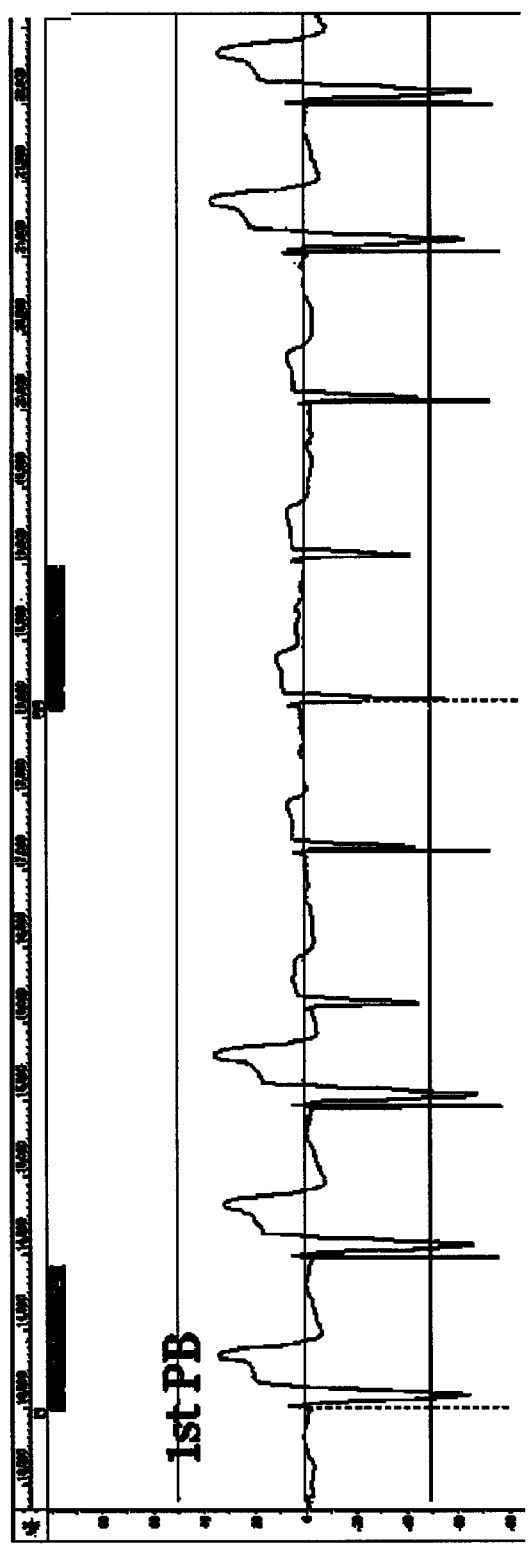
FIG. 40. Shows pacemaker triggered beats evaluated.

FIG. 39 shows an excerpt of one lead of a recording showing calibration signals and paced beats. The average duration of one cycle length of the calibration signals is 992.5 samples, which is to be taken as being equal to one second in this recording. The time between the first and second pacemaker spike is 979 samples divided by 992.5 equals 0.9863979 seconds. There are 14 samples from the beginning of the pacemaker spike in the 1st beat to the apparent take off of the ventricular depolarization which equals 0.0141057 seconds. The 4th ventricular depolarization is not pacemaker triggered and happens at 0.6811083 seconds (676samples) from the previous pacemaker spike. The $5^{th}$ ventricular depolarization is pacemaker triggered at 1.0448362 seconds from the onset of the non-pacemaker triggered ventricular depolarization. It seems that the $5^{th}$ pacemaker spike happened when spontaneous ventricular depolarization had just started similarly to the $8^{th}$ depolarization which started 1.0508816 seconds after the onset of the spontaneous $7^{th}$ depolarization in this series of consecutive paced and non paced beats. FIG. 40 is a close up of these paced beats. To the best of the inventors' knowledge, this kind of evaluation is not possible with current Holter algorithms.

CVAT's application to on-line electrocardiographic monitoring in intensive care areas will now be described. It is known that traditional on-line electrocardiographic monitoring is efficacious for arrhythmia detection done with QRS driven algorithms. However, on line detection of ischemia is unreliable and alternative methods, such as vectocardiography, are being intensively tested. Vectocardiography requires very skilled operators and it is not cost effective for widespread use. CVAT compressed patterns facilitates ischemia detection by those unskilled in electrocardiography, including patients, after a very brief instruction period.

For on-line use of CVAT, the ECG signal is split and fed to an oscilloscope and to the sound card of a computer (including palm and lap tops). The signal is displayed in one CRT or LCD screen with two windows. One window shows the real time ECG, another shows the $\frac{1}{64}$ to $\frac{1}{256}$ (according to the heart rate) visually compressed CVAT signal corresponding to the last 2 or more minutes. The CVAT visually compressed analog ECG clearly shows ischemic patterns which in the real time display are likely to go unnoticed because of their slow onset, observers lack of electrocardiographic sophistication, visual fatigue etc.

CVAT's application to sleep apnea will now be described. A small microphone is used to record respiratory sounds preferably from the area surrounding the upper airway between the soft palate and the larynx. The sound signal is fed into one channel of a Holter recorder which is used to simultaneously monitor two ECG leads (one right and one left precordial lead). Sound frequency analysis is used to recognize normal breathing sound from snoring and apneic spell induced by central or peripheral sleep apnea. The simultaneously recorded electrocardiogram is used to monitor the impact of sleep apnea in cardiac electrophysiology, and determine the need for appropriate therapy. This apparatus and method can replace costly in-hospital somnographic studies and provide a cost-effective mean to diagnose and monitor sleep apnea patients at home.

EXPERIMENTAL RESULTS
A COMPARISON OF THE RESULTS OF PAIRED ANALYSIS OF HOLTER TAPES USING A CONVENTIONAL ALGORITHM AND CVAT
OBJECTIVE

The purpose of this study was to compare the relative efficacy of two different computer-aided 24 hours Holter monitoring analysis techniques to detect ischemia in 24 hours magnetic tape Holter recordings.

An officer of the company which provided the Holter tapes and a copy of the corresponding report, selected the tapes to be analyzed. Initially, at the request of the CVAT inventors and analyzer, tapes known to have signs of ischemia were selected. Later in the study, random tapes were sent for CVAT analysis. Hence, a selection bias was initially introduced, at the request of the CVAT analyzer; such conscious bias should work against CVAT and in favor of the algorithm method.

A total of 67 tapes were analyzed by both methods and the findings are reported below. The Holter recorded analog signal, as retrieved by the CVAT technology, is archived in compact discs to avoid tape stretch and other artifacts, should reanalysis be desired. The reports are identified by the five-digit number assigned at the source of the Holter tapes followed by a capital letter which identifies the compact disc in which the analog signal is kept.

A state-of-the-art computer algorithm was compared to the instant CVAT method for the retrieval, uploading and analysis of the ECG signal encoded in the Holter magnetic tapes. All the electrocardiographic signs detected with CVAT are classical for ischemia as described in standard electrocardiography textbooks and peer reviewed journals.

RESULTS

The following table identifies the tapes which had:

No ischemia

Ischemia found by both the algorithm and CVAT

Ischemia detected by the algorithm but not by CVAT and

Ischemia identified by CVAT but not by the algorithm

| NO ISCHEMIA N = 5 | ISCHEMIA FOUND BY CVAT AND ALGORITHM N = 12 | ISCHEMIA FOUND BY ALGORITHM ONLY N = 1 | ISCHEMIA FOUND BY CVAT ONLY N = 49 |
|---|---|---|---|
|  | 87250 A | | 87247 A |
|  | 87251 A | | |
|  | 87138 A | | |
|  | 87240 B | | |
| 87245 B | | | 87246 B |
|  | | | 87133 B |
|  | 87083 C | | |
|  | | | 87015 C |
|  | 87016C | | |
|  | 86952C | | |
|  | | 87084 D | |
|  | | | 87115 D |
|  | | | 87132 D |
| 87143 D | | | |
|  | 87253 E | | |
| 87321 E | | | |
|  | | | 87344 E |
|  | | | 87331 F |
|  | | | 87337 F |
|  | | | 87339 F |
|  | | | 87341 F |
|  | | | 87325 G |
|  | | | 87327 G |
|  | | | 87340 G |
|  | | | 87442 G |
|  | | | 87438 H |
|  | 87441 H | | |
| 87443 H | | | |
|  | | | 87450 H |
|  | 87356 J | | |
|  | | | 87369 J |

| NO ISCHEMIA N = 5 | ISCHEMIA FOUND BY CVAT AND ALGORITHM N = 12 | ISCHEMIA FOUND BY ALGORITHM ONLY N = 1 | ISCHEMIA FOUND BY CVAT ONLY N = 49 |
|---|---|---|---|
| | | | 87371 J |
| | 87372 J | | |
| | | | 87376 K |
| | | | 87377 K |
| | | | 87378 K |
| | | | 87379 K |
| | | | 87380 L |
| | | | 87383 L |
| | | | 87385 L |
| | | | 87479 L |
| | | | 87490 M |
| | | | 87495 M |
| | | | 87497 M |
| | | | 87499 M |
| | | | 87480 N |
| | | | 87494 N |
| 87498 N | | | |
| | | | 87496 N |
| | | | 87500 O |
| | | | 87507 O |
| | | | 87513 O |
| | | | 87536 O |
| | | | 87510 P |
| | | | 87523 P |
| | | | 87525 P |
| | 87526 P | | |
| | | | 87527 Q |
| | | | 87528 Q |
| | | | 87529 Q |
| | | | 87533 Q |
| | | | 87535 R |
| | | | 87537 R |
| | | | 87538 R |
| | | | 87544 R |

Hence 62 of the 67 tapes analyzed had ischemic electrocardiographic signs. Of these 62, one (1.5%) was detected by the algorithm only, 12 (20%) by both the algorithm and CVAT, 61 (98.4%) by CVAT and 49 (78.5%) by CVAT only. The following results deserve comment:

Holter No 87084 D

Was the only tape in which the algorithm found electrocardiographic signs of ischemia and CVAT did not. This is a single lead recording of less than optimum quality, the algorithm found ST elevation in this single lead. CVAT did not find ST elevation but J depression with biphasic and inverted T waves. To keep the bias constant and against CVAT, this will not be considered a false positive finding.

Holter Tapes in Which Ischemia was found by both, the Algorithm and CVAT

87250 A

The algorithm found ST depression in the upper lead only CVAT found ST depression in both leads

87251 A

The algorithm found ST depression in the upper lead only CVAT found ST depression in both leads

87240 B

The algorithm found ST segment "sagging" in the upper lead only CVAT found ST depression in the upper lead and elevation in the lower lead

87083 C

The algorithm found slight ST depression in the upper lead CVAT found ST depression in the upper lead and elevation in the lower lead

87016C

The algorithm found ST depression in the upper lead CVAT found ST depression in the upper lead and elevation in the lower lead

86952 C

The algorithm found ST depression in the upper lead CVAT found ST depression in the upper lead and elevation in the lower lead

87441 H

The algorithm found ST depression in the upper lead only CVAT found ST depression in the upper and lower lead with shifts to ST elevation in the lower lead

87356 J

The algorithm found ST depression in the upper lead only CVAT found ST depression in the upper and lower leads

87372 J

The algorithm found ST depression in the upper lead CVAT found ST depression in the upper lead and elevation in the lower lead

87526 P

The algorithm found 2 minutes of ST depression in the upper lead CVAT found constant ST depression in the upper lead with ST depression shifting to elevation in the lower lead.

The algorithm and CVAT had concordant ST segment findings in tapes No 87138 A and 87253 E only. In both instances, the ST segment depression was in the upper lead only. In 10 out of 12 tapes the algorithm did not find ST shifts in the lower lead which were detected by CVAT. The right precordial lead seems to be the one recorded in the lower lead and frequently it is of lower voltage (and hence dynamic range) than the upper lead. The lower voltage probably renders the right precordial lead more susceptible to greater obliteration of the signal by the under-sampling, compression, smoothing and filtering used by the algorithm.

CONCLUSION

Of the 62 patients who had ischemic electrocardiographic signs in the Holter tapes, 61 (98.4%) were detected by CVAT and 13 (20.9% including a probably false positive finding) by the algorithm. This ratio is similar to previous experience comparing algorithms versus visual analysis of the magnetic tape where eight or nine out of ten patients known to have ischemia were missed by different algorithms tested. In 10 of 12 instances of ischemia detected by both methods, the algorithm failed to detect ischemic signs in the right precordial lead. The high rate of ischemia found in the total sample is not representative of the general population but probably reflects pre-selection bias introduced by the perceived need for Holter evaluation as part of a cardiovascular work up. It is known that a common reason for arrhythmia is myocardial ischemia, be it symptomatic or silent.

As explained in detail above, the instant invention uses algorithms and software in a novel way for the analysis of electric, magnetic and/or pressure waves of biological origin with the purpose of facilitating the diagnosis of pathologic states in human and veterinary medicine. The technique is applicable (but not limited to) the analysis of signals encoded in the electrocardiogram, electroencephalogram, myography, nerve conduction, plethysmography and other respiratory functions, blood, intracardiac, intracerebral and other vital fluid pressures.

As explained above, an actual reduction to practice has been done using the algorithm encoded in the SOUND FORGE XP, VERSION 4.0 software, developed and marketed by SONIC FOUNDRY, a company located at 754 Williamson St. Madison, Wis. 53703. Another program used is the EASY CD CREATOR, DELUXE EDITION, developed and marketed by Adaptac, Inc. 691 South Milpitas Blvd., Milpitas Calif. 95035. The signal processed to test the instant invention was obtained through Holter recordings of the ambulatory electrocardiogram.

In accordance with the invention, the analog signal from, for example, a Holter recording, is digitized, not to subject the digital file to analyzes through mathematical, algebraic, neural network or any other type of algorithms, but to optimize the high fidelity reproduction, reconstruction, compaction, etc. of the signal to facilitate quick visual scanning of the dynamic electrocardiogram. Improving the state of the art sensitivity and specificity of the analysis while preserving cost effectiveness are primary objects of the present invention.

The digital file is used to reconstruct a high fidelity rendition of the originally recorded analog signal for visual analysis using different rates of compression (compaction) of the original wave form to facilitate visual searching for the classic electrocardiogram signs of ischemia which have been described heretofore mainly during studies of ischemia induced during exercise tolerance testing and lately during percutaneous balloon dilation of the coronary arteries.

In accordance with a preferred embodiment of the instant invention, the signal is digitized at 44,1000 HZ/SEC versus 125 (commercial) and 500 HZ/SEC (Harvard) using 16 bits instead of the conventional 12 bits. This feature enables at least one or more orders of magnitude improvement in the measurement of wave amplitude and duration. Off the shelf sound editing software is preferably used to optimize the digital storage of the analog signal to then do digitally enhanced, high fidelity reconstruction of the analog signal. The digitized wave files are also suitable for compression to facilitate their transport through different media. The instant invention enables reconstruction and optimization of poor signals originally recorded into the magnetic tape.

The invention enables quick scanning and identification of electrocardiographic abnormalities by using the following techniques:

digital acquisition of the ECG analog signal from the Holter tape at 44,100 (or higher) HZ/SEC;

digitize through 16 bits card or higher;

reproduction and optimization of the analog ECG signal using a high fidelity music editing software program such as SOUND FORGE;

Visual analysis of the reconstructed compacted analog ECG signal is facilitated by the use of different rates of compression and decompression as well as the proper colors to enhance the contrast between the signal and the background. The particular heart rate generally determines the optimal rate of compression which preferably ranges between 1/32 and 1/256. Color further facilitates an accurate visual analysis thereof. It has been found that the use of a red signal on a black background provides the best contrast, but other colors, as well as black and white, may be used;

normalization, signal smoothing, image contrast enhancement, and gain increase available for example, in music editing program such as SOUND FORGE, are also tools which can optionally be used during analog signal preparation and reconstruction;

The invention has identified a number of compacted analog signal patterns some of which are shown and described herein, which point to discrete classic electrocardiographic abnormalities including, but not limited to, all the classic signs of myocardial ischemia described heretofore. All forms of electrical alternans are readily identified using these patterns. Familiarity with these patterns is crucial for the quick identification (at a fast scanning rate) of abnormal states which can be done by individuals, such as high school graduates with minimum training; and electrocardiographic analysis is thus reduced to a pattern recognition process accessible to all health care personnel and not restricted to highly skilled, cardiology trained professionals;

In accordance with the instant invention, suitable hardware and software can be used for direct digital acquisition of the signal (to replace initial storage into magnetic tape) through long periods (days).

It is noted that the inventor has determined that red signals and black backgrounds provide the best contrast for viewing most of the signals in accordance with the instant invention. The instant inventor has found that visual analysis is easier when such a color contrast is used. In fact, it has been determined that in many instances black and red contrast provides optimal conditions for the visual analysis.

It is also noted that the graphs herein are only exemplary and that other patterns may be used in accordance with the instant invention. The instant invention enables 24 hrs of recorded heartbeats to be accurately analyzed visually in approximately 20 minutes or less, thereby making visual analysis cost effective while also improving the detection of abnormalities.

While the preferred forms and embodiments of the instant invention have been illustrated and described it will be apparent to those of ordinary skill in the art that various changes and modifications may be made without deviating from the inventive concepts and true spirit of the invention as set forth above, and it is intended by the appended claims to cover all such changes and modification which come within the true scope of the invention.

What is claimed is:

1. Method of analyzing biological signals representative of voltage changes, comprising obtaining an analog biological signal representative of voltage changes, using digital processing software to digitize said biological signals, displaying said processed biological signal in analog form on a display in a time compressed format, wherein an amount of compression for said time compressed format is selected such that graphical patterns are made perceivable on the display that signify an abnormality in the biological signal, and visually analyzing said biological signal on said display to characterize said abnormality.

2. Method of claim 1, wherein said biological signal is an electrocardiogram.

3. Method of claim 1, further including performing independent channel enhancement of the dynamic range of said analog biological signal prior to said digitizing.

4. Method of claim 1, wherein visually analyzing includes attempting to match patterns in said biological signal with a given library of patterns.

5. Method of claim 1, wherein electronic independent optimization of the dynamic range in each channel is done prior to said digitizing.

6. Method of claim 1, wherein said digitizing is performed by sampling said biological signal at at least approximately 44,100 Hz per second per channel.

7. Method of claim 6, wherein said digitizing is performed using quantization of at least 16-bits per sample per channel.

8. Method of claim 1, wherein said digital processing software is digital audio processing software.

9. Method of claim 1, further including the step of using time intervals in the biological signal to assess internal functional harmony of the biological signal.

10. Method of claim 1, wherein digitizing includes using computer sound cards to digitize the biological signal.

11. Method of claim 1, wherein visually analyzing said displayed signal includes looking for abnormalities from the group consisting of: myocardial ischemia, arrhythmia, repolarization, depolarization heterogeneity, and pacemaker malfunction.

12. Method of claim 1, wherein said displaying includes magnifying said displayed biological signal in a Y axis to enable at least microsecond levels of said biological signal to be viewed.

13. Method of claim 1, wherein said displaying includes magnifying said displayed biological signal in an X axis to enable at least microvolt levels of said biological signal to be viewed.

14. Method of claim 1, further including using said method for mass screening of the human population for abnormalities.

15. Method of claim 1, wherein said magnetic recording media is a cassette tape and said digitization includes using a slow playback speed for said cassette tape.

16. Method of claim 15, wherein said slow playback speed is selected to be approximately 40 mm per second.

17. Method of claim 7, wherein said magnetic recording media is a cassette tape and said digitization includes using a slow playback speed for said cassette tape.

18. Method of claim 1, wherein said biological signal is an electroencephalogram.

19. Method of claim 1, wherein said biological signal is a myogram.

* * * * *